United States Patent
Fisker et al.

(10) Patent No.: US 11,633,265 B2
(45) Date of Patent: Apr. 25, 2023

(54) DYNAMIC VIRTUAL ARTICULATOR FOR SIMULATING OCCLUSION OF TEETH

(71) Applicant: 3Shape A/S, Copenhagen K (DK)

(72) Inventors: Rune Fisker, Virum (DK); Christophe Vasiljev Barthe, Copenhagen N (DK); Kasper Kabell Kristensen, Vanlose (DK); Tommy Sanddal Poulsen, Altered (DK)

(73) Assignee: 3SHAPE A/S, Copenhagen K (DK)

( * ) Notice: Subject to any disclaimer, the term of this patent is extended or adjusted under 35 U.S.C. 154(b) by 510 days.

(21) Appl. No.: 16/229,373

(22) Filed: Dec. 21, 2018

(65) Prior Publication Data

US 2019/0290408 A1    Sep. 26, 2019

Related U.S. Application Data

(63) Continuation of application No. 13/580,876, filed as application No. PCT/DK2011/050047 on Feb. 17, 2011, now abandoned.
(Continued)

(30) Foreign Application Priority Data

Feb. 25, 2010 (DK) .......................... PA 2010 00156
May 14, 2010 (DK) .......................... PA 2010 00425
Sep. 17, 2010 (DK) .......................... PA 2010 00835

(51) Int. Cl.
*A61C 11/00* (2006.01)
*A61C 13/00* (2006.01)
(Continued)

(52) U.S. Cl.
CPC .......... *A61C 11/00* (2013.01); *A61C 13/0004* (2013.01); *A61C 19/05* (2013.01);
(Continued)

(58) Field of Classification Search
CPC ..... A61C 11/00; A61C 13/0004; A61C 19/05; A61C 13/097; A61C 9/0053; A61C 9/0086; A61C 19/45; G16H 20/40; G16H 50/50
See application file for complete search history.

(56) References Cited

U.S. PATENT DOCUMENTS

| 5,850,560 | A | 12/1998 | Kang |
| 6,152,731 | A | 11/2000 | Jordan et al. |

(Continued)

FOREIGN PATENT DOCUMENTS

| EP | 1 510 185 A2 | 3/2005 |
| JP | 2005-193028 A | 7/2005 |

(Continued)

OTHER PUBLICATIONS

Myszkowski, K., et al. "Computer Modeling for the Occlusal Surface of Teeth" IEEE Proceedings of CG Int'l '96, pp. 191-198 (1996) available from <https://ieeexplore.ieee.org/abstract/document/511861> (Year: 1996).*

(Continued)

*Primary Examiner* — Jay Hann
(74) *Attorney, Agent, or Firm* — Buchanan Ingersoll & Rooney P.C.

(57) ABSTRACT

Disclosed is a computer-implemented method of using a dynamic virtual articulator for simulating occlusion of teeth, when performing computer-aided designing of one or more dental restorations for a patient, where the method includes the steps of: providing the virtual articulator including a virtual three-dimensional model of the upper jaw and a virtual three-dimensional model of the lower jaw resembling the upper jaw and lower jaw, respectively, of the patient's mouth; providing movement of the virtual upper jaw and the virtual lower jaw relative to each other for simulating dynamic occlusion, whereby collisions between teeth in the
(Continued)

virtual upper and virtual lower jaw occur; wherein the method further includes: providing that the teeth in the virtual upper jaw and virtual lower jaw are blocked from penetrating each other's virtual surfaces in the collisions.

17 Claims, 35 Drawing Sheets

Related U.S. Application Data

(60) Provisional application No. 61/383,840, filed on Sep. 17, 2010, provisional application No. 61/334,681, filed on May 14, 2010, provisional application No. 61/307,934, filed on Feb. 25, 2010.

(51) Int. Cl.
*A61C 19/05* (2006.01)
*A61C 13/097* (2006.01)
*G16H 20/40* (2018.01)
*A61C 9/00* (2006.01)
*A61C 19/045* (2006.01)

(52) U.S. Cl.
CPC .......... *A61C 9/0053* (2013.01); *A61C 9/0086* (2013.01); *A61C 13/097* (2013.01); *A61C 19/045* (2013.01); *G16H 20/40* (2018.01)

(56) References Cited

U.S. PATENT DOCUMENTS

| | | | |
|---|---|---|---|
| 6,406,292 B1 * | 6/2002 | Chishti | A61C 7/002 433/24 |
| 7,134,874 B2 | 11/2006 | Chisht et al. | |
| 7,361,018 B2 | 4/2008 | Imgrund et al. | |
| 8,021,147 B2 | 9/2011 | Sporbert et al. | |
| 9,675,431 B2 | 6/2017 | Orth | |
| 2002/0048741 A1 | 4/2002 | Jordan et al. | |
| 2002/0150859 A1 | 10/2002 | Imgrund et al. | |
| 2004/0172150 A1 | 9/2004 | Perot et al. | |
| 2005/0118555 A1 | 6/2005 | Sporbert et al. | |
| 2005/0271996 A1 | 12/2005 | Sporbert et al. | |
| 2006/0003292 A1 | 1/2006 | Lauren et al. | |
| 2007/0031774 A1 | 2/2007 | Cinader et al. | |
| 2007/0172112 A1 | 7/2007 | Paley et al. | |
| 2007/0207441 A1 | 9/2007 | Lauren | |
| 2008/0311537 A1 | 12/2008 | Minagi et al. | |
| 2009/0006861 A1 | 1/2009 | Bemmel | |
| 2009/0068617 A1 | 3/2009 | Lauren | |
| 2012/0308963 A1 | 12/2012 | Hasselgren et al. | |
| 2019/0216580 A1 | 7/2019 | Fisker et al. | |

FOREIGN PATENT DOCUMENTS

| | | | |
|---|---|---|---|
| JP | 2009523552 | A | 6/2009 |
| JP | 2010-017 467 | A | 1/2010 |
| WO | 99/15100 | A1 | 4/1999 |
| WO | 02/102270 | A1 | 12/2002 |
| WO | 03/092536 | A1 | 11/2003 |
| WO | 2007/021007 | A1 | 2/2007 |
| WO | 2008/113313 | A1 | 9/2008 |
| WO | 2009/035142 | A1 | 3/2009 |
| WO | 2009/105684 | A1 | 8/2009 |
| WO | 2009/133131 | A1 | 11/2009 |

OTHER PUBLICATIONS

Bisler, A., et al. "The Virtual Articulator—Applying VR Technologies to Dentistry" IEEE Proceedings of Sixth Int'l Conf. on Information Visualization (2002) available from <https://ieeexplore.ieee.org/abstract/document/1028835> (Year: 2002).*
Office Action (Examination report under sections 12 & 13 of the Patents Act, 1970 and the Patents Rules, 2003.) dated Aug. 21, 2019, by the Intellectual property India—Government of India in corresponding Indian Patent Application No. 7722/CHENP/2012, and an English Translation of the Office Action. (5 pages).
Demina, A."Development of the general scheme . . . " ЭлeKTpoнHЬ1й жypHaл No. 10, Oct. 2010г. http://technomag.edu.ru/, 18 Pages.
International Search Report (PCT/ISA/210) dated May 10, 2011, by the Danish Patent Office as the International Searching Authority for International Application No. PCT/DK2011/050047.
Danish Search Report for PA 2010 000156 dated Sep. 30, 2010.
Extended European Search Report dated Sep. 23, 2013, issued by the European Patent Office in the corresponding European Application No. 11746885.0. (7 pages).
Solaberrieta, E., et al. "Design of a Virtual Articulator for the Simulation and Analysis of Mandibular Movements in Dental CAD/CAM" CIRP Design Conference (2009) available from <http://hdl.handle.net/1826/3724>.
Chang, Yu-Bing, et al. "An Automatic and Robust Algorithm of Reestablishment of Digital Dental Occlusion" IEEE Transactions on Medical Imaging, vol. 29, No. 9, pp. 1652-1663 (Jun. 7, 2010).
An English translation of the the Office Action dated Feb. 13, 2015, by The Federal Institute of Industrial 1 Property in corresponding Russian Patent Application No. 2012139477/14(063839), and an English translation of the Office Action (9 pages).
Stakovskaya, E.E., "A use of a facebow when operating articulators" LAB #1. 1008 [Found on the Internet at the website http://www.kavodental.ru/img_ cpm/505_KaVoRussia/files/artikel/2008/2008-01.pdf; published on Oct. 2, 2015] (3 pages).
Extended European Search Report dated Oct. 25, 2019, issued by the European Patent Office in corresponding European Application No. 19166764.1-1126, (7 pages).
The extended European Search Report dated Aug. 12, 2022, by the European Patent Office in corresponding European Application No. 22172598.9. (7 pages).

* cited by examiner

DYNAMIC VIRTUAL ARTICULATOR FOR SIMULATING OCCLUSION OF TEETH

CROSS REFERENCE TO RELATED APPLICATIONS

The present application is a continuation of U.S. application Ser. No. 13/580,876, filed on Nov. 29, 2012, which is a U.S. national stage of International Application No. PCT/DK2011/050047, filed on Feb. 17, 2011, which claims the benefit of: U.S. Provisional Application No. 61/383,840, filed on Sep. 17, 2010; U.S. Provisional Application No. 61/334,681, filed on May 14, 2010; and U.S. Provisional Application No. 61/307,934, filed on Feb. 25, 2010, and claims the benefit of: Danish Application No. PA 2010 00835, filed on Sep. 17, 2010; Danish Application No. PA 2010 00425, filed on May 14, 2010; and Danish Application No. PA 2010 00156, filed on Feb. 25, 2010. The entire contents of U.S. application Ser. No. 13/580,876, International Application No. PCT/DK2011/050047 and U.S. Provisional Application Nos. 61/383,840, 61/334,681, 61/307,934, Danish Application No. PA 2010 00835, Danish Application No. PA 2010 00425, and Danish Application No. PA 2010 00156 are hereby incorporated herein by reference in their entirety.

TECHNICAL FIELD

This invention generally relates to a virtual articulator and to a method of performing virtual articulation. More particularly, the invention relates to a computer-implemented method of using a dynamic virtual articulator for simulating occlusion of teeth, when performing computer-aided designing of one or more dental restorations.

BACKGROUND OF THE INVENTION

An articulator is a mechanical device which provides a simplified geometrical model of the cranium for simulating the relative movements of the human jaws for testing occlusion of teeth. An articulator is used by a dental technician when modelling dental restorations for a patient, and the dental technician may alternate between modelling the restorations and evaluating the function of the bite or occlusion using the articulator. For testing collision of teeth in the upper and lower jaw, the dental technician can use carbon copy paper placed between the teeth of the two jaws in the articulator, and the colliding teeth will be thus colored, when the jaws are moved.

Virtual articulators which are digital representations of articulators are known as described below.

WO 08/113313A discloses a method for the production of a denture comprising the following steps: collection of the biometric data of a patient, namely, the toothed or untoothed mandible and maxilla, the sizing of the jaws, the spatial position thereof relative to the skull, the condyle inclination and the movement of the mandible, and the recording of the mandible movement; implementation of the data in a virtual articulator which is made available in the main memory of the data processing equipment; CAD construction of the individual articulator preformed parts and dental molded bodies based on the collected patient data; production of the individual articulator molded bodies and dental molded bodies by means of a generative manufacturing process based on the recorded biometric data; incorporation of the individual articulator preformed parts and/or dental molded bodies into a standardized articulator housing, or complete generative manufacture of the articulator with individualized molded bodies.

US 2002/048741 discloses a computer implemented method of creating a dental model for use in dental articulation, the method comprising the steps of: providing a first set of digital data corresponding to an upper arch image of at least a portion of an upper dental arch of a patient; providing a second set of digital data corresponding to a lower arch image of at least a portion of a lower dental arch of the patient; providing hinge axis data representative of the spatial orientation of at least one of the upper and lower dental arches relative to a hinge axis of the patient; providing bite alignment data representative of the spatial relationship between the upper dental arch and the lower dental arch of the patient; aligning the upper arch image and the lower arch image based on the bite alignment data; and creating a reference hinge axis relative to the aligned upper and lower arch images based on the hinge axis data.

US 2004/172150A discloses a system for designing a virtual dental model comprising: a virtual articulator representing a three dimensional model of a patient's upper and lower dental arches including data defining a constraint of motion having a plurality of degrees of freedom between said upper and lower dental arches; a simulation analyzer to simulate said motion using said three dimensional model and analyze resulting contacts on portions of said upper and lower arches during said movement to provide contact data, said resulting contacts being characterized by a sequence in time of occurrence; and a designing module to design one of a virtual prosthesis for one of said upper and lower arches and a virtual desired dental modification using said contact data acquired from said simulation analyzer and said virtual articulator.

US 2007/207441 relates to four dimensional modeling of jaw and tooth dynamics where methods and systems are described to digitally model the 4-dimensional dynamics of jaw and tooth motion using time-based 3-dimensional data. Complete upper and lower digital models are registered to time-based 3-dimensional intra-oral data to produce a true 4-dimensional model. Diagnostic and clinical applications include balancing the occlusion and characterizing the geometry of the temporomandibular joint. The 4-dimensional model is readily combined with conventional imaging methods such as CT to create a more complete virtual patient model. In one embodiment the document discloses that a standard centric axis coordinate system and a bite position is defined by: a) determining a lower occlusal plane using the complete lower model; b) setting the lower occlusal plane at a predetermined angle, approximately 15 degrees, to a reference horizontal; c) orienting the model of the lower dental arch with the jaw midline perpendicular to the centric axis; d) using a predetermined axis-incisal distance to complete the location of the lower model and the centric axis; and e) positioning the upper model with respect to the lower using a scan taken at a closed or bite position.

WO 09/133131A discloses a method of using a computer based virtual articulator, the method comprising: loading a digital dental model of a patient into a computer running a virtual articulator simulation program, and simulating one or more virtual functional movements, evaluate at least one parameter related to the movement of the jaw when a dental modification is applied, the at least one parameter related to the movement of the jaw being selected from at least the amount of jaw movement in a certain direction, the speed at which a certain jaw movement is carried out and an angle around which a rotational jaw movement is carried out.

It remains a problem to provide a virtual articulator which imitates and resembles an articulator in an improved manner.

SUMMARY

Disclosed is a computer-implemented method of using a dynamic virtual articulator for simulating occlusion of teeth, when performing computer-aided designing of one or more dental restorations for a patient, where the method comprises the steps of:
- providing the virtual articulator comprising a virtual three-dimensional model of the upper jaw and a virtual three-dimensional model of the lower jaw resembling the upper jaw and lower jaw, respectively, of the patient's mouth;
- providing movement of the virtual upper jaw and the virtual lower jaw relative to each other for simulating dynamic occlusion, whereby collisions between teeth in the virtual upper and virtual lower jaw occur;

wherein the method further comprises:
- providing that the teeth in the virtual upper jaw and virtual lower jaw are blocked from penetrating each other's virtual surfaces in the collisions.

Disclosed is a computer-implemented method of using a dynamic virtual articulator for simulating occlusion of teeth, when performing computer-aided designing of one or more dental restorations for a patient, where the method comprises the steps of:
- providing the virtual articulator comprising a virtual three-dimensional teeth model comprising the upper jaw, defined as the virtual upper jaw, and a virtual three-dimensional teeth model comprising the lower jaw, defined as the virtual lower jaw, resembling the upper jaw and lower jaw, respectively, of the patient's mouth;
- providing movement of the virtual upper jaw and the virtual lower jaw relative to each other for simulating dynamic occlusion, whereby collisions between teeth in the virtual upper and virtual lower jaw occur;

wherein the method further comprises:
- providing that the teeth in the virtual upper jaw and virtual lower jaw are blocked from penetrating each other's virtual surfaces in the collisions.

Consequently, it is an advantage that the virtual articulator is allowed to only perform movements which resembles and imitates the real-life situation in the mouth of a patient or the situation when using a physical articulator, thus the relative movement of the jaws are physiological realistic. Thus it is an advantage that the teeth in the upper and lower jaws in the virtual articulator resemble physical, solid teeth which can collide and touch each other but not penetrate each other. The expression teeth may mean the original teeth in the patient's mouth with and without restorations and restorations which completely replace one or more teeth. Teeth may mean the virtual teeth in the virtual upper and lower jaw model to which no restoration(s) is/are designed. The teeth in opposing jaw are thus not allowed to penetrate each other's virtual surfaces, when they collide as part as the occlusion simulation or test for which the virtual articulator is used. The teeth in the virtual articulator are configured to appear, act or behave as solid objects with an impenetrable surface and with a physical extent corresponding to teeth in a physical articulator. The articulated movements of the jaws are restricted by disallowing jaws, and thus the teeth in the jaws, to penetrate. The teeth in the jaws may be said to be impenetrable or to exhibit impenetrability, which is a quality of matter whereby two bodies cannot occupy the same space at the same time. Thus opposing teeth in the upper and lower virtual jaw cannot occupy the same virtual space at the same time.

It is an advantage that the virtual articulator is configured to be a virtual geometric model, for example of and thereby equivalent to a mechanical system comprising a physical articulator. The virtual articulator automatically moves or allows the user to move the two jaws relative to each other. This movement is confined to the movement allowed by the articulator geometry. The jaws may consist of both preparation scans and designed models.

Alternatively, the virtual articulation may be based on a generic model, a physiologic model, free-movement without constraints etc.

It is an advantage that the virtual articulator can be utilized at any point in the design process of designing dental restorations, such a crowns or bridges, whereby the size and shape of the designed restorations can be tested to check if it is correct, i.e. test whether there is space enough for the designed restorations in the mouth, when the jaws are moving relative to each other. Thus by means of simulating occlusion, the function of the dental restorations are tested. A restoration may be a part of one or more teeth, and therefore the expression "collisions between teeth" is used in the present application, and this expression therefore also comprises or means collision between a tooth and a restoration, collision between restorations, collisions between unmodified teeth etc. Thus a tooth can be both a tooth without a restoration or with a restoration. Thus in this application the term tooth and the term restoration may be used interchangeably about a tooth with a restoration or of a restoration completely replacing a tooth.

In some embodiments the method comprises optionally providing that the designed restoration(s) is penetrable, when colliding with the opposite virtual jaw.

In some embodiments the method comprises providing that the designed restoration(s) is blocked from being penetrable when colliding with the opposite virtual jaw.

In some embodiments the method comprises providing that the designed restoration(s) is penetrable, when colliding with the opposite virtual jaw.

It is an advantage that the restorations can be penetrable or not when designing the restorations, depending on the preference of the operator or user of the software.

It is an advantage that the movement of the virtual articulator is restricted by the inability of the two jaws, including designed models, to penetrate into each other, which is provided to accurately model the grinding of the teeth against each other during chewing and thereby recording contact areas. This makes it possible to evaluate the functional aspects of the designs at any given time in the design process, which is analogous to the manual process using a physical articulator.

The virtual three-dimensional model of the upper jaw and lower jaw, respectively, may comprise the entire jaw or arch or a part of the entire jaw, corresponding to e.g. a number of teeth, such as half of the teeth in the jaw.

The expressions jaw and arch may in some cases in this application be used to denote the same physiologic region.

The present computer-implemented method may be implemented and executed in a software program which performs the virtual articulator simulation.

The virtual articulator simulates the movements of a physical articulator or the movements of the real jaws in the mouth of a patient, and besides not allowing penetration of opposing teeth, the movement of the virtual articulator will also ensure that after teeth collide, the next movement of the virtual jaws will correspond to the movement of the teeth in the mouth or the jaws in a physical articulator will perform after collisions, which is continuing the direction of the motion taken the collisions into account, i.e. direction, velocity, angle of impact etc.

In prior art only static occlusion of a bite may be provided in a computer-implemented method, thus the upper and lower jaw may only be represented in their neutral positions, and no relative movement of them were possible.

Prior art discloses collisions between jaws, and the jaws penetrate each other during collisions. In virtual prior art collisions between virtual 3D teeth models, the models are shown to be penetrable, because they are virtual models, whereby there are no physical barriers between the models. However, according to the present method, the collisions are made to resemble a real life collision in the mouth or in a physical articulator. The present method comprises reproducing collisions between upper and lower jaw as real, physical collisions, where the colliding teeth cannot penetrate each other but glide past each other, which is the natural physical case. The colliding teeth can thus only contact each other, not penetrate, as they are virtually solidified physically instead of being represented as penetrable objects.

In some embodiments the method further comprises simultaneous modeling of the one or more dental restorations and collision testing of the virtual upper jaw and virtual lower jaw.

The method may alternatively and/additionally comprise designing one or more orthodontic procedures for the patient, and/or designing one or more prosthetic procedures for the patient, and/or performing a functional analysis of the patient's teeth.

In some embodiments the method further comprises automatic modelling of dental restorations in opposite positions in the virtual upper jaw and virtual lower jaw, when dental restorations in opposite positions are requested.

In some embodiments the virtual upper jaw and virtual lower jaw are configured to move relative to each other.

The movement or motion may be a free motion, a restricted or constrained motion, a motion based on an articulator model, such as a physical, mechanical articulator model etc.

In some embodiment the virtual upper jaw is fixed such that the virtual lower jaw is configured to move relative to the virtual upper jaw.

The virtual upper jaw may be fixed in the virtual space comprising the virtual articulator and the upper and lower teeth models.

In some embodiments the method comprises performing the collision testing of the virtual upper jaw and virtual lower jaw exclusively along the occlusal axis of the virtual articulator.

In some embodiments the method further comprises fixing the virtual upper jaw to the occlusal axis such that the virtual lower jaw is configured to move relative to the virtual upper jaw.

A common property of most physical articulators is that the lower part holding the lower jaw is fixed to the occlusal axis, because the lower part is resting on a table. The upper part can then be moved relative to the lower part.

It is an advantage that according to the present method the upper jaw is fixed relative to the occlusal axis, which resembles the anatomy of the human cranium, where the upper jaw is fixed to the rest of the cranium and the lower jaw can move relative to the upper jaw. However, alternatively the lower jaw could be fixed to the occlusal axes.

In some embodiments the method further comprises defining a search structure on the virtual upper jaw configured for searching on predefined circular paths around the occlusal axis for detecting collisions with the surface of the lower jaw model.

In some embodiments the method further comprises that the virtual lower jaw is configured to automatically move through at least one predefined path of movement relative to the virtual upper jaw.

In some embodiments the method further comprises detecting the first position on the occlusal axis at which the virtual upper jaw and the virtual lower jaw are in contact.

These embodiments are advantages because in general, calculating collisions between complex 3D models and providing response to collisions for preventing penetration is a computationally expensive problem. However, the computation time can be drastically improved, if suitable 3D search structures on the models are computed prior to the collision tests. Examples of such search structures are bounding volume hierarchies, such as AABB-trees, and space partitioning structures, such as BSP-trees, Octrees and kd-trees.

In physical articulators there are a number of degrees of freedom and one of these degrees of freedoms of movement is given by a rotation axis which models occlusion, also called the occlusal axis.

It is an advantage that in the present virtual articulator, it is sufficient to perform collision test and evaluate the response along the occlusal axis, i.e. for any given configuration of the other degrees of freedom, and thereby finding the first position on the occlusal axis for which the two jaw models are in contact. This reduces the dimensionality of the calculation problem and allows for the use of more specialized search structures, which are aimed at calculating the first point of intersection with a 3D model along a given circular path around a static rotation axis. Thus for each motion step along one of the other axes, i.e. for each degrees of freedom, it may be calculated when and at which points the teeth in the jaws will collide along the occlusal axis. So for each movement of the jaws along any of the axes, the jaws may in principle or calculation-wise be closed and then opened along the occlusal axis for testing collision between teeth. Thus predefined paths of movement along the occlusial axis may be configured, where it may be calculated how, when, where the jaws collide for different situations.

It is thus an advantage to construct a search structure on the upper jaw model specialized at searching on circular paths around the occlusal axis. For any configuration of the other degrees of freedom, such a search structure may be used to perform collision test and response along the occlusial axis by searching from the surface of the lower jaw model. This makes real-time collision test and response possible.

If the upper jaw and the search structure were not fixed, the search structure would otherwise need to be updated or recalculated, whenever the relative location of the jaw model and the occlusal axis changed, which would make real-time simulation infeasible.

In some embodiments the collisions are configured to be registered and visually marked.

An advantage of this embodiment is that when the collision points are registered and detected, entire surfaces of collision points are obtained, and the dental restorations can be designed, modeled or modified based on this. A surface of collision points may be denoted the trace or the trace of motion.

In some embodiments collision points in a collision provides a surface of collision points.

The surface of collision points may provide a trace of motion.

The surface of collision points may be visualized and used to design the restoration(s) with.

A collision depth map may be provided and updates with the surface of collision points.

When unmodified teeth are simulated relative to each other, their motion traces or their surfaces cannot penetrate each other. The same may be the case for a restoration relative to an unmodified tooth.

However, it may alternatively be the case that when a restoration and an unmodified tooth are simulated relative to each other, the motion surface of the restoration may penetrate the unmodified tooth.

Thus the term collision surface or trace of collisions points or collision points surface is used for both describing when unmodified teeth are simulated to move relative to each other where the teeth collide and do not penetrate each other and for describing when a restoration is simulated relative to unmodified teeth where the restoration may penetrate the unmodified teeth, i.e. the restoration and the unmodified may penetrate each other.

The simulated collisions or collision surfaces between unmodified teeth may determine the motion which can be performed between the upper and lower teeth models.

This determined motion may then be used and studied when designing the restoration.

The virtually designed appliance or restoration can be cut or designed relative to the collision trace motion.

In some embodiments the part of the one or more dental restorations which causes a collision is configured to be automatically removed from the respective virtual jaw.

Alternatively, the user can remove the part, e.g. a part of material by selecting it manually in the software program performing the virtual articulator simulation.

Traditionally, restorations were only made on one jaw at the time, not on both jaws simultaneously or concurrently. According to the present method e.g. a crown on a tooth in the upper jaw and a bridge on teeth in the lower jaw, which are opposite to the tooth in upper jaw, can now be designed simultaneously. Thus according to the present method teeth, including opposing teeth in the upper and lower jaw, can be designed, and evaluated with regard to collisions and viewed simultaneously.

In some embodiments the method further comprises that the movement of the virtual upper jaw and the virtual lower jaw relative to each other is configured to be digitally recorded.

An advantage of this embodiment is that when recording the movements, after modeling a restoration, the recording can be played to test the modeling.

In some embodiments a predefined motion of the virtual upper jaw and the virtual lower jaw relative to each other is configured to be played.

In some embodiments the predefined motion comprises movement in one or more of the directions:
 protrusion;
 retrusion;
 laterotrusion to the right;
 laterotrusion to the left;
 mediotrusion to the right;
 mediotrusion to the left;
 latero-re surtrusion to the right;
 latero-re surtrusion to the left.

In some embodiments the predefined motion is configured to be automatically terminated based on one or more constraints.

The constraints may be determined by the boundaries of the teeth. The constraints may be determined by the canines in the upper and lower touching each other.

In some embodiments the method further comprises that during the movement of the virtual upper jaw and the virtual lower jaw relative to each other all the collisions occurring between teeth are registered, and after the movement is finished, modeling of the collision points of the restorations is performed.

Thus a movement of the jaws in a continuous motion is performed, i.e. such that one jaw performs a motion completely covering a plane of the other jaw, whereby all collisions between the two jaws, which are possible when taking physiological constraints into account, are registered. Thus the collisions are accumulated, and after the movement is completed and all collisions are registered, then modeling of the collisions points on the restorations is performed. In prior art, a position of the jaws relative to each other is selected, collisions for this position are detected, modeling is performed of the restorations in these collision points, and then a new position is selected, collisions are detected for this position, modeling is performed for the restorations with these collision points etc. Thus no movement, no accumulated registration of collision point surfaces and no possibility to perform a concurrent modeling of restorations based on all collision points are disclosed or possible in prior art. In prior art static occlusion can be detected, but not dynamic occlusion or articulation. Thus in prior art, the jaws are in a static position relative to each other, they can be said to be locked relative to each other.

It is an advantage that the collisions are accumulated, since this gives a collected representation of the contact points or collisions. By viewing the collected representation of the contact points and collisions the dental technician is capable of performing a suitable modeling of all the restorations with collision points.

Furthermore, it is an advantage that a movement of the jaws relative to each other in a continuous motion is performed, since this resembles the use of a physical articulator, which a dental technician may be used to work with. Thus it easy for the dental technician to learn to simulate occlusion in the computer program, because the virtual simulation and modeling resemble the manual simulation and modeling on a physical model using a physical articulator.

In some embodiments automatic modeling of all collision points of restorations are performed concurrently.

Thus modeling of restorations at each collision point can be performed concurrently, simultaneously, at one go etc. Each individual collision point does not need be modeled separately, but some or all collisions points of restorations can be modeled collectively. The modeling may comprise that the parts of the restorations which were detected as contact points are removed, which corresponds to manually removing material from a restoration.

In some embodiments each collision point of a restoration is modeled separately.

In some embodiments restorations are penetrable.

Thus teeth without restorations are impenetrable but the restorations, e.g. the part of a tooth which is a restoration, may be penetrable. This is an advantage when modeling the restorations.

In some embodiments the virtual upper jaw and the virtual lower jaw are configured to bounce back off each other after a collision.

The trace of movement may be recorded, so it can be used in the designing of the restoration(s).

In some embodiments the movement of the virtual upper jaw and the virtual lower jaw relative to each other is configured to be performed in real-time corresponding to natural articulator movements.

In some embodiments the method further comprises selecting a predefined geometrical model for the virtual articulator from among a number of predefined geometrical models.

It is an advantage that the user can select a virtual geometrical model from a number of predefined geometrical models, since the models can represent physical, mechanical articulators of specific brands; geometrical models which the user has defined, standard geometrical models etc. Furthermore, the geometrical model can be a physiologic or biologic model etc., such as a model of the skull geometry. Thus the user can select a geometrical model which suits him or the specific patient case. The selected geometrical model may impose constraints on the movements, or the geometrical model may provide free movement.

The selected geometrical model provides the basis for the articulation and/or occlusion which can be tested or simulated.

In some embodiments the virtual dynamic articulator is configured to be selected from among a number of virtual articulators resembling physical articulators.

In some embodiments the method further comprises selecting a number of degrees of freedom for the geometrical model.

In some embodiments the method further comprises aligning the virtual upper jaw and virtual lower jaw to correspond to the anatomical alignment of the jaws in the mouth of the patient.

This alignment may be defined as a standard alignment.

In some embodiments the anatomical alignment of the jaws is determined by performing a measurement of the patient's facial geometry.

In some embodiments the patient's facial geometry is determined by performing a face scanning of the patient.

The face scanning may result in a three-dimensional (3D) representation of the patient's face. The face scanning may comprise single, still images or may comprise video comprising sequences of still images representing the face in motion. Alternatively and/or additionally the patient's specific facial geometry can be determined by means of traditional face bow or face arches using electronics and optics, where the face bows are attached to e.g. the ears or on the outside of the jaw. Thus when the patient moves his/her jaws, the face bows measure the movements, and the mechanical articulator is adjusted according to this. Movements may comprise swinging of the jaws, opening of the mouth, dragging of the jaw forward, backwards etc.

In some embodiments the method further comprises that the virtual lower jaw is configured to be moved by a user.

Alternatively, both the virtual jaws may be moved relative to each other.

In some embodiments the virtual lower jaw is configured for simulating movements in the following directions:
protrusion (direct forward movement);
laterotrusion and mediotrusion (forward-sidewards movements to both left and right);
retrusion (direct backward movement); and
latero-re surtrusion (to both left and right);

Thus the movement may comprise:
protrusion;
retrusion:
laterotrusion to the right;
laterotrusion to the left;
mediotrusion to the right;
mediotrusion to the left;
latero-re surtrusion to the right;
latero-re surtrusion to the left.

In some embodiments the method further comprises positioning a virtual alignment plane relative to the virtual upper jaw and the virtual lower jaw, where the virtual upper jaw and virtual lower jaw defines a virtual model of the set of teeth, wherein the method comprises the steps of:
visualizing the virtual alignment plane and the virtual upper jaw and virtual lower jaw; and
automatically positioning the virtual alignment plane and the virtual lower jaw and virtual upper jaw relative to each other.

The virtual upper model and/or the virtual lower model may be arranged in the virtual articulator first, and then the alignment plane is positioned afterwards or vice versa.

The virtual alignment plane may also not be visualized, and may thus be invisible or faded.

It is an advantage that the virtual models can be aligned relative to a virtual alignment plane. The virtual alignment plane may be determined e.g. based a plane in a mechanical articulator. In a mechanical articulator there may be a marking, e.g., indentations in the vertical rods, for manually arranging a red rubber-band. The rubber band is used to arrange, such as align, the two physical models of the upper and lower teeth.

In some embodiments the automatic positioning is based on one or more parameters.

In some embodiments the method further comprises positioning a virtual alignment plane relative to the virtual upper jaw and the virtual lower jaw, where the virtual upper jaw and virtual lower jaw defines a virtual model of the set of teeth, wherein the method comprises the steps of:
visualizing the virtual alignment plane and the virtual upper jaw and virtual lower jaw; and
automatically positioning the virtual alignment plane and the virtual lower jaw and virtual upper jaw relative to each other based on one or more parameters.

It is an advantage that the virtual alignment plane and the virtual model of the teeth are positioned relative to each other based on some parameters, because depending on which parameters that are available for the specific patient and case, the relevant available parameters can be used to perform the positioning. If no specific parameters are available for the specific patient, standard or default parameters may be used. But if specific parameters are available for the patient, these parameters may be used such that the result can be achieved faster and with a better result. As mentioned below, the patient-specific parameters may be obtained with a facebow providing information about static occlusion, with an electronic facebow providing information about static and dynamic occlusion, with a face scanner also providing information about static and dynamic occlusion etc.

The virtual alignment plane may be defined or determined in different ways. The alignment plane may be flat, level or even, or curved, irregular, uneven or non-uniform etc. The alignment plane may follow or comply with the shape of the incisal or biting edges and/or cusps of the teeth.

The alignment plane may for example be the curve of Spee. The curve of Spee is defined by that the cusp tips and incisal edges of the teeth align so that there is a smooth, linear curve when viewed from the lateral aspect. The lower curve of Spee is concave whereas the upper curve is convex. Curve of Spee may be called a compensating curve of the dental arch.

The set of teeth may be an entire set of teeth covering all teeth in a patients mouth, or the set of teeth may be a part of an entire set of teeth, thus the set of teeth may also be denoted at least a part of a set of teeth.

The expression "positioning relative to" means that either the virtual alignment plane is fixed in position when seen on e.g. a graphical user interface, such as a computer screen, and then the virtual model is moved, or it means that the virtual model is fixed in position when seen on e.g. the computer screen, and then the virtual alignment plane is moved. In either way the virtual model and the virtual alignment plane are seen to virtually move relative to each other.

Positioning may be defined as placing, arranging etc.

Occlusion may be defined as the contacts between the upper and lower teeth, or as the relationship between the maxillary (upper) and mandibular (lower) teeth when they approach each other, as occurs during chewing or at rest.

In some embodiments the one or more parameters are derived from a face scan of the patient.

It is an advantage that the one or more parameters can be derived from a face scan of the patient, where the movements of the jaws are scanned when the patient performs e.g. dynamic occlusion, because this allows for recording of dynamic movements of the jaw such that dynamic occlusion performed when chewing and open/close movements can be recorded.

The face scan can alternatively and/or additionally be used to measure the static occlusion of the patient.

These static occlusion and the dynamic occlusion for the specific patient can then be used when simulating occlusion on the virtual articulator, and the alignment plane can be positioned relative to the virtual model of the teeth such that it is a physiologically correct alignment for that specific patient.

When the alignment of the teeth in the virtual articulator is identical to the physiologic alignment in the patient's mouth, the articulation and occlusion of the virtual articulator will be physiologic correct, and modelling of restorations can be performed with an optimal fit and result.

As an alternative to using a face scanner, other "live" recording means, such as a CT scan etc. may be used.

Furthermore, in some embodiments the face scanner is used to measure features of the face of the patient, such as the facial midline, the arch midline, the incisal plane, and/or the interpupillary line.

Furthermore, in some embodiments the method further comprises the step of simulating and estimating dynamic occlusal interferences, wherein said interferences are deduced at least partly from a plurality of scans that record said patient's jaw articulation by tracking at least one reference object fixed to the patient's teeth.

Yet a further embodiment comprises the step of calculating the articulation of the jaw and thereby simulating and/or estimating dynamic occlusal interferences.

In some embodiments of the invention the face scanner is used to measure 3D movements of the jaws and face of the patient in real time.

In some embodiments of the invention the face scanner is used to measure the position of the upper jaw and/or lower jaw with respect to the skull. Thus the face scanner may then replace a face-bow, which is traditionally used for this static measurement.

Thus the face scanner can be used to measure planes of the face, such as centric determination or the midline, it can be used to measure jaw movement, and/or it can be used to measure the attachment and/or movement of the jaws relative to the rest of the skull.

Thus the measured jaw motions, which are the physically true motions or movements, are used to simulate the movement in a dynamic virtual articulator, such that dental restorations can be designed, where the dental restorations have improved functionality and aesthetics. Thus the face scanner can perform the relevant measurements for providing a dental restoration, and thereby replacing the use of e.g. face-bows, electronic facebow, use of standard values or setting etc.

In a further embodiment of the invention calculation and/or estimation of the articulation of the jaw and/or the dynamic occlusal interferences is at least partly based on a plurality of face scans and at least one 3D model of the pre-prepared and/or prepared teeth, a 3D model that comprises the antagonist. For optimal accuracy and precision, it is advantageous to fix one or more reference spheres or objects to the teeth.

In some embodiments the movements of the patient's jaws are scanned in 3D and in real-time using the face scanner.

It is an advantage that the face scanner scan in real-time, since real time means that the scanner records movements in real time, i.e. the scanner records the entire movement as it happens, such that every step along the movement is recorded. If the face scanner is not recording in real time the movement itself cannot be recorded but only some separate points, e.g. extremum points of the jaws. If a face scanner only takes a scan every minute or the scan takes a minute to make, that face scanner will not be a real-time scanner, since the jaw and the face muscles move much faster than that in true chewing movements. Thus a real-time face scanner will record gradual movements taking several full 3D frames per second, as known from a video camera.

In some embodiments a virtual plane is defined and arranged relative the virtual articulator.

In some embodiments the virtual plane is fixed relative to the virtual articulator.

In some embodiments the virtual plane is visualized relative to the upper and lower model.

In some embodiments the virtual plane is a virtual alignment plane.

In some embodiments the virtual alignment plane is fixed relative to the virtual articulator.

It is an advantage to arrange a virtual plane or virtual alignment plane relative to the virtual articulator since this may improve the alignment of the upper and lower teeth model relative to each other. It is an advantage that the operator or user may virtually rotate the models with the plane attached to them, and that he may zoom in and study details in the alignment of the models.

In some embodiments the virtual alignment plane is a default occlusal plane.

It is an advantage because a default occlusal plane may be defined as a plane passing through the occlusal or biting surfaces of the teeth. It represents the mean of the curvature of the occlusal surface. It may be defined at the plane stretched between three specific teeth as explained above. Furthermore, the occlusal plane may be defined as an imaginary surface that is related anatomically to the cranium and that theoretically touches the incisal edges of the incisors and tips of the occluding surfaces of the posterior teeth. It represents the mean of the curvature of the surface. Furthermore, the occlusal plane may be defined as a line drawn between points representing one half of the incisal overbite, vertical overlap, in front and one half of the cusp height of the last molars in back. The occlusal plane may on a physical, mechanical articulator be marked with a rubber band placed at specific points relative to the teeth on the model of the teeth, such that the rubber band indicates a plane.

In some embodiments the one or more parameters are derived from a face scanning of the patient, where the movements of the jaws are scanned when the patient performs dynamic occlusion.

In some embodiments the movements of the patient's jaws are scanned in 3D and in real-time using the face scanner.

In some embodiments one or more of the parameters are derived from a facebow measurement of the patient.

It is an advantage to use a facebow to measure the one or more parameters on a patient. A conventional facebow is a device used in dentistry to record static occlusion, e.g. a device to record the positional relations of the upper arch to the temporomandibular joints and to orient dental casts in this same relationship to the opening axis of the articulator. Thus a facebow may enable gathering of information such that a restoration can be made to the exact cranium/axis relationship of the patient and his/her anatomy. By using a mechanical facial bow with electronic measuring system dynamic occlusion can be measured, and the measurement data can be transmitted by wire or wirelessly to the computer, or saved on a memory component. Thus the data from the electronic facebow measurement can be transferred to the computer for assisting in placing the alignment plane relative to the virtual model of the teeth.

An example of an electronic facebow is a facebow which enables a precise measurement by means of a number of sensors, such as sound transmitters and microphones. An electronic facebow can measure the lower jaw movements in relation to the patient's cranium. Alternatively, the electronic facebow can be a facebow using magnetic measurement technology, or the facebow can be a facebow which uses ultrasound measurement technology, or the facebow can be any other electronic system transferring the recorded facebow data to a computer.

A facebow may be attached to the head of the patient, e.g. at, above or in the ears, and to the nasal bone between the eyes. A bite fork with impression material on it may then be placed in the patient's mouth touching the teeth in the upper arch, and by means of e.g. ultrasound measurements, the distance between the bite fork and certain points on the facebow may be determined and/or movements of the jaws can be measured. The distance can be used to derive specific anatomical dimensions of the patients face and/or cranium.

Furthermore, another metal fork may then be arranged on the front surface of the teeth in the lower arch, and the patient may move his/her lower jaw into different extreme positions, and by means of e.g. ultrasound measurements, these movements and extreme positions of the lower jaw relative to the facebow may be measured, and by these measurements dynamic occlusion and/or specific anatomical dimensions of the patients face and/or cranium may be determined.

All the measurements of static and/or dynamic occlusion with the facebow as described above may be made and stored electronically, and the measurements may thus be transferred to a computer on which the computer-implemented method of placing the virtual alignment plane relative to the virtual model of the teeth is performed, and thus the dynamic occlusion measured on the patient may be used to perform the placement of the virtual alignment plane relative to the virtual model of the teeth.

Thus the dynamic occlusion can be recorded electronically and played or replayed, while modelling e.g. a restoration.

Furthermore, in some embodiments information about the lower jaw movements in relation to the upper jaw is transferred from a facebow and used to define the virtual alignment plane.

Furthermore, in some embodiments information about the positional relations of the upper arch to the temporomandibular joints is transferred from a facebow and used to define the virtual alignment plane.

In some embodiments the method further comprises determining the position and orientation of the facebow relative to the patient's upper arch.

In some embodiments the method further comprises determining the position and orientation of the facebow relative to the physical articulator.

In some embodiments the method further comprises determining the position and orientation of the facebow relative to the virtual articulator.

In some embodiments the facebow comprises a bite fork with impression material for providing an impression of the upper arch of the teeth, and the method further comprises determining the position and orientation of the bite fork relative to facebow.

In some embodiments the method further comprises scanning the bite fork with the impression of the upper arch teeth to provide a scan of the impression and a scan of the bite fork.

A scan of the impression, a scan of the bite fork, and a scan of both the impression and bite fork can thus be provided.

It is an advantage to scan the impression on the bite fork material, since hereby the impression can be used in aligning the virtual upper and lower jaw and/or aligning plane etc. Thus the virtual model of the set of teeth can be aligned with the bite fork and/or the impression in the bite fork by aligning the depressions/indentations and peaks/top in the model and in the impression.

In some embodiments the scan of the impression is aligned with the virtual model of the set of teeth.

It is an advantage to align the scan of the impression on the bite fork relative to the virtual model of the teeth, i.e. relative to the upper and lower jaw models. The depressions in the impression material corresponds to the peaks or high points of the teeth, thus the depressions or low points in the scan of the impression fit to the corresponding peaks or high points in the virtual model of the set of teeth.

In some embodiments the method further comprises determining the position and the orientation of the bite fork relative to the virtual articulator.

Thus the facebow has a coordinate system, CF. This coordinate system CF is directly transferred to the mechanical articulator coordinate system CMA when the facebow part with the bite fork is inserted in the mechanical articulator. The physical cast models are then attached to the articulator by means of the facebow information.

If one wishes to get the position and orientation information from the facebow coordinate system CF and the bite fork coordinate system CBF into the virtual articulator coordinate system CVA, this information should be transformed so that it becomes digital or can be turned into values to be read off and typed into the virtual articulator software program.

The distance between the position of the bite fork relative to something on the facebow must be determined and made digital to be transferred into the virtual articulator coordinate system (CVA).

When using an electronic facebow, a distance between the bite fork and a point on the facebow is measured electronically, and this electronic measurement can be transferred to the computer and virtual articulator coordinate system CVA.

The different coordinate systems used may be calibrated with regard to each other.

In some embodiments determining the position and the orientation of the bite fork relative to the virtual articulator comprises adjusting/fitting the scan of the impression into the virtual articulator.

Thus the CAD model or file from scanning of the bite fork can be used to align the bite fork and the impression on the bite fork into the virtual articulator.

In some embodiments determining the position and the orientation of the bite fork relative to the virtual articulator comprises reading off values on the facebow and/or bite fork and typing the values into a user interface for the virtual articulator.

In some embodiments determining the position and the orientation of the bite fork relative to the virtual articulator comprises electronically transferring data from the facebow and/or bite fork to the virtual articulator.

This is possible for example when the facebow is an electronic facebow.

In some embodiments determining the position and the orientation of the bite fork relative to the virtual articulator comprises:
  arranging the bite fork with the impression in a specific holder in a 3D scanner; and
  calibrating the position and the orientation of the holder relative to the virtual articulator.

This may be advantageous when the bite fork has a fixed or determined position relative to the facebow, e.g. when the facebow is an electronic facebow, such that the distance between specific points on the facebow and on the bite fork are measured electronically.

In some embodiments determining the position and the orientation of the bite fork relative to the virtual articulator comprises aligning the scan of the bite fork with a CAD model of the bite fork.

This may be advantageous when the bite fork has a fixed or determined position relative to the facebow, e.g. when the facebow is an electronic facebow, such that the distance between specific points on the facebow and on the bite fork are measured electronically.

The iterative closets point (ICP) method may be used for aligning, and thus the difference or distance between two point clouds from scans or models is minimized.

In some embodiments a transformation between a scan of the impression and/or a scan of the bite fork and/or a virtual model of teeth and/or a CAD model in order for arranging them in the same virtual coordinate system on a user interface is determined through calibration of the different coordinate systems for the scan(s), the CAD model(s) and/or the virtual model(s).

In some embodiments a scan of a physical model of the upper jaw, a scan of a physical model of the lower jaw and a scan of the physical models of the two jaws in occlusion are aligned for deriving occlusion data.

In some embodiments the positioning of the virtual alignment plane relative to the virtual model of the set of teeth is configured to be fine-tuned manually by an operator.

In some embodiments the positioning of the virtual alignment plane relative to the virtual model of the set of teeth is configured to be performed by the operator by selecting one or more virtual points relative to the virtual model of the set of teeth within which point(s) the virtual alignment plane should be moved to.

Thus it may be a one point alignment, a two point alignment, a three point alignment etc. One or more of the points may for example be arranged on posterior molar teeth, such as a first point arranged on the rearmost tooth in the left side of the mouth and a second point arranged on the rearmost tooth in the right side of the mouth. A third point may be arranged in the median line on the central teeth or on one of the central teeth. Points may be arranged on the lower and/or upper jaw.

In some embodiments the one or more parameters are default, standard parameters.

In some embodiments the one or more parameters are patient-specific parameters derived from the specific patient.

In some embodiments the virtual alignment plane is a default alignment plane.

In some embodiments the default alignment plane is pre-defined and determined based on standard values.

In some embodiments the virtual alignment plane is a patient-specific alignment plane, which is determined based on one or more parameters from the patient.

In some embodiments the one or more parameters are derived from the virtual model of the set of teeth.

Thus dimensions of the arches, jaws, of height differences between teeth etc. may be derived from the model.

In some embodiments one or more of the parameters are based on one or more prepared teeth which should be restored.

In some embodiments one or more of the parameters are the position of one or more prepared teeth, the labial or buccal surface direction of the prepared teeth, and/or the upwards or downwards direction of the prepared teeth.

In some embodiments one or more of the parameters are based on the horizontal and/or vertical placement of the one or more teeth.

In some embodiments one or more of the parameters are the position of a number of specific teeth.

In some embodiments one or more of the parameters are based on the highest point(s) of the teeth in the lower arch and/or in the upper arch.

In some embodiments the one or more parameters is a point on a molar tooth in the left side of the lower arch, a point on a molar tooth in the right side of lower arch and a point between the central teeth in the lower arch.

It is an advantage to use these points as the parameters since they define a plane. The points may for example be: the distal-buccal cusp of the second molar in both the left and the right side of the lower arch or jaw, and the point 1 mm below the incisal edge in the space between the two central teeth in the lower arch or jaw. These points define a plane, which may be defined the occlusal plane.

In some embodiments the one or more parameters comprise measurements of and/or values for the:
  condylar angle;
  Bennett side-shift;
  incisal guidance;
  cuspid guidance;
  shape of the glenoid fossae;
  shape of the eminintiae;

position of the maxillae duplicated with respect to the skull; and/or face-bow settings.

It is an advantage to use one or more of these parameters, since they are the areas where a mechanical articulator and thereby also the virtual articulator can be adjusted.

In some embodiments a standard set of teeth is indicated on the alignment plane for assisting the operator to place the alignment plane and the virtual model of the teeth correctly relative to each other.

In some embodiments means for rotating and translating the alignment plane and/or the virtual model of the teeth are provided.

In some embodiments the means for rotating and translating are provided as virtual handles.

In some embodiments the virtual alignment plane and/or the virtual set of teeth is/are semi-transparent or translucent such that both the virtual alignment plane and the virtual set of teeth are visible simultaneously.

Furthermore, a physical cast model of the upper or lower teeth may be attached to a certain male plate which fits both in a corresponding female plate in a 3D scanner and in a corresponding female plate in a mechanical articulator. Hereby transfer of positions on the model between the articulator and the scanner is enabled. The positions determined from this may then be transferred to the computer software where the virtual articulation and modelling of restorations are performed. There may also be certain reference marks on the male plate, on the model etc.

In some embodiments the virtual model of the set of teeth is performed by means of intraoral scanning of the teeth or by scanning an impression of the teeth or by scanning a physical model of the teeth.

In some embodiments the method comprises registering the trace of the collision surface, and automatically cutting away tooth material based on the collision surface.

It is an advantage that a virtual cutting away of material from the modelled teeth can be performed based on the virtual trace of the simulated collision points surface. Hereby the material need not be removed virtually afterwards, but is removed on the fly during the simulation.

The present invention relates to different aspects including the method described above and in the following, and corresponding methods, devices, system, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a dynamic virtual articulator system for simulating occlusion of teeth, when performing computer-aided designing of one or more dental restorations for a patient, where the system comprises:

means for providing the virtual articulator comprising a virtual three-dimensional model of the upper jaw and a virtual three-dimensional model of the lower jaw resembling the upper jaw and lower jaw, respectively, of the patient's mouth;

means for providing movement of the virtual upper jaw and the virtual lower jaw relative to each other for simulating dynamic occlusion, whereby collisions between teeth in the virtual upper and virtual lower jaw occur;

wherein the system further comprises:

means for providing that the teeth in the virtual upper jaw and virtual lower jaw are blocked from penetrating each other's virtual surfaces in the collisions.

Disclosed is furthermore a computer program product comprising program code means for causing a data processing system to perform the method when said program code means are executed on the data processing system; and a computer program product comprising a computer-readable medium having stored there on the program code means.

Disclosed is a computer-implemented method of using a dynamic virtual articulator for simulating occlusion of teeth, when performing computer-aided orthodontic treatment planning for a patient, where the method comprises the steps of:

providing the virtual articulator comprising a virtual three-dimensional teeth model comprising the upper jaw, defined as the virtual upper jaw, and a virtual three-dimensional teeth model comprising the lower jaw, defined as the virtual lower jaw, resembling the upper jaw and lower jaw, respectively, of the patient's mouth;

providing movement of the virtual upper jaw and the virtual lower jaw relative to each other for simulating dynamic occlusion, whereby collisions between teeth in the virtual upper and virtual lower jaw occur;

wherein the method further comprises:

providing that the teeth in the virtual upper jaw and virtual lower jaw are blocked from penetrating each other's virtual surfaces in the collisions.

It is an advantage that the dynamic virtual articulator can be used for treatment planning in orthodontics, since hereby dynamic occlusion for orthodontic cases can be simulated.

In some embodiments treatment planning in orthodontics comprises segmenting teeth, moving teeth, and/or simulating motion of jaws and teeths.

Thus when using a virtual dynamic articulator in treatment planning, teeth segmentation may be performed virtually, teeth movement may be performed virtually, motion simulation may be performed virtually etc.

Treatment planning may comprise providing the existing dental situation for a patient, and providing a desired final dental situation after orthodontic treatment, and then using the method of dynamic virtual articulation for testing and simulating whether the final dental situation is suitable.

When using the method of dynamic virtual articulation in restorative dentistry, a part of a modelled tooth which collides with another tooth can automatically be cut away for avoiding collisions in the real mouth of the patient during real articulation, biting, chewing etc.

However, when using the method of dynamic virtual articulation in restorative dentistry, no teeth parts should be cut away, but a tooth colliding with another tooth may be moved, rotated, turned, etc. in a directions so that undesired collision is avoided in the real bite of the patient.

In some embodiments the method comprises registering the trace of collisions, and based on this the orthodontic treatment, e.g. movement of the different teeth, is planned.

In some embodiments the method comprises assigning a weight to one or more teeth.

In some embodiments the weight assigned to a tooth determines how susceptible the tooth is to movement.

In some embodiments a high weight signifies that the tooth must not be moved, a low weight signifies that it is under all circumstances allowed to move the tooth, and a medium weight signifies that it is allowed to move the tooth if suitable for the treatment.

It is an advantage to assign different weights to the teeth to control and guide the treatment, e.g. movement, since some teeth may have a function or a position already which is important for e.g. the functionality of the bite, and these teeth should maybe by no means be moved. Whereas other teeth have no important function or position, and it may therefore be insignificant for the functionality or visual aesthetics if those teeth are moved. The middle group may comprise a number of different weights over a range, and if two teeth are colliding undesirably during simulating, then for example the tooth with the lowest weight is the one which should be moved.

In some embodiments two or more teeth are locked together, whereby the two or more teeth are configured to move as an entity.

It is an advantage that teeth can be locked together, since it may be desired that for example the front teeth are not moved relative to each other.

In some embodiments the treatment planning and the occlusion simulation are performed in an iterative manner, whereby each time a change is made in the treatment plan, the occlusion is simulated.

In some embodiments constraints of movement of one or more teeth are implemented.

In some embodiments modelling of orthodontic appliances is configured to be performed.

In some embodiments the patient's occlusion with the modelled appliances is configured to be simulated.

In some embodiments the modelling of the appliances are performed in an iterative manner, whereby for each change in the appliances, the occlusion is simulated.

In some embodiments appliances for the upper jaw and appliances for the lower jaw are modelled in parallel.

In some embodiment the appliances are configured to be braces, brackets, splints, retainers, archwires, aligners, and/or shells.

In some embodiments the appliances are configured to retain teeth in their position.

In some embodiments the appliances are configured to hinder the patient from grinding his teeth.

In some embodiments the appliances are configured to hinder the patient from snoring in his sleep.

In some embodiments the appliances are configured to be comfortable to wear for the patient.

In some embodiments occlusion of the present set of teeth is simulated, and the one or more designed appliances is/are optionally included in the simulation.

In some embodiments the one or more designed appliances are modified based on the occlusion simulation.

In some embodiments the one or more appliances are modified with respect to position and/or anatomy.

In some embodiments the virtual articulator is configured to maintain the upper and lower models in an open position.

It is an advantage that the teeth models in the virtual articulator can be held in an open position because for some orthodontic cases appliances should be designed which keeps the upper and lower jaw in an open position with a distance to each other such that the bite can be remodeled. When keeping the models in an open position in the virtual articulator these appliances for providing a distance between the teeth can be designed. Thus appliance which raised and opens the bite can be designed using the virtual articulator.

It is a further advantage that a restoration can also be designed when the virtual articulator is configured with the upper and lower model in an open position.

In some embodiments the teeth in the virtual articulator are color coded for indicating contact between teeth.

In some embodiments the timewise sequence of events in the occlusion simulation is registered.

In some embodiments an occlusal compass is generated based on the occlusion simulation.

In some embodiments an occlusal compass generated by real dynamic occlusion in the patient's mouth is transferred to the dynamic virtual articulator.

In some embodiments the occlusal compass indicates movements in the following directions:
protrusion;
retrusion;
laterotrusion to the right;
laterotrusion to the left;
mediotrusion to the right;
mediotrusion to the left;
latero-re surtrusion to the right;
latero-re surtrusion to the left.

In some embodiments the occlusal compass indicates the different movement directions with different colors on the teeth.

An occlusal compass for a cusp is a three-dimensional pattern, which is a summation of a cusp's movement in all three planes of motion. The occlusal compass has elevations and depressions, and for any given cusp it may vary from that of any other cusp as a function of its relationship to the mandibular rotation centers. It is thus an advantage to use occlusal compasses, since there is not one type of occlusal morphology suitable for every patient. Thus using occlusal compasses, morphology and functional restorations may be designed to fit the specific patient.

In some embodiments the occlusal contact forces in one or more parts on the teeth is registered.

In some embodiments the occlusal contact forces over time in one or more parts of the teeth are registered.

In some embodiments the occlusal contact forces are registered by means of an electronic sensor for measuring the occlusal contact forces.

In some embodiments the registered occlusal contact forces are transferred to the dynamic virtual articulator.

It is an advantage to use an electronic sensor for measuring the occlusal contact forces, e.g. a T-Scan III® from Tekscan, since hereby the occlusal contact forces can be determined in the mouth of the patient and transferred electronically to the dynamic virtual articulator for use in the simulation of dynamic occlusion. The dynamic virtual articulation and simulation of the patient's bite may be enhanced using the occlusal contact force measurement.

In some embodiments the force of occlusion is simulated.

The simulation is performed in the software, using e.g. the virtual articulator.

In some embodiments the registered and/or simulated force of occlusion is visualized.

In some embodiments a biophysical model of the functionality of the jaws and the force of the occlusion is generated.

In some embodiments data from a force measurement is recorded by means of an electronic component in the patient's mouth.

In some embodiments the date from the force measurement is transferred into and overlaid in the dynamic virtual articulator.

In some embodiments a CT scan of the patient's mouth is generated, and a virtual 3D model of the patient's mouth is automatically generated based on the scan, and occlusion is configured to be simulated based on the 3D CT model.

In some embodiments the positions and/or sizes of the jaw muscles are derived from the CT scan, and based on the muscles the strength of the occlusion is configured to be simulated.

In some embodiments a CT scan of at least part of the patient's skull is transferred into the virtual articulator.

In some embodiments constraints to the simulation of the occlusion are derived from the CT scan.

In some embodiments one or more tooth roots are visual on the CT scan, and the position of the tooth roots are used to simulate movement of teeth.

In some embodiments a 2D image of the patient is transferred into the virtual articulator.

In some embodiments a weight assigned to a tooth determines its functionality importance in guiding the occlusion of the patient.

In some embodiments a high weight signifies that the tooth is important for guiding the occlusion.

In some embodiments a low weight signifies that the tooth is not important for guiding the occlusion.

In some embodiments a medium weight signifies that tooth's importance for guiding the occlusion is medium.

In some embodiments the central teeth and/or the canines is/are assigned a high weight.

It is an advantage to assign a high weight to the centrals and/or to the canines in the upper and/or lower jaw, since these teeth often are the most important teeth for guiding the occlusion, since they are the longest teeth. Thus if these teeth are important for guiding the occlusion, they should preferably not be moved, shortened, removed, restored etc., since this could influence the occlusion negatively.

In some embodiments occlusion of the present set of teeth is simulated, and the one or more designed restorations is/are optionally included in the simulation.

In some embodiments the one or more designed restorations are modified based on the occlusion simulation.

In some embodiments the one or more restorations are modified with respect to position and/or anatomy.

In some embodiments the virtual articulator is used for simulating occlusion when designing a partial removable prosthesis for a patient.

It is a problem if a restoration becomes too high, such as extending a little above the neighbor teeth, because then it may interrupt the patient's bite and/or easily become broken. Thus it is desired that the restoration on the prepared tooth in the patient's mouth is lower or shorter than the neighbor teeth.

Traditionally, when performing manual modelling of restorations, the dental technician would manually push the prepared tooth a little bit up in the cast model and then make the restoration.

When performing virtual design or modelling of a restoration in software, traditionally the virtual lower model and the virtual upper model will be virtually moved such that they have an overlap, and the restoration is then designed. This is done because the models are virtual models and therefore can penetrate each other in the virtual 3D space in traditional software modeling.

In some embodiments a prepared tooth in the virtual 3D model is displaced to be arranged with a distance from its actual position relative to its neighbor teeth and/or its position in the gingival before designing the restoration for the prepared tooth.

It is an advantage because when a restoration is designed on the displaced prepared tooth, the restoration can be designed to be level with the neighbor teeth, and when the prepared tooth with restoration is again arranged in its actual position in the virtual 3D model, the restoration will be lower or shorter than the neighbor teeth, and the real restoration on the real prepared tooth in the patient's mouth will therefore also be lower or shorter than the real neighbor teeth and hereby the restoration, which may be more fragile than the real teeth, may be better protected against collisions in the mouth with other teeth or food stuff etc. The distance the prepared tooth is displaced may be in the range of millimeters, micrometers etc. The distance may be a vertical distance.

According to the present embodiment, the virtual modelling is performed in a way similar to the traditional manual work, since the prepared tooth is displaced instead of moving models to be overlapping.

It is an advantage that the restoration can be designed to have an interocclusal distance, such as an extended interocclusal distance instead of being designed to be in contact. The interocclusal distance is defined as the distance between the occlusal surfaces of the teeth in the lower and upper mouth, and thus in this connection the interocclusal distance may be defined as the distance between the restoration and the antagonist teeth.

In some embodiments a gingival part in a position of a missing tooth in the virtual 3D model is displaced to be arranged with a distance from its actual position before designing an implant restoration or a pontic in a bridge for the position of the missing tooth.

It is an advantage that the implant, implant crown, pontic etc. is lower than the neighbor teeth for protecting the implant restoration, the pontic restoration etc. against collisions etc.

In some embodiments one or more contact criteria for occlusion is defined and used in simulation of occlusion.

In some embodiments the one or more contact criteria comprises:
 specific teeth must be in contact with each other;
 a maximum number of teeth must be in contact;
 a maximum area of the teeth surfaces must be in contact;
 specific teeth must not be in contact;
 a maximum number of contact points must be obtained;
 contact points must be evenly spatially distributed over the surface of teeth; and/or
 the contact points between teeth must not be disclosed more than a certain distance during certain dynamic occlusion movements.

The contact criteria may be used to estimate, correct, and/or improve the virtual articulator model, e.g. the geometrical and/or physiological model of the virtual articulator.

Parameters of the virtual articulator model may be automatically optimized, adjusted, corrected, defined, determined etc. by simulating the movement of the jaws in the articulator, and the simulation may be based on the virtual articulator model.

For example the operator may often wish to optimize the condyle inclination, since this an important parameter for many cases.

By improving the occlusion by means of parameters and contact criteria, the quality of the occlusion will be improved in relation to the patient's real, physiologic occlusion.

For example if there are mistakes or faults in the data of the patient's occlusion taken from the mechanical articulator, the facebow etc., then the occlusion can be corrected using parameters and contact criteria.

Disclosed is also a system for using a dynamic virtual articulator for simulating occlusion of teeth, when performing computer-aided designing of one or more dental restorations for a patient, where the system comprises:

means for providing the virtual articulator comprising a virtual three-dimensional teeth model comprising the upper jaw, defined as the virtual upper jaw, and a virtual three-dimensional teeth model comprising the lower jaw, defined as the virtual lower jaw, resembling the upper jaw and lower jaw, respectively, of the patient's mouth;

means for providing movement of the virtual upper jaw and the virtual lower jaw relative to each other for simulating dynamic occlusion, whereby collisions between teeth in the virtual upper and virtual lower jaw occur;

wherein the system further comprises:

means for providing that the teeth in the virtual upper jaw and virtual lower jaw are blocked from penetrating each other's virtual surfaces in the collisions.

Disclosed is also a system for using a dynamic virtual articulator for simulating occlusion of teeth, when performing computer-aided orthodontic treatment planning for a patient, where the system comprises:

means for providing the virtual articulator comprising a virtual three-dimensional teeth model comprising the upper jaw, defined as the virtual upper jaw, and a virtual three-dimensional teeth model comprising the lower jaw, defined as the virtual lower jaw, resembling the upper jaw and lower jaw, respectively, of the patient's mouth;

means for providing movement of the virtual upper jaw and the virtual lower jaw relative to each other for simulating dynamic occlusion, whereby collisions between teeth in the virtual upper and virtual lower jaw occur;

wherein the system further comprises:

means for providing that the teeth in the virtual upper jaw and virtual lower jaw are blocked from penetrating each other's virtual surfaces in the collisions.

Disclosed is also a dental restoration designed according to the present method.

Disclosed is also an orthodontic appliance for use in an orthodontic treatment planning, where the appliance is designed according to the present method.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
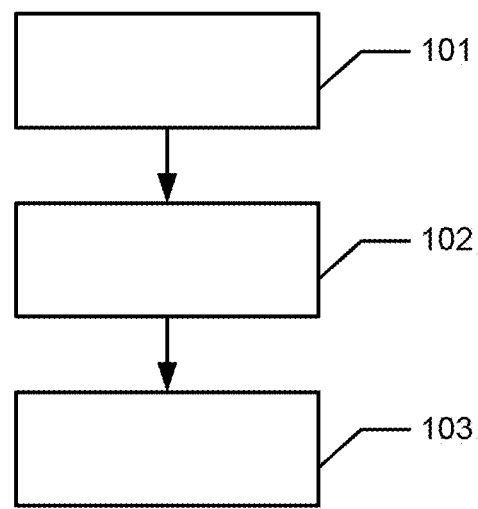
FIG. 1 shows an example of a flow chart of the method.

FIG. 1 shows an example of a flow chart showing the steps of the computer-implemented method of using a dynamic virtual articulator for simulating occlusion of teeth, when performing computer-aided design of one or more dental restorations for a patient.

In step 101 the virtual articulator comprising a virtual three-dimensional model of the upper jaw and a virtual three-dimensional model of the lower jaw resembling the upper jaw and lower jaw, respectively, of the patient's mouth is provided.

In step 102 movement of the virtual upper jaw and the virtual lower jaw relative to each other is provided for simulating dynamic occlusion, whereby collisions between teeth in the virtual upper and virtual lower jaw occur;

In step 103 the teeth in the virtual upper jaw and virtual lower jaw are provided to be blocked from penetrating each other's virtual surfaces in the collisions.

FIG. 2 shows examples virtual articulators.

Figure 2A:
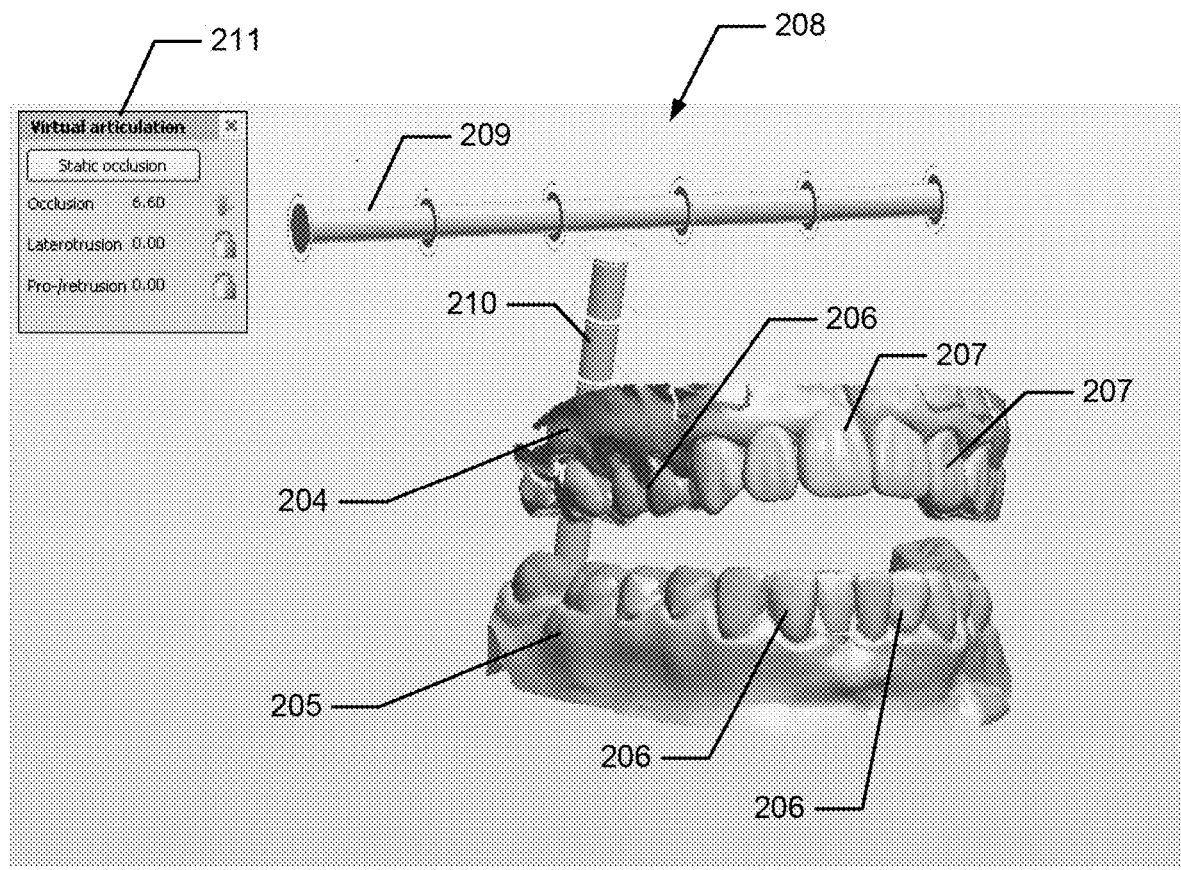
FIG. 2a-2b show examples virtual articulators.

FIG. 2a) shows a virtual upper jaw 204 with teeth 206 and a virtual lower jaw 205 with teeth 206. Six teeth 207 in the upper jaw 204 have been restored, and the virtual articulator 208 are used to simulate the movements of the jaws 204, 205 to test if the restored teeth 207 fit into the mouth of a patient. The virtual articulator 208 is indicated by two axes, an occlusial axis 209 and a laterotrusial-mediotrusial axis 210. The jaws 204, 205 moves up and down along the occlusial axis 209, and the jaws 204, 205 performs forward-sidewards movements to both left and right along the laterotrusial-mediotrusial axis 210. The jaws 204, 205 can also perform protrusion, which is direct forward movement, and retrusion, which is direct backward movement. The axes for these movements are not shown in the figure.

In the figure only movement along the occlusial axis 209 is shown, while there is no movement along the laterotrusial-mediotrusial axis 210 or along the protrusial-retrusial axes (not shown). This is also seen in the window 211 in the upper left of the figure, where the parameter "occlusion" is 6.60 and the parameter "laterotrusion" is 0.00, and the parameter "pro-/retrusion" is also 0.00. The different movement directions possible may be:
protrusion;
retrusion;
laterotrusion to the right;
laterotrusion to the left;
mediotrusion to the right;
mediotrusion to the left;
latero-re surtrusion to the right;
latero-re surtrusion to the left.

Figure 2B:
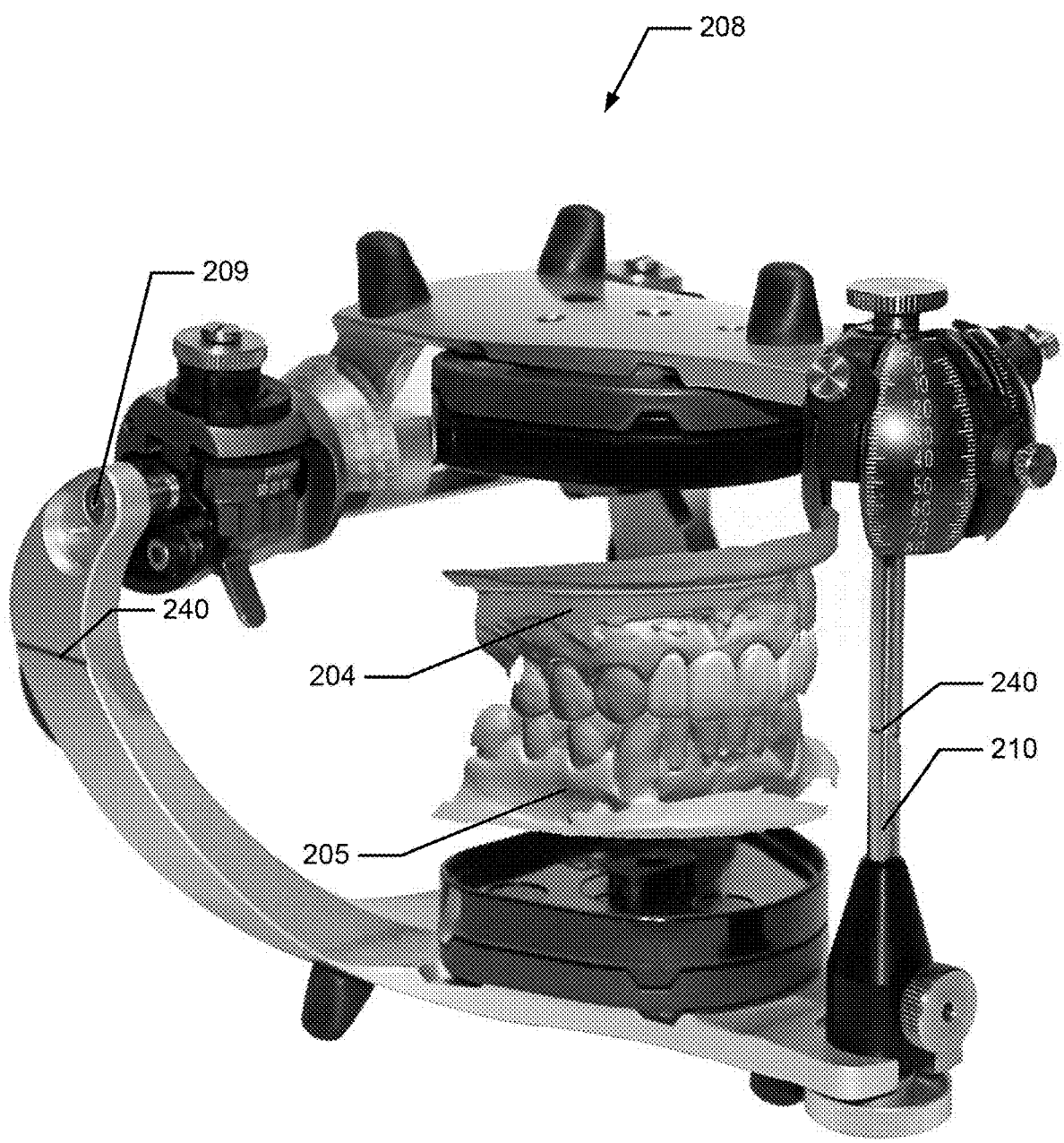

FIG. 2b) shows another virtual articulator 208 with setting opportunities 209, 210 for controlling the movement of the jaws 204, 205 along an occlusial axis, a laterotrusial-mediotrusial axis, a protrusial-retrusial axis etc. The indentations 240 indicate where the dental technician will arrange a default occlusal plane in the form of a rubber band.

FIG. 3 shows an example of movements of the jaws for simulating occlusion.

Both jaws 204, 205 comprise non-modified teeth 206, and the upper jaw 204 also comprises restored teeth 207. The movements are made to simulate, if the restored teeth 207 fit into the mouth.

Figure 3A:
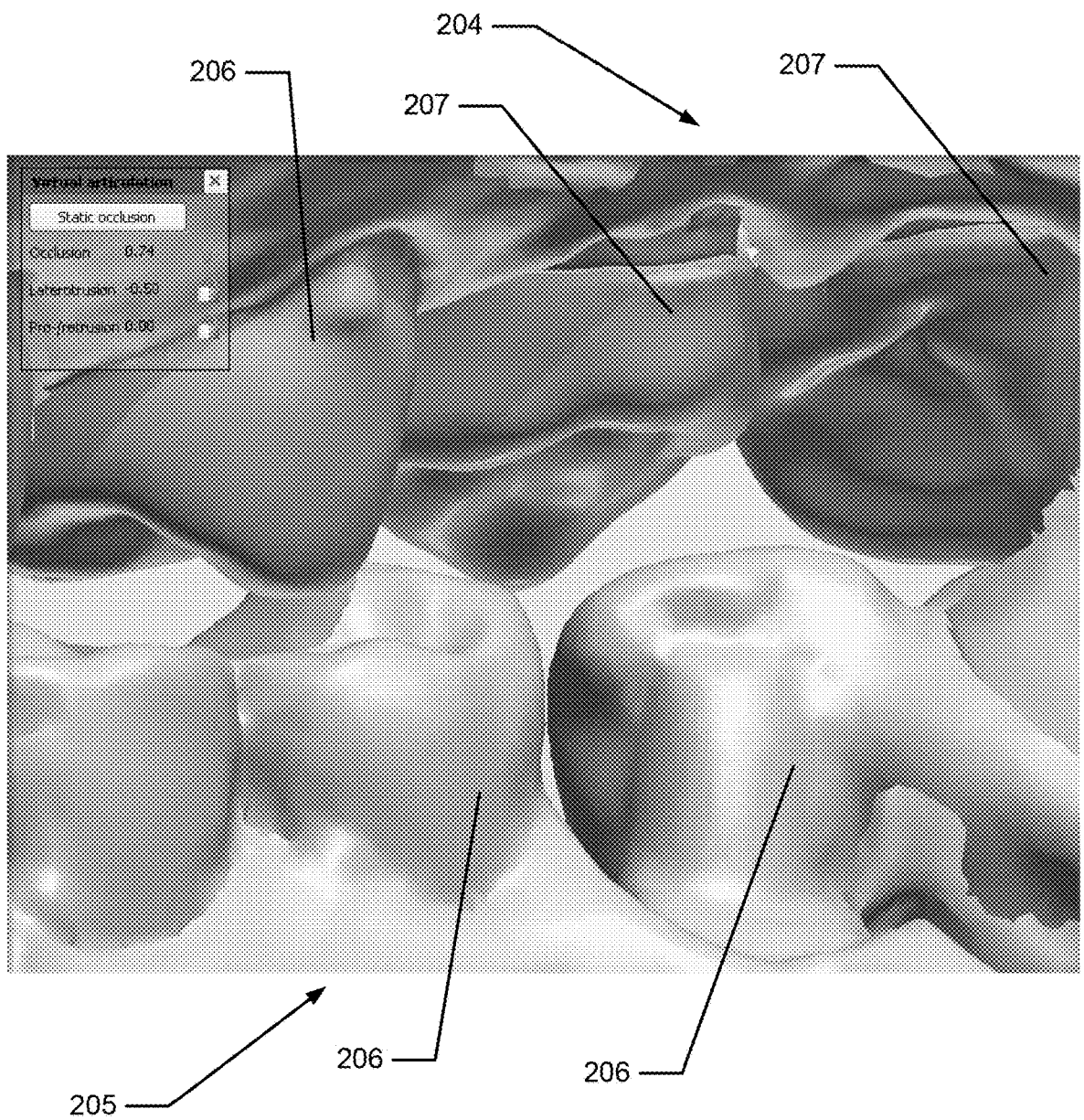
FIG. 3a-3d show an example of movements of the jaws for simulating occlusion.

FIG. 3a) shows the jaws 204, 205 in a first position, where no teeth 206 in the jaws 204, 205 have collided with the restored teeth 207.

Figure 3B:
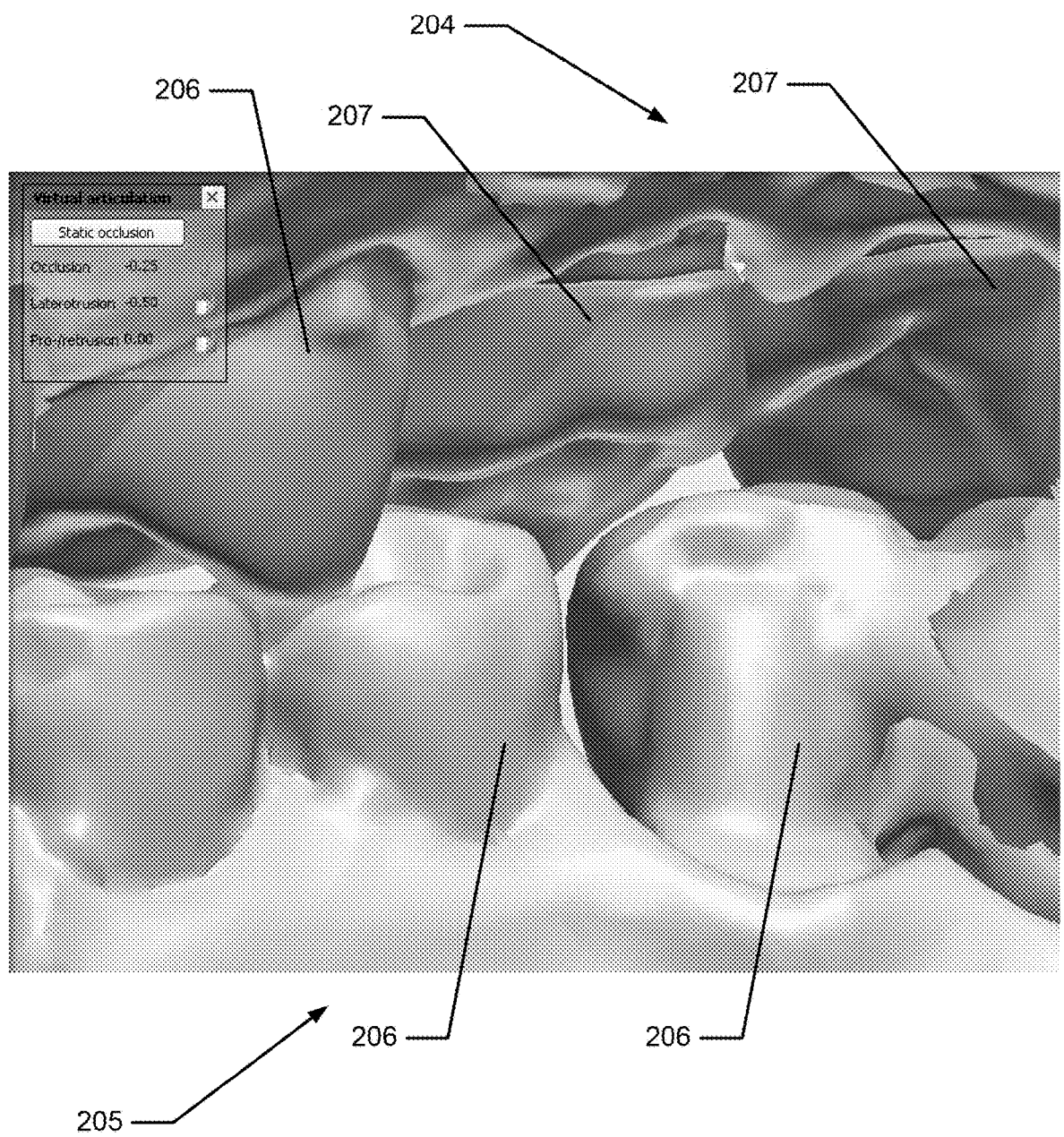

FIG. 3b) shows the jaw 204, 205 in a second position, where the jaw 204, 205 have moved closer to each other, but there is still no collision between any of the teeth 206 or the restored teeth 207.

Figure 3C:
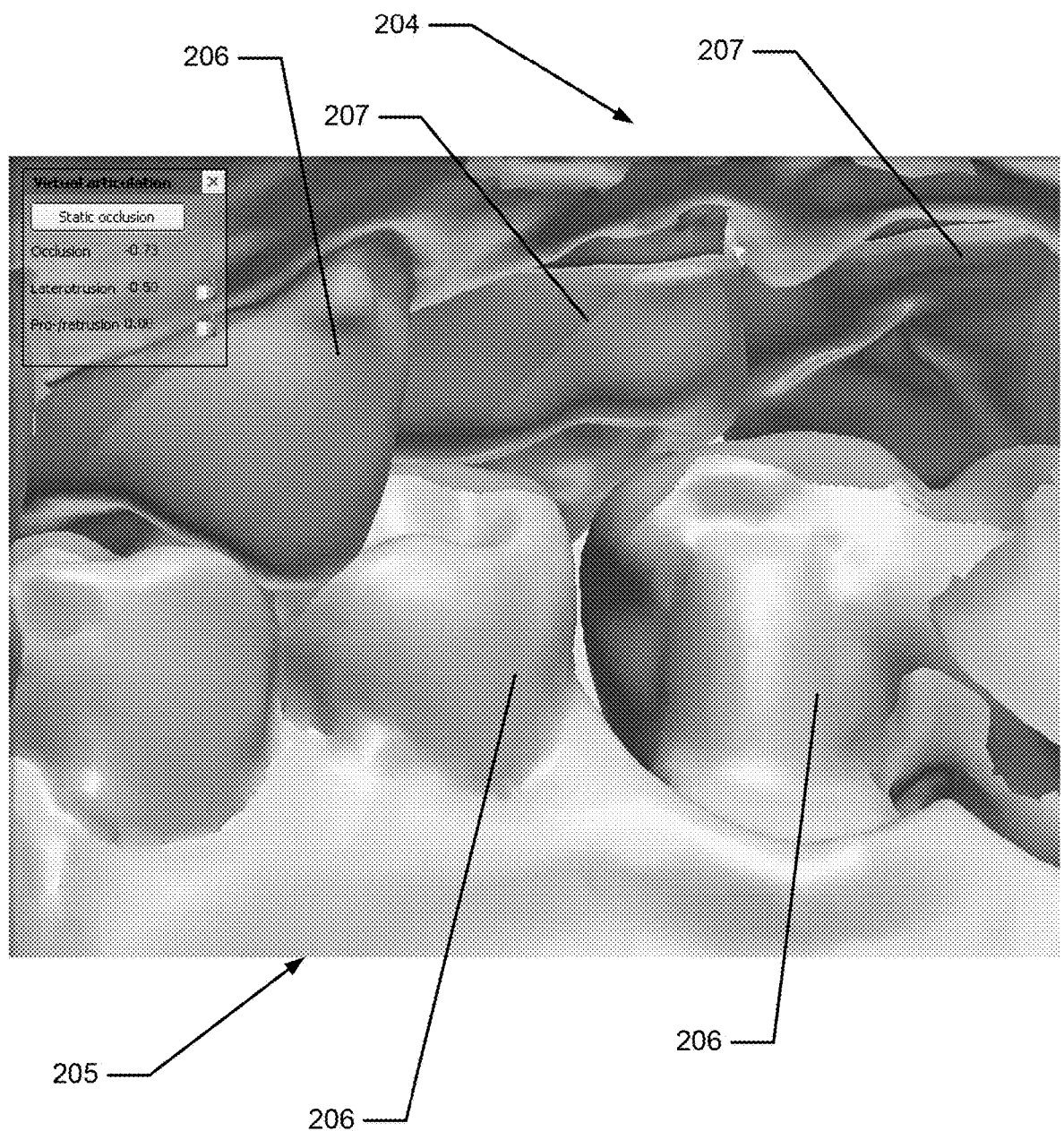

FIG. 3c) shows the jaws 204, 205 in a third position, where the jaw 204, 205 have moved even closer to each other.

Figure 3D:
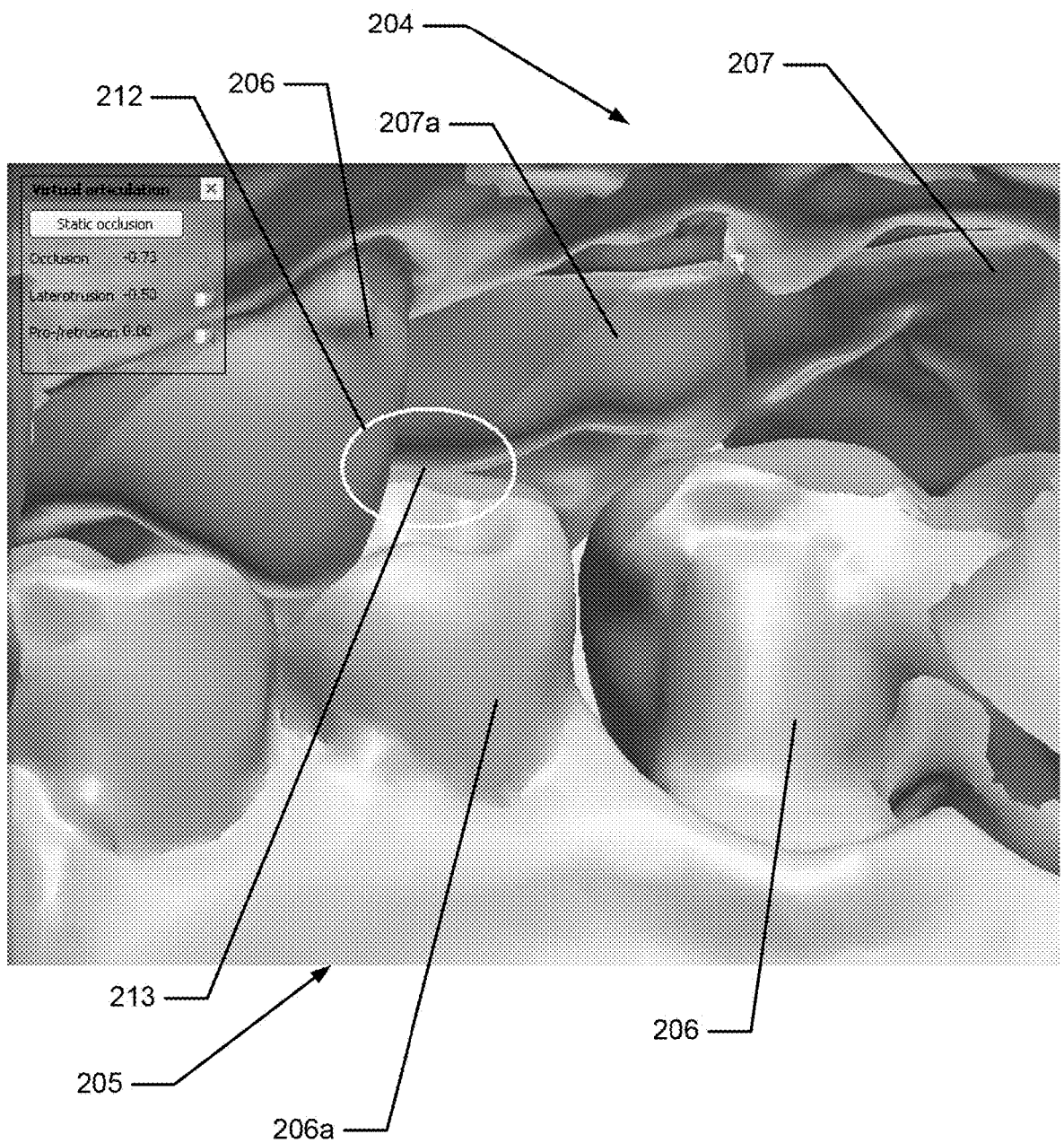

FIG. 3d) shows the jaws 204, 205 in the third position with a circle 212 at a point 213, where the teeth of the jaws 204, 205 have collided. The collision is between a restored tooth 207a in the upper jaw 204 and a tooth 206a in the lower jaw 205.

FIG. 4 shows an example of modelling of a restored tooth.

Figure 4A:
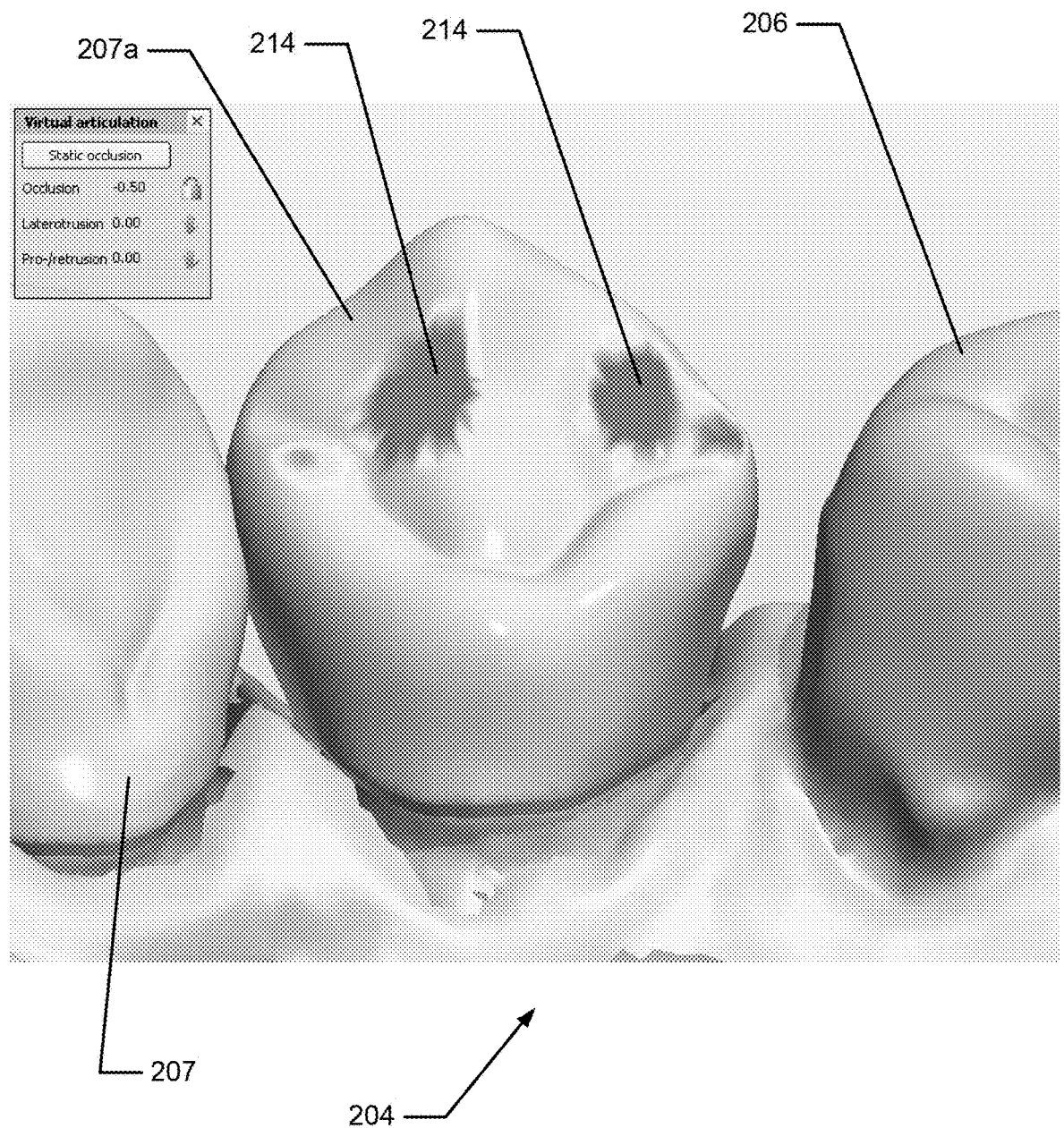
FIG. 4a-4b show an example of modelling of a restored tooth.

FIG. 4a) shows the upper jaw 204, turned around relative to the preceding figures, with the restored tooth 207a, another restored tooth 207 and an un-modified tooth 206. The restored tooth 207a has collided with a tooth in the lower jaw, as shown in FIG. 3d), and the collision points 214 are indicated on the tooth 207a. The shades of the collision points may indicate the penetration depth or the pressure with which the tooth 207a and the tooth in the lower jaw collided. Thus the shades from light to dark indicate a depth mapping or pressure mapping, where light shade indicates low depth or light pressure and dark shade indicates large depth or hard pressure.

It may be so that the teeth are not completely rigid, but are a little bit soft, and the teeth may therefore give or deform a little when colliding with each other. Thus it may be so that the virtual teeth are not defined to be completely rigid, but are a little bit soft or resilient, and the virtual teeth may therefore give or deform a little when virtually colliding with each other.

Figure 4B:
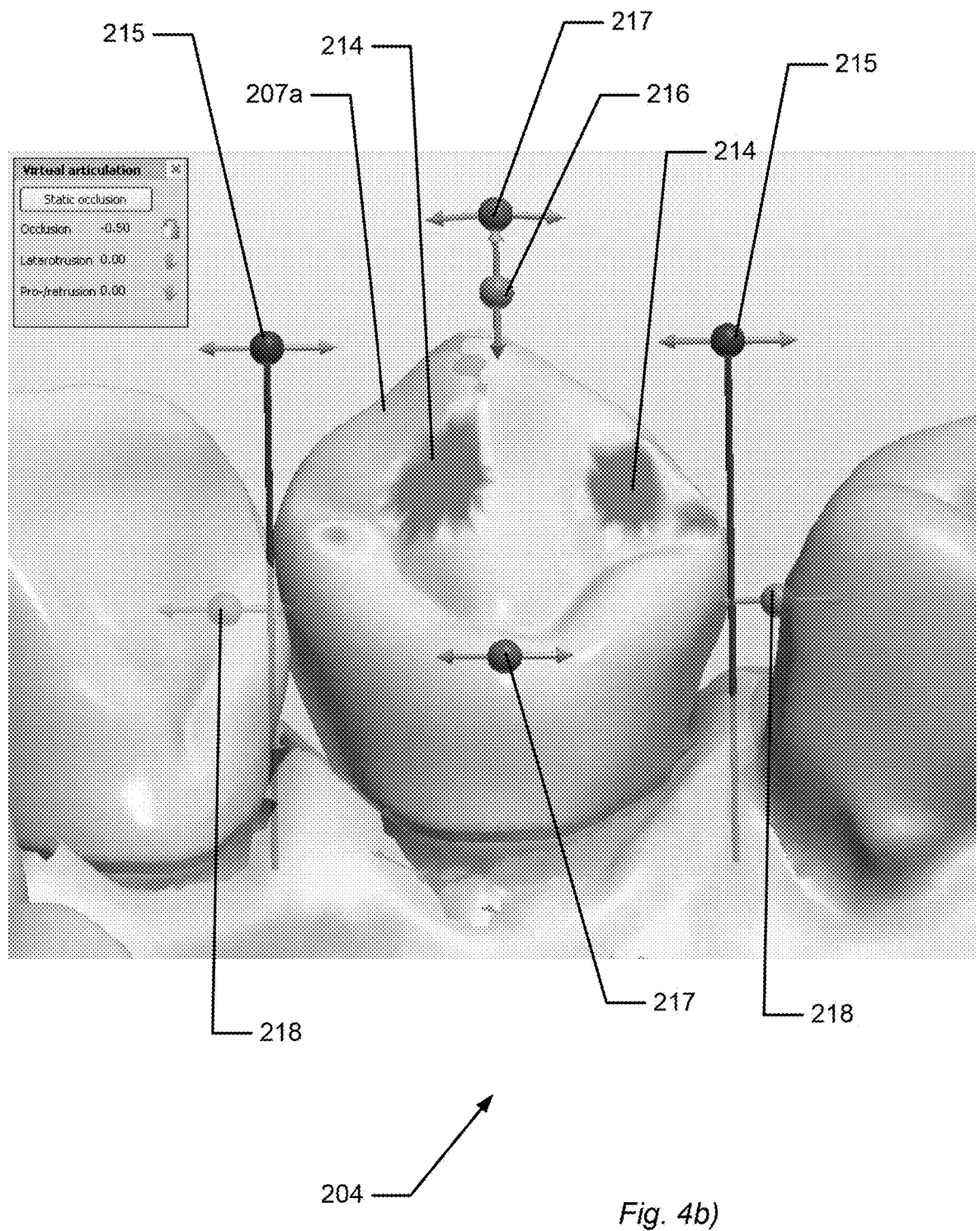

FIG. 4b) shows the same as FIG. 4a) and also tools for modelling the restored tooth 207a. Since the tooth 207a collided with a tooth in the lower jaw, see FIG. 3d), the restored 207a) can be modelled such that it will not collide with the tooth in the lower jaw. The tooth 207a can be modelled by dragging or morphing it to the left or right side indicated by the tools 215, and by dragging the tooth 207a up and down indicated by the tool 216. The tooth 207a can also be modelled by dragging or morphing points on it to the left side or right side indicated by tools 217, and by dragging or morphing it to the neighbor teeth indicated by tools 218.

While morphing or dragging the tooth 207a, the collision points 214 will change corresponding to these shape changes of the tooth, and the tooth 207a can then be modelled such that there will no longer be any collision with the teeth in the lower jaw, and the collisions points 214 will then disappear from the tooth 207a indicating that the tooth 207a has been modelled to avoid collisions with opposing teeth.

Figure 5:
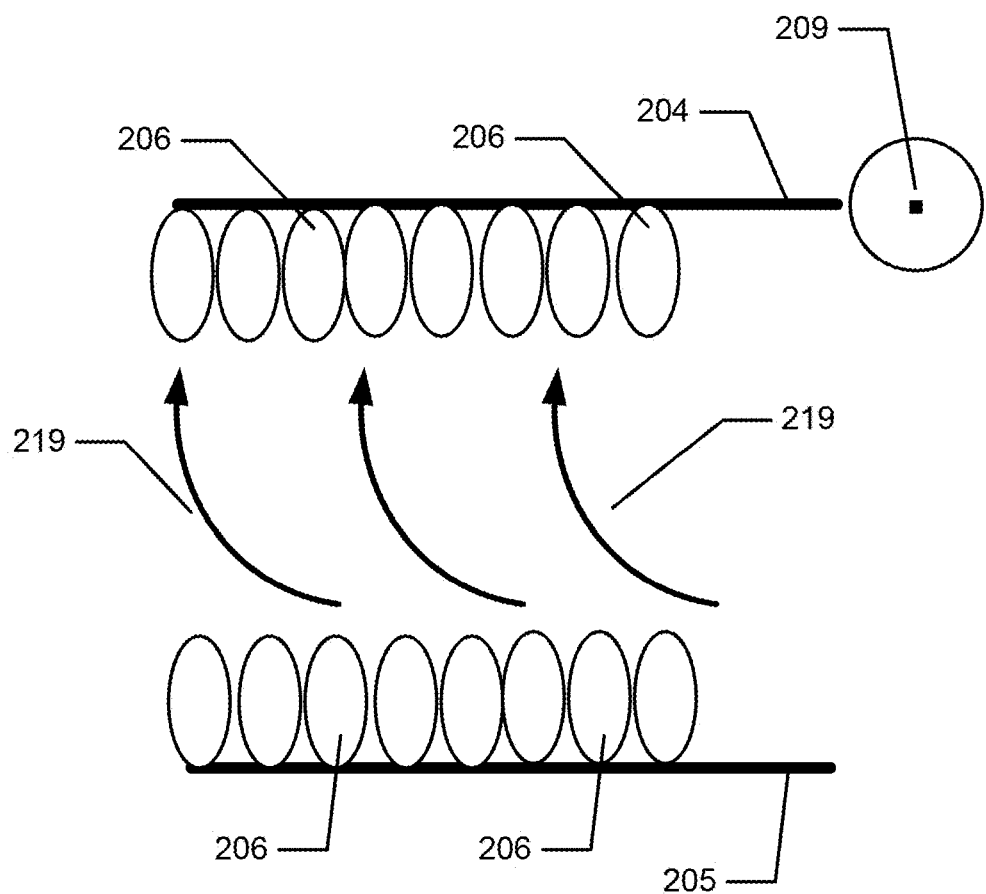
FIG. 5 shows a schematic example of movement along the occlusial axis.

FIG. 5 shows a schematic example of movement along the occlusial axis.

The figure shows the upper jaw 204 with teeth 206 and the lower jaw 205 with teeth 206. Some of these teeth may be restored teeth, and therefore the occlusion may be tested.

The occlusial axis 209 is indicated, and the upper jaw 204 is shown to be fixed to the occlusial axis. The lower jaw 205 can move relative to the upper jaw 204 and therefore the lower jaw can rotate around the occlusial axis 209.

Thus the virtual articulator performs collision test and evaluate the response along the occlusial axis 209, i.e. for any given configuration of the other degrees of freedom, i.e. the other axes, see FIG. 2, and thereby finding the first position on the occlusial axis for which the two jaw models are in contact. This reduces the dimensionality of the calculation problem and allows for the use of more specialized search structures, which are aimed at calculating the first point of intersection with a 3D model along a given circular path 219 around the static rotation axis 209 of occlusion. Thus for each motion step along one of the other axes, i.e. for each degrees of freedom, it may be calculated when and at which points the teeth 206 in the jaws 204, 205 will collide along the occlusial axis 209.

Figure 6:
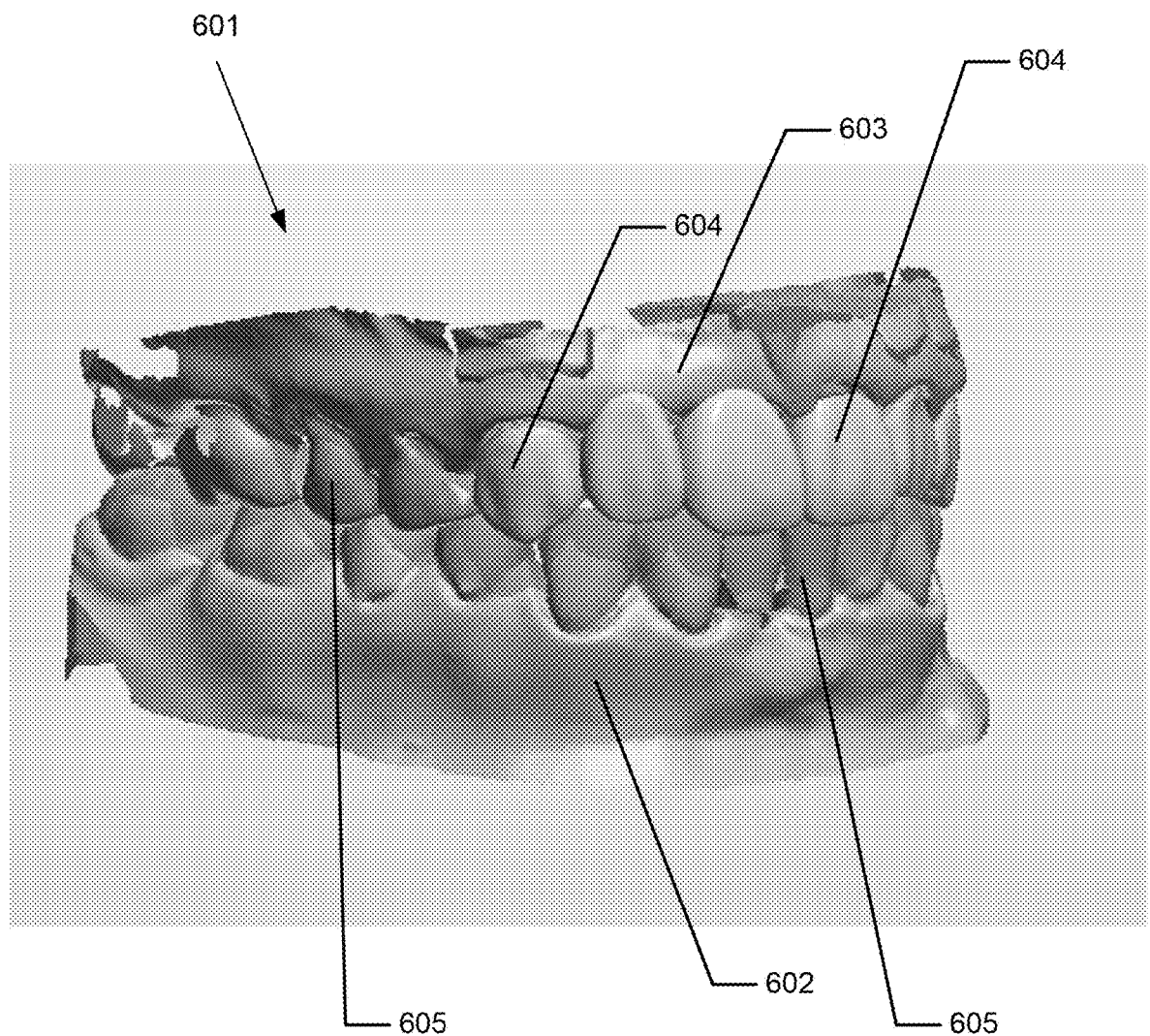
FIG. 6 shows an example of a virtual model of a set of teeth.

FIG. 6 shows an example of a virtual model of a set of teeth.

The virtual model 601 of the set of teeth from a patient comprises a virtual lower arch 602 and a virtual upper arch/jaw 603. Six front teeth 604 in the upper arch 603 are marked in a different color than the rest of the teeth 605 of the set of teeth. These six teeth 604 may be teeth which should be or have been restored. The virtual model 601 may be shown in a graphical user interface, in which an operator, such as a dental technician or dentist, can design, simulate and/or model for example restorations for a patient.

Figure 7:
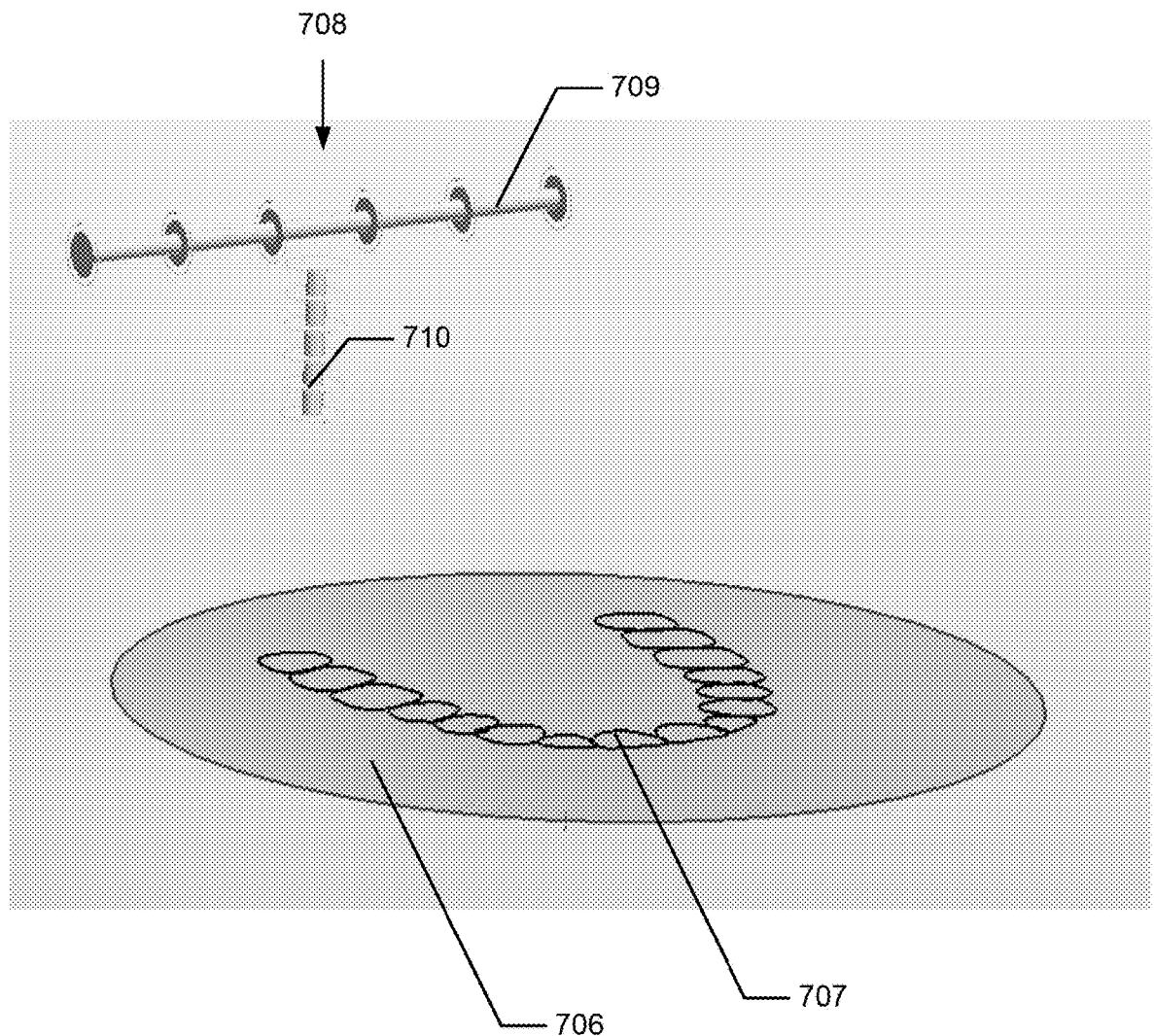
FIG. 7 shows an example of a virtual occlusal plane.

FIG. 7 shows an example of a virtual occlusal plane.

The occlusal plane 706 is visualized as a flat, circular plane, but it is understood that the occlusal plane can have any shape etc. The occlusal plane is a plane passing through the occlusal or biting surfaces of the teeth, and it represents the mean of the curvature of the occlusal surface. Thus the occlusal plane can be flat or undulating following the different heights of the different teeth.

A contour of a standard set of teeth 707 is shown on the occlusal plane 706 for assisting the operator to better match the 3D position of the occlusal surface 706 with a virtual model.

A virtual articulator 708 is indicated by two axes, an occlusial axis 709 and a laterotrusial-mediotrusial axis 710. The upper and lower arches of the virtual model can move up and down along the occlusial axis 709, and the arches can perform forward-sidewards movements to both left and right along the laterotrusial-mediotrusial axis 710. The arches can also perform protrusion, which is direct forward movement, and retrusion, which is direct backward movement. The axes for these movements are not shown in the figure.

The different movement directions possible may be:
protrusion;
retrusion;
laterotrusion to the right;
laterotrusion to the left;
mediotrusion to the right;
mediotrusion to the left;
latero-re surtrusion to the right;
latero-re surtrusion to the left.

Figure 8:
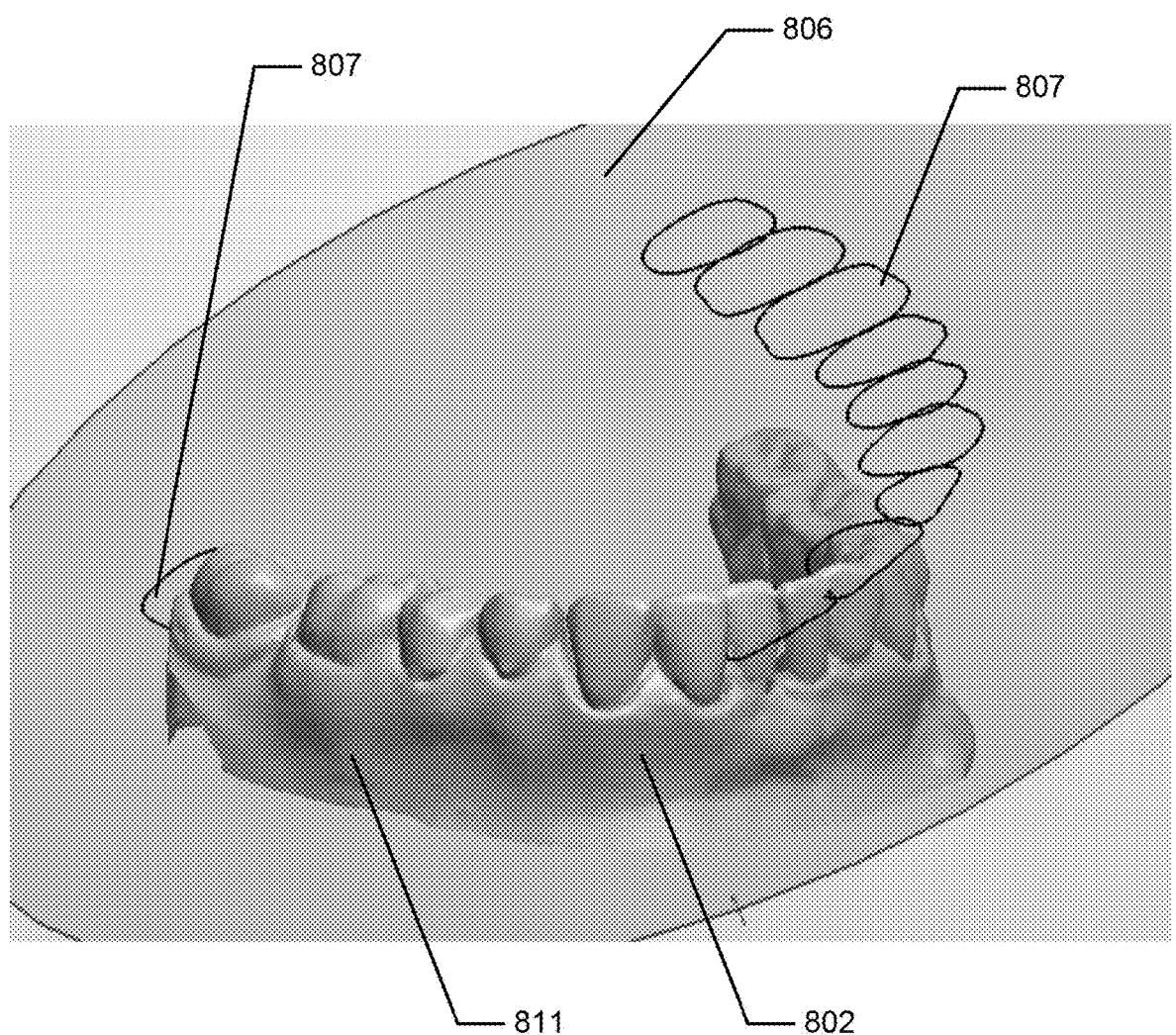
FIG. 8 shows a first example of a virtual occlusal plane and a virtual model before they are adjusted relative to each other's positions.

FIG. 8 shows a first example of a virtual occlusal plane and a virtual model before they are adjusted relative to each other's positions.

The occlusal plane 806 with the standard set of teeth 807 and the virtual model of the lower arch 802 are shown together. The occlusal plane 806 is shown to be inclined relative to the virtual model of the lower arch 802, and the occlusal plane 806 and the virtual model of the lower arch 802 are intersecting each other as seen by the intersection line 811.

Figure 9:
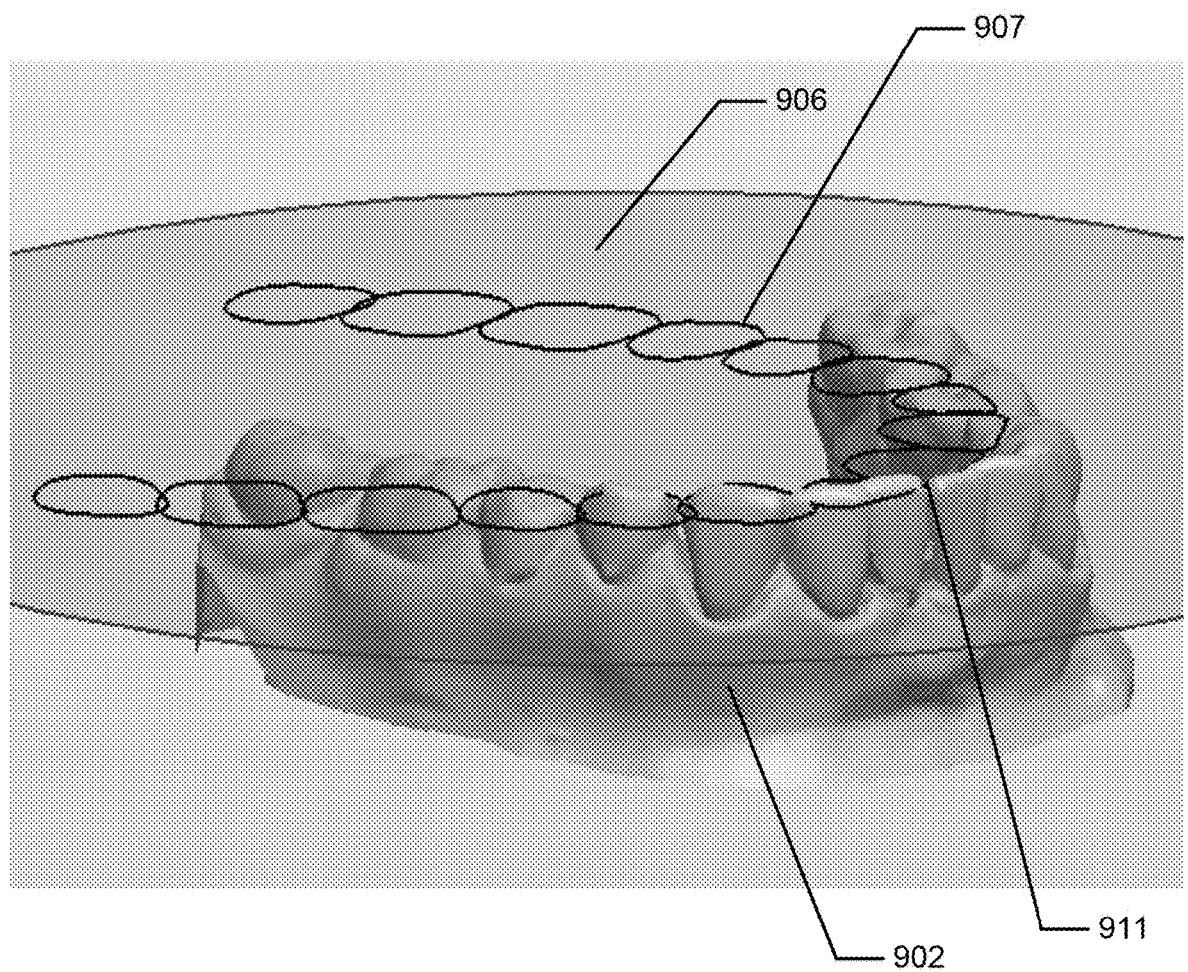
FIG. 9 shows a second example of a virtual occlusal plane and a virtual model while they are adjusted relative to each other's positions.

FIG. 9 shows a second example of a virtual occlusal plane and a virtual model while they are adjusted relative to each other's positions.

The occlusal plane 906 with the standard set of teeth 907 and the virtual model of the lower arch 902 are shown together. The occlusal plane 906 and the virtual model of the lower arch 902 are nearly aligned as their inclinations are the same or almost the same, but the occlusal plane 906 and the virtual model of the lower arch 902 are still intersecting each other a little bit as seen by the intersection line 911 because some of the teeth of the lower arch 902 are a little bit higher than the vertical position of the occlusal plane 906. The occlusal plane 906 and the lower arch 902 are not aligned horizontally yet, because the standard set of teeth 907 on the occlusal plane 906 are not overlapping with the teeth of the lower arch 902.

Figure 10:
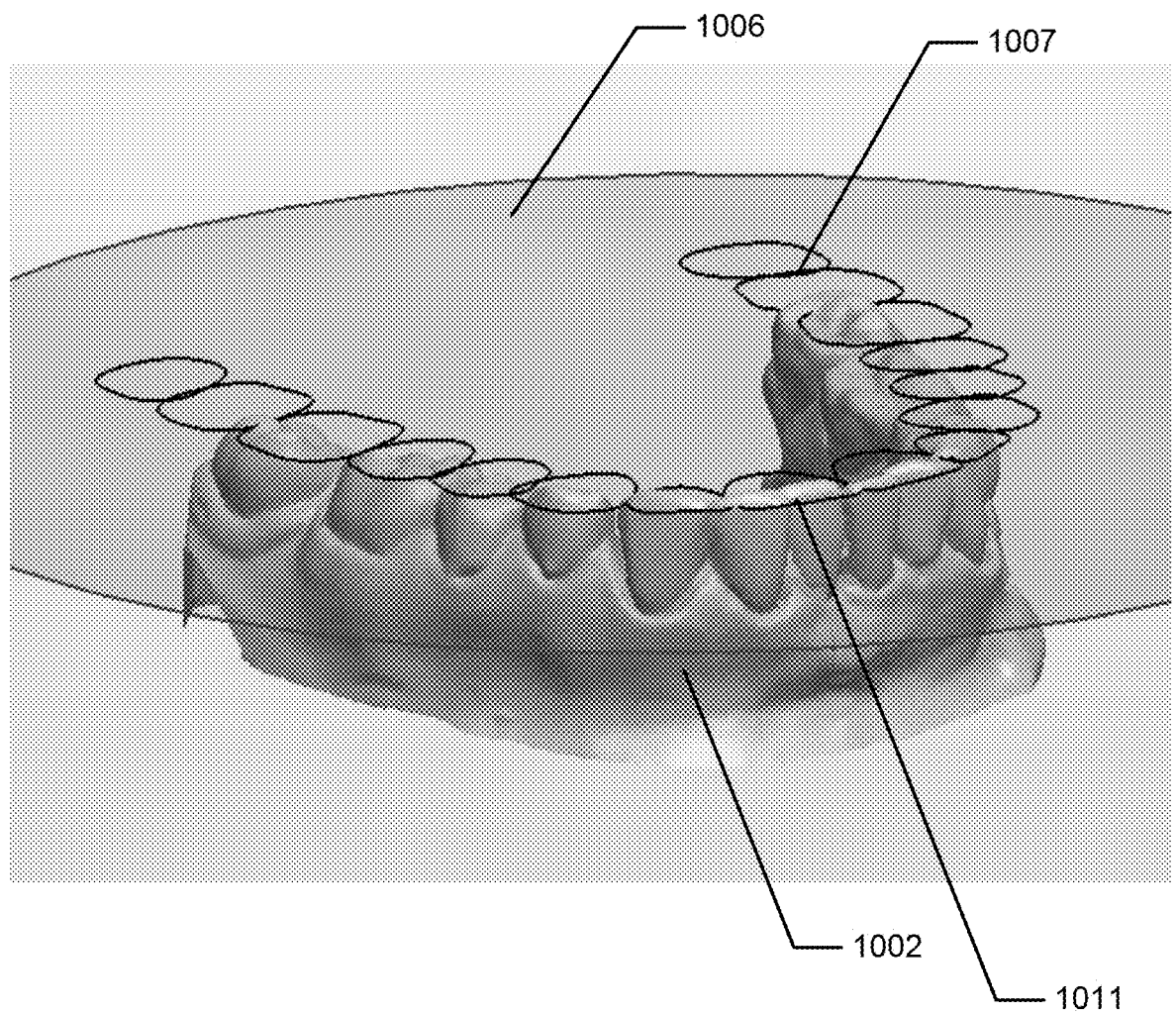
FIG. 10 shows an example of a virtual occlusal plane and a virtual model after they are adjusted relative to each other's positions.

FIG. 10 shows an example of a virtual occlusal plane and a virtual model after they are adjusted relative to each other's positions.

The occlusal plane 1006 with the standard set of teeth 1007 and the virtual model of the lower arch 1002 are shown together. The occlusal plane 1006 and the virtual model of the lower arch 1002 are aligned as their inclinations are the same, and the occlusal plane 1006 and the virtual model of the lower arch 1002 are still intersecting each other a little bit as seen by the intersection line 1011 because some of the teeth of the lower arch 1002 are a little bit higher than the vertical position of the occlusal plane 1006. The occlusal plane 1006 and the lower arch 1002 are aligned horizontally, because the standard set of teeth 1007 on the occlusal plane 1006 are overlapping with the teeth of the lower arch 1002. The alignment may be a 3-point alignment, i.e. using three points for performed the alignment.

Figure 11:
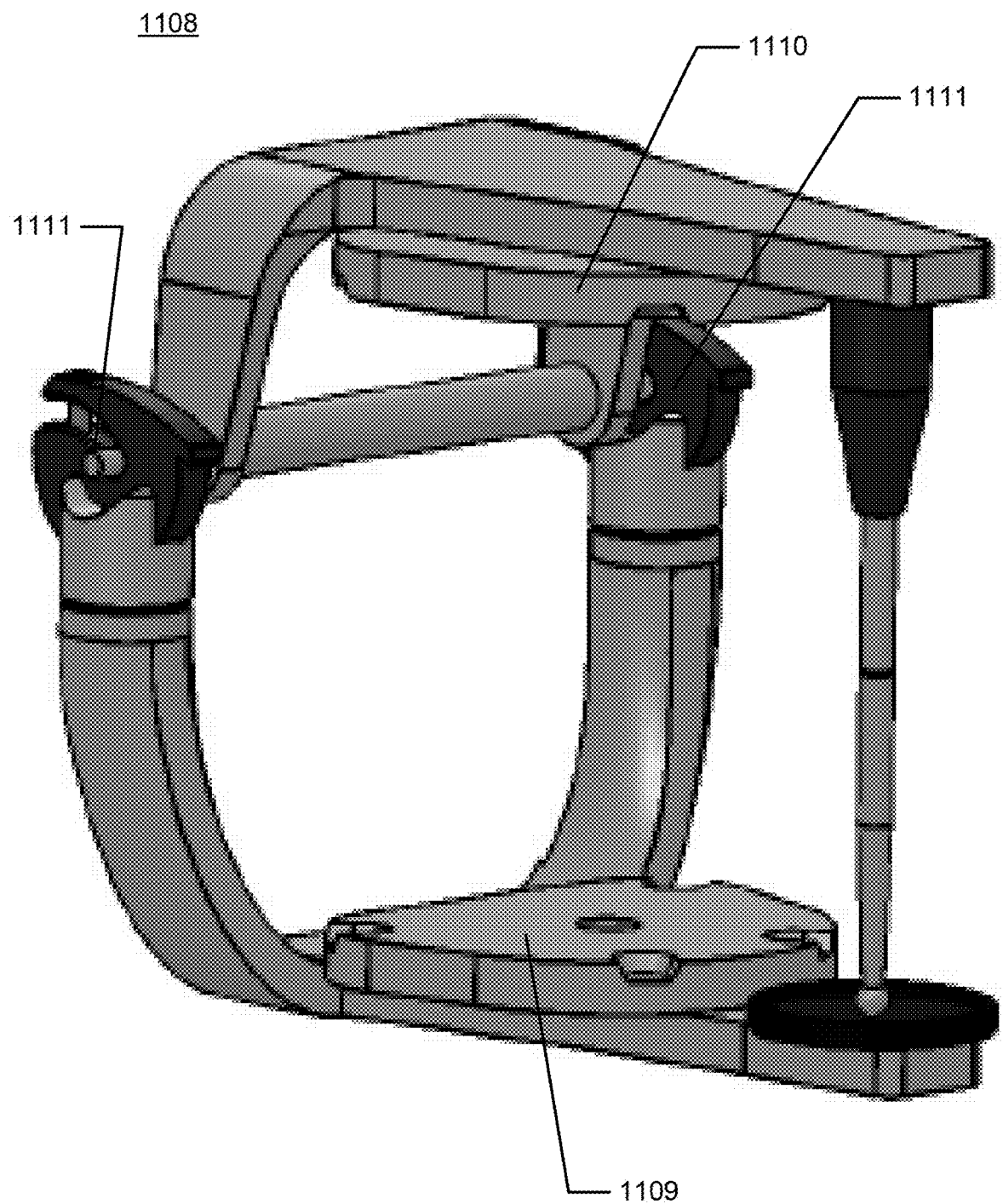
FIG. 11 shows an example of a virtual articulator.

FIG. 11 shows an example of a virtual articulator.

The virtual articulator 1108 is a virtual version of a physical, mechanical device used in dentistry to which casts of the upper and lower teeth are fixed and reproduces recorded positions of the lower teeth in relation to the upper teeth. An articulator can be adjustable in one or more of the following areas: condylar angle, Bennett side-shift, incisal and cuspid guidance, and shape of the glenoid fossae and eminintiae. An articulator may reproduce normal lower movements during chewing. An articulator may be adjusted to accommodate the many movements and positions of the lower teeth in relation to the upper teeth as recorded in the mouth. Thus the virtual articulator may perform all the movements etc. as the mechanical articulator.

The virtual articulator 1108 comprises a bottom base 1109 onto which the virtual model of the lower teeth or lower jaw is adapted to be arranged, a top base 1110 onto which the virtual model of the upper teeth or upper jaw is adapted to be arranged. The different virtual joints, slides or setting means 1111 indicates the joints, slides and other settings of a mechanical articulator where the different areas mentioned above can be adjusted to the features of a specific patient.

Figure 12:
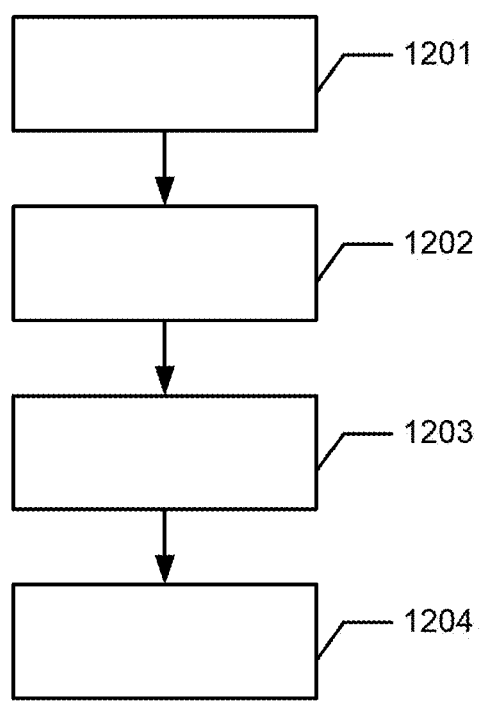
FIG. 12 shows an example of a flow chart of an embodiment of the invention.

FIG. 12 shows an example of a flow chart of an embodiment of the invention.

In step 1201 the movement of the virtual upper jaw and the virtual lower jaw relative to each other is started.

In step 1202 all collisions during the movement of the virtual upper jaw and the virtual lower jaw relative to each other are registered.

In step 1203 the movement of the virtual upper jaw and the virtual lower jaw relative to each other is finished.

In step 1204 each area of the restorations where a collision point was registered is modelled.

FIG. 13 shows an example of a movement of the virtual upper jaw and the virtual lower jaw relative to each other.

Figure 13A:
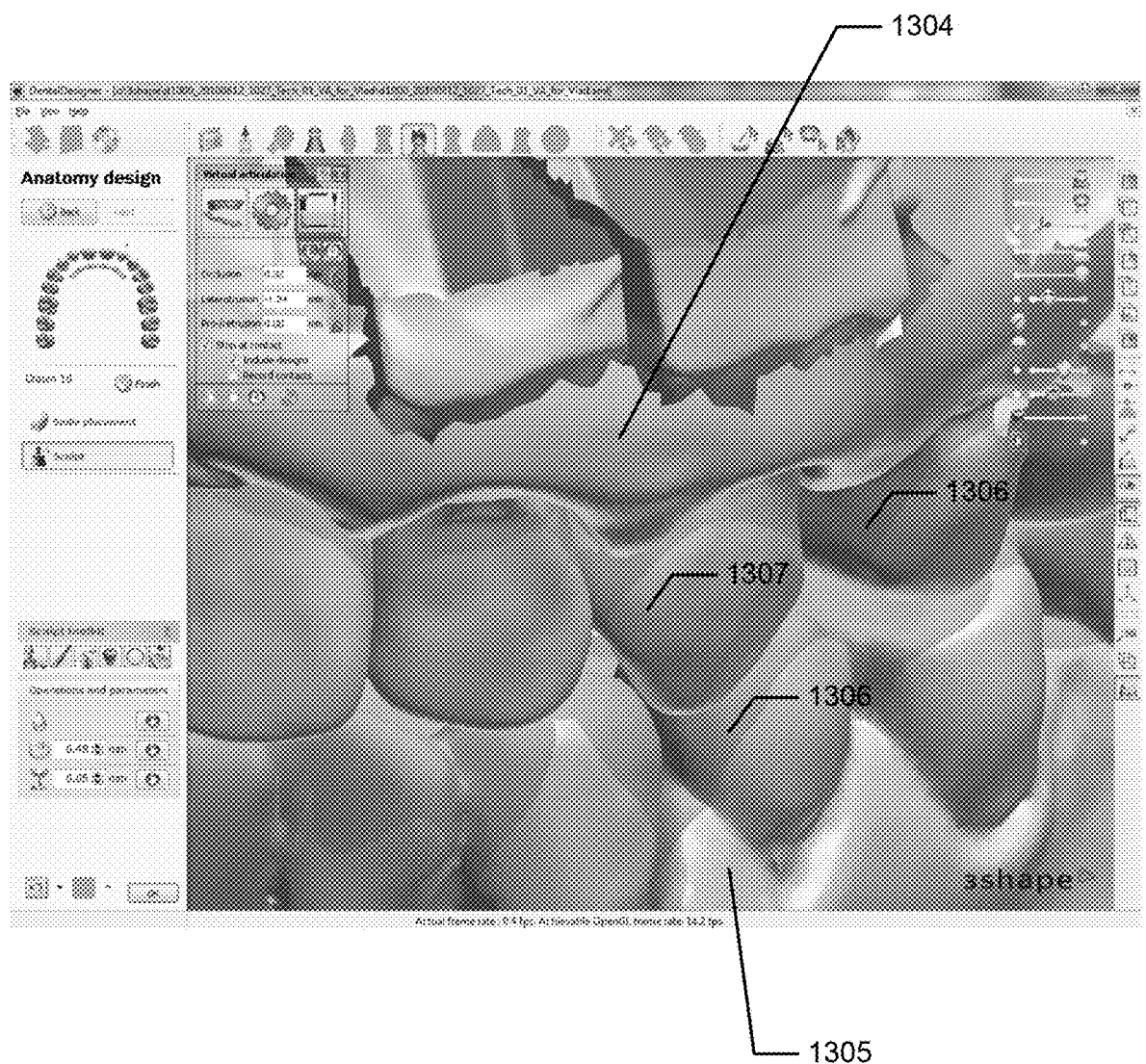
FIG. 13a-13c show an example of a movement of the virtual upper jaw and the virtual lower jaw relative to each other.

FIG. 13a) shows the first position of a movement between the upper jaw 1304 and the lower jaw 1305. Both the lower jaw and the upper jaw comprise teeth 1306, and the upper jaw comprises a number of restorations 1307.

Figure 13B:
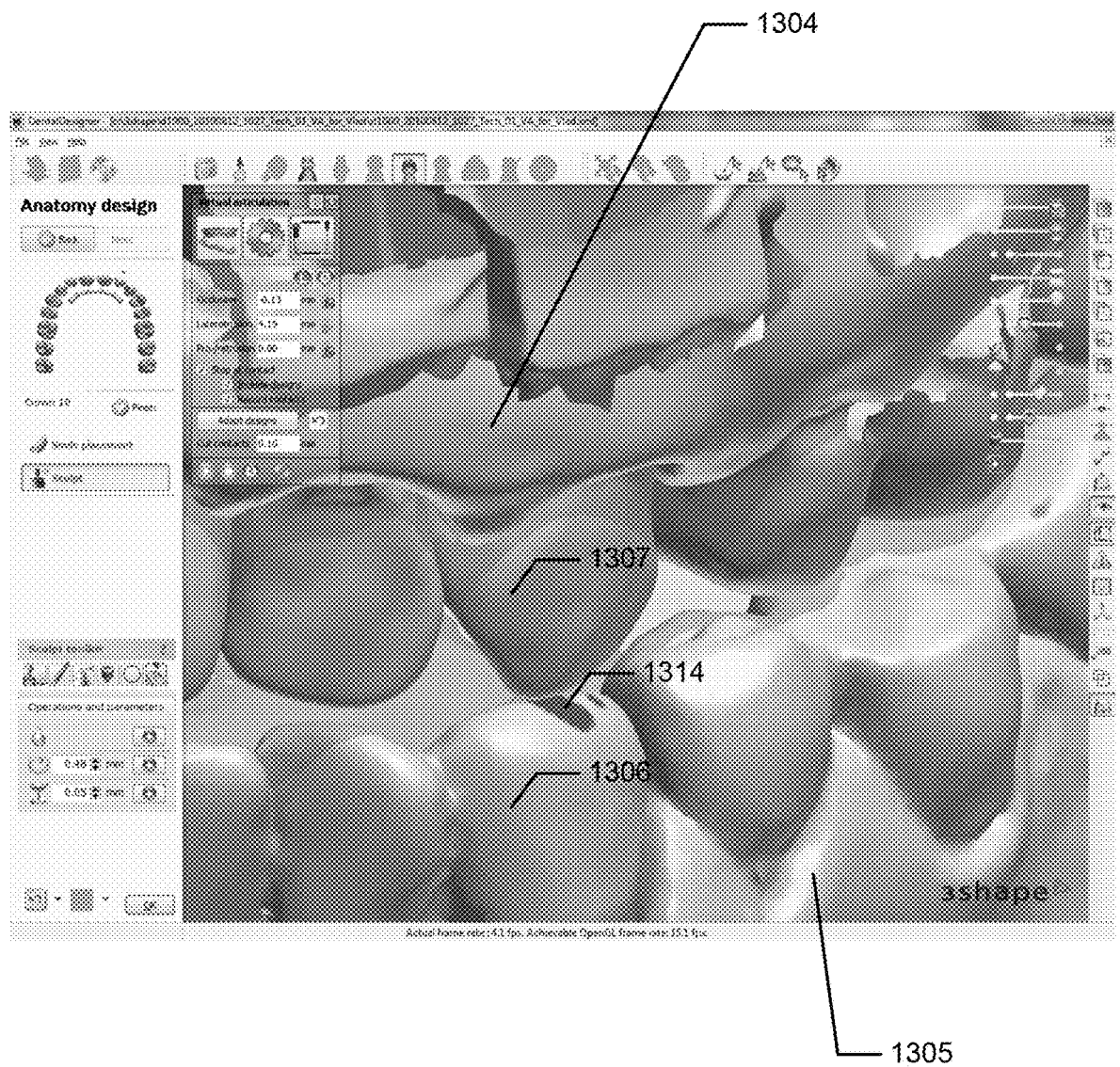

FIG. 13b) shows a position during the movement of the jaws. The upper jaw 1304 is moved relative to the lower jaw 1305, and the restoration 1307 is colliding with a tooth 1306 as seen by the collision point 1314 comprising a contact area.

Figure 13C:
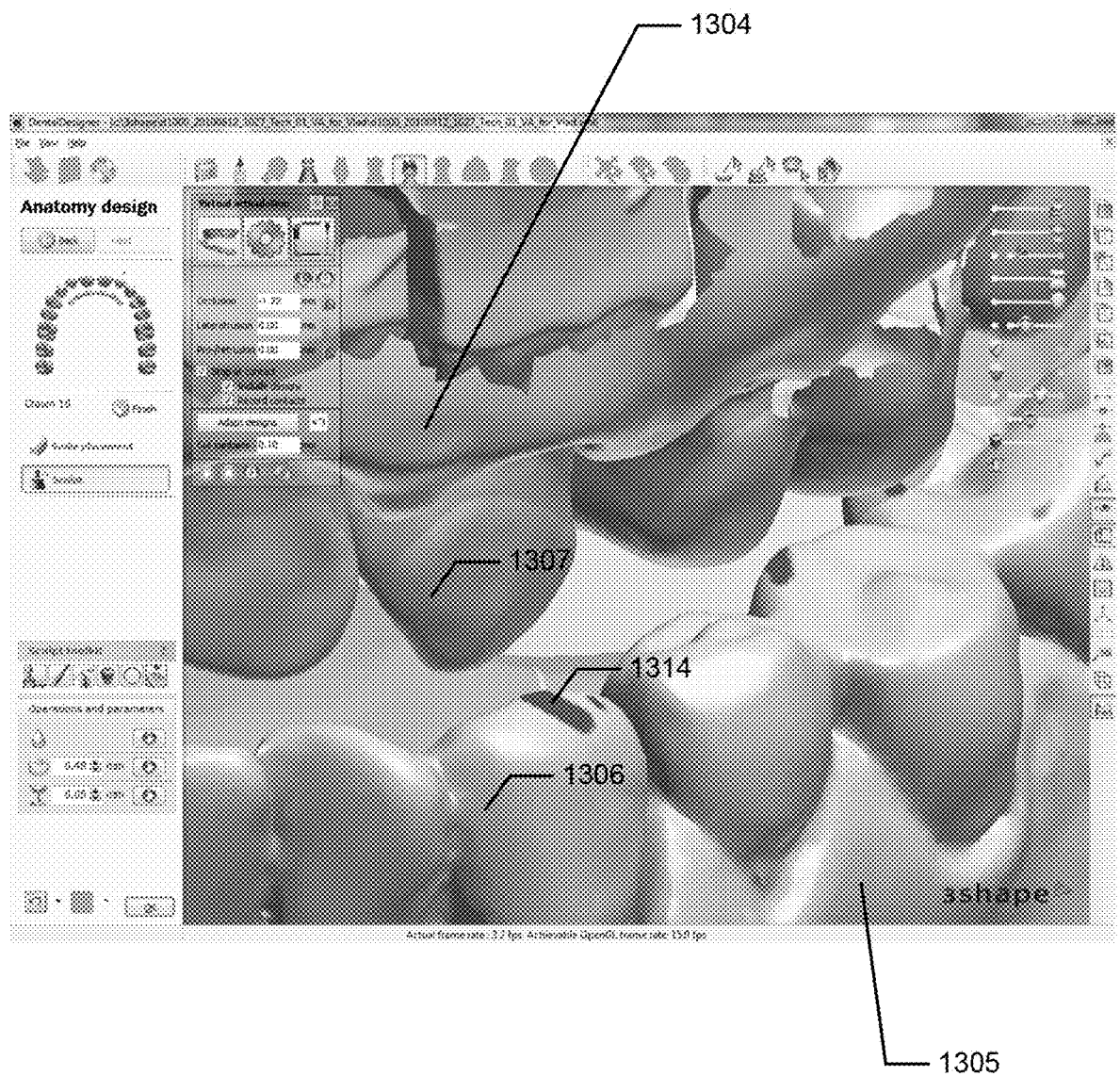

FIG. 13c) shows the end position of the movement of the jaws, and all the collision points are marked on the teeth and restorations. The restoration 1307 can now be modelled by virtually removing or remodeling material from the restoration, whereby the collision in point 1314 will not happen again when the jaws are moved relative to each other, both virtually and in the patient's mouth.

FIG. 14 shows an example of displacing the position of a prepared tooth for designing the restoration.

Figure 14A:
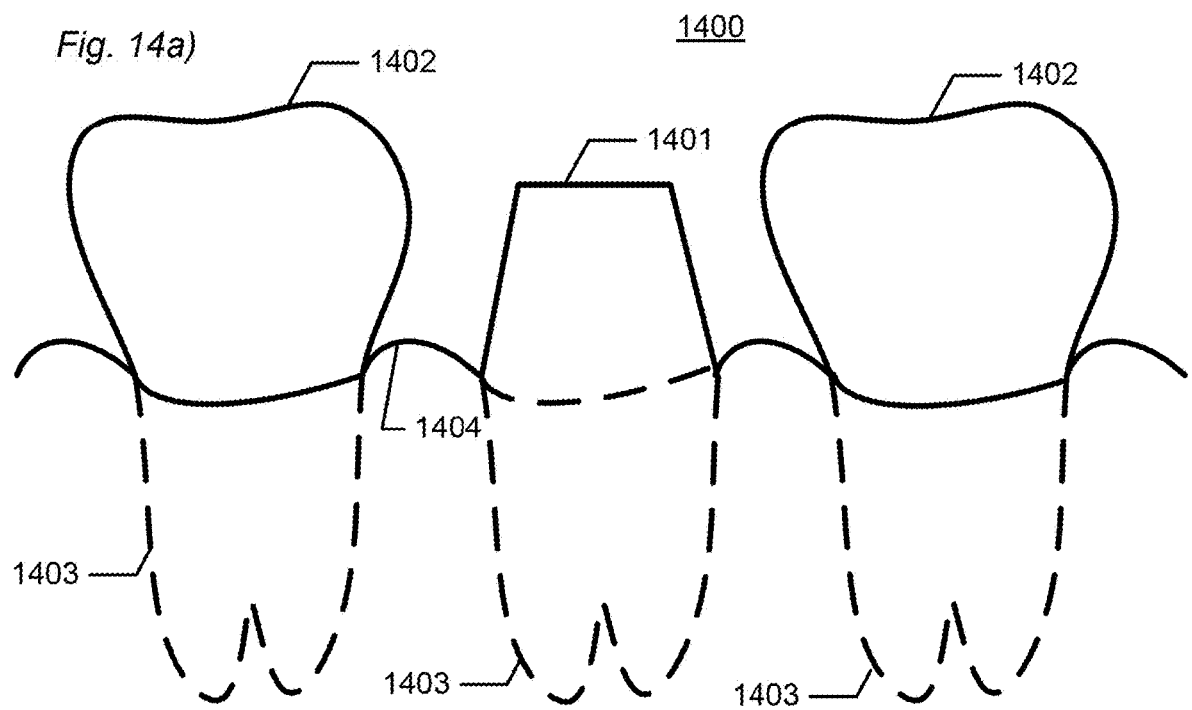
FIG. 14a-14d show an example of displacing the position of a prepared tooth for designing the restoration.

FIG. 14a) shows an example of a 3D representation of a set of teeth 1400, where a tooth 1401 has been prepared for a restoration, such as a crown. Two neighbor teeth 1402 are also shown. The tooth roots 1403 are indicated. The tooth roots 1403 may be derived from a CT scan or may be extrapolated based in a normal 3D scan. Showing the tooth roots 1403 in the 3D representation is optional, since designing a restoration does not require seeing the tooth root, but it may a help for the operator designing the restoration. The gingival 1404 is also seen.

Figure 14B:
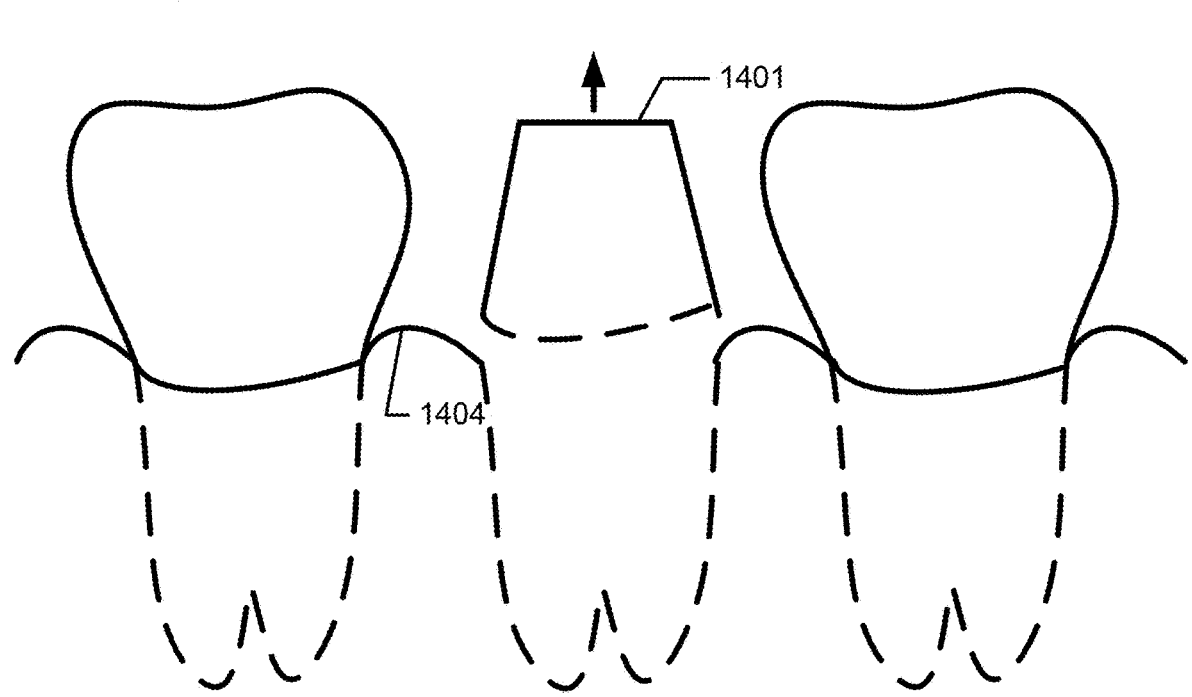

FIG. 14b) shows that the preparation 1401 is vertically displaced from its position at the gingival 1404 and from the neighbor teeth to reduce the distance to the antagonist when designing the restoration.

Figure 14C:
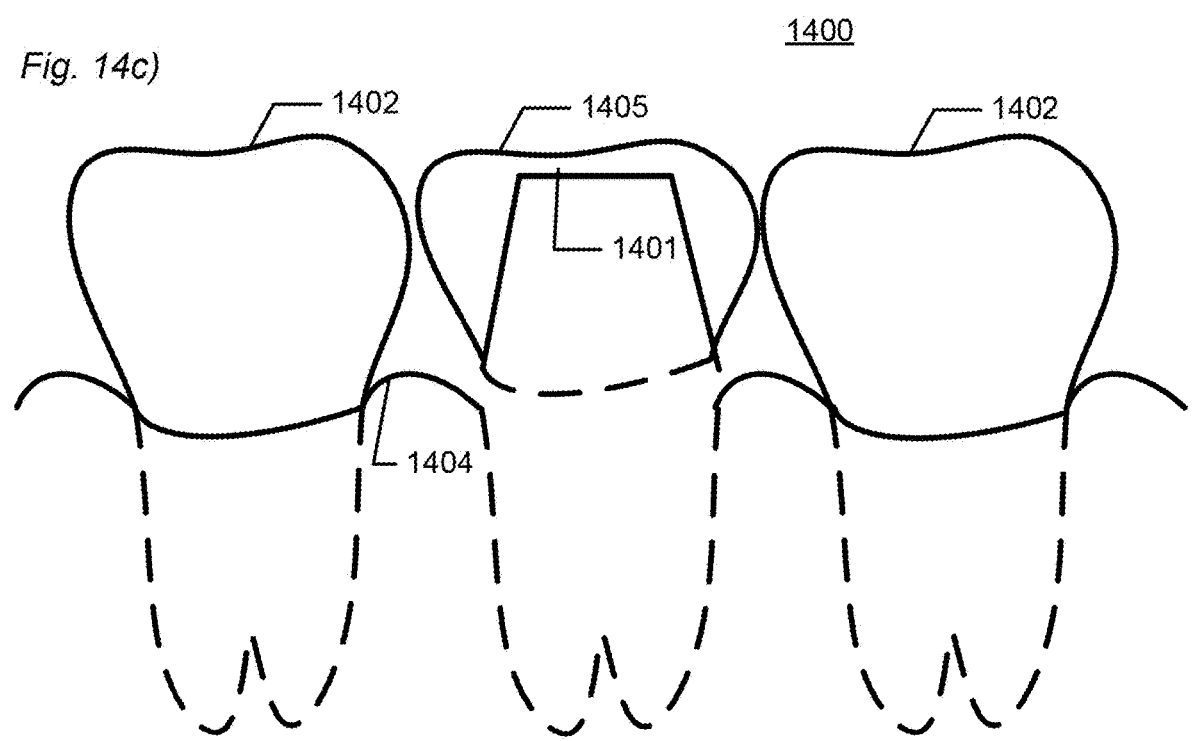

FIG. 14c) shows that a restoration 1405, here in the form of a crown, is designed on the preparation, when the preparation is displaced from the gingival 1404 and the neighbor teeth. Thus the restoration is designed in a different occlusion than the normal occlusion of the teeth. The upper edge of the restoration 1405 is shown to be substantially flush or level with the two neighbor teeth 1402 when being designed.

Figure 14D:
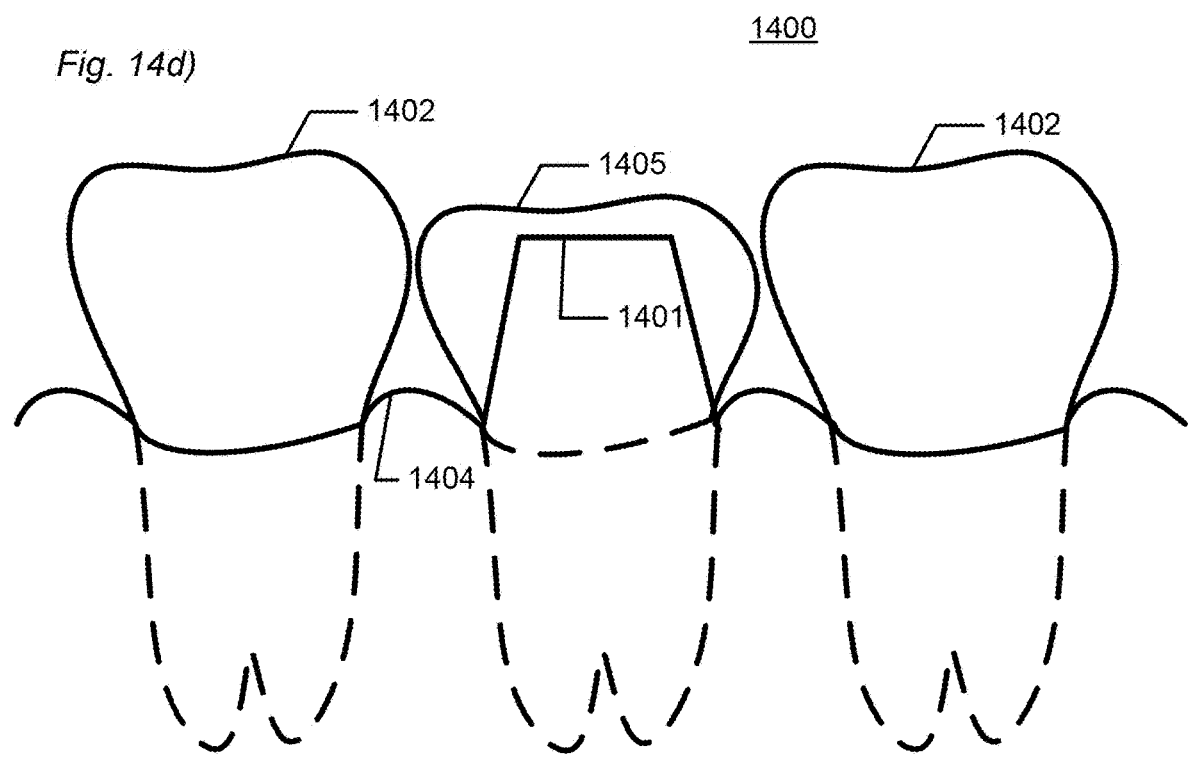

FIG. 14d) shows the situation when the preparation 1401 with the restoration 1405 is positioned in its actual position again after designing the restoration 1405. Because the restoration 1405 was designed to be level with the neighbor teeth 1402 when it was displaced, the restoration 1405 is shorter than the neighbor teeth 1402, when it is positioned in its original position again. Thus in the mouth of the patient, the restoration will be shorter than the neighbor teeth, and the restoration, which may be more fragile than the real teeth, is therefore protected better.

FIG. 15 shows an example of displacing the position of a gingival part for designing the restoration.

Figure 15A:
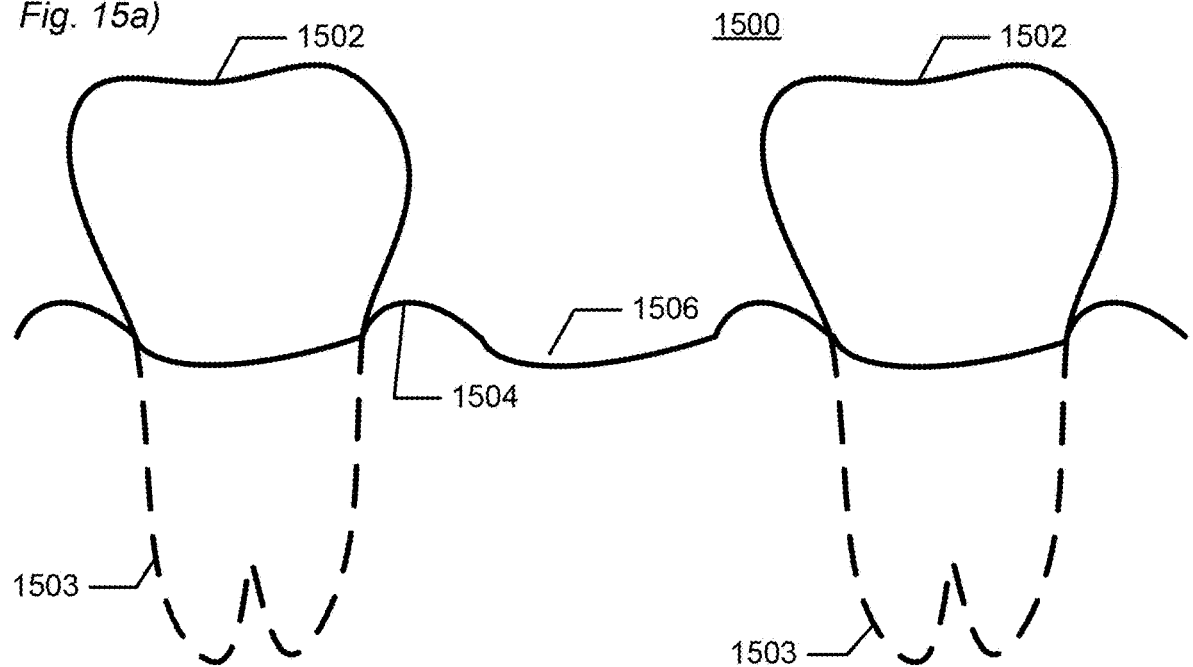
FIG. 15a-15d show an example of displacing the position of a gingival part for designing the restoration.

FIG. 15a) shows an example of a 3D representation of a set of teeth 1500 with a missing tooth in a region of the gingival 1506. The missing tooth may have been broken, died, pulled out due to disease etc. A restoration should be made to replace the missing tooth in the region 1506. Two neighbor teeth 1502 are also shown. The tooth roots 1503 are indicated. The tooth roots 1503 may be derived from a CT scan or may be extrapolated based in a normal 3D scan. Showing the tooth roots 1503 in the 3D representation is optional, since designing a restoration does not require seeing the tooth root, but it may a help for the operator designing the restoration. The gingival 1504 is also seen.

The restoration to made to replace the missing tooth may be a bridge. The bridge may comprise a pontic in the place of the missing tooth and two crowns on the neighbor teeth 1502.

Figure 15B:
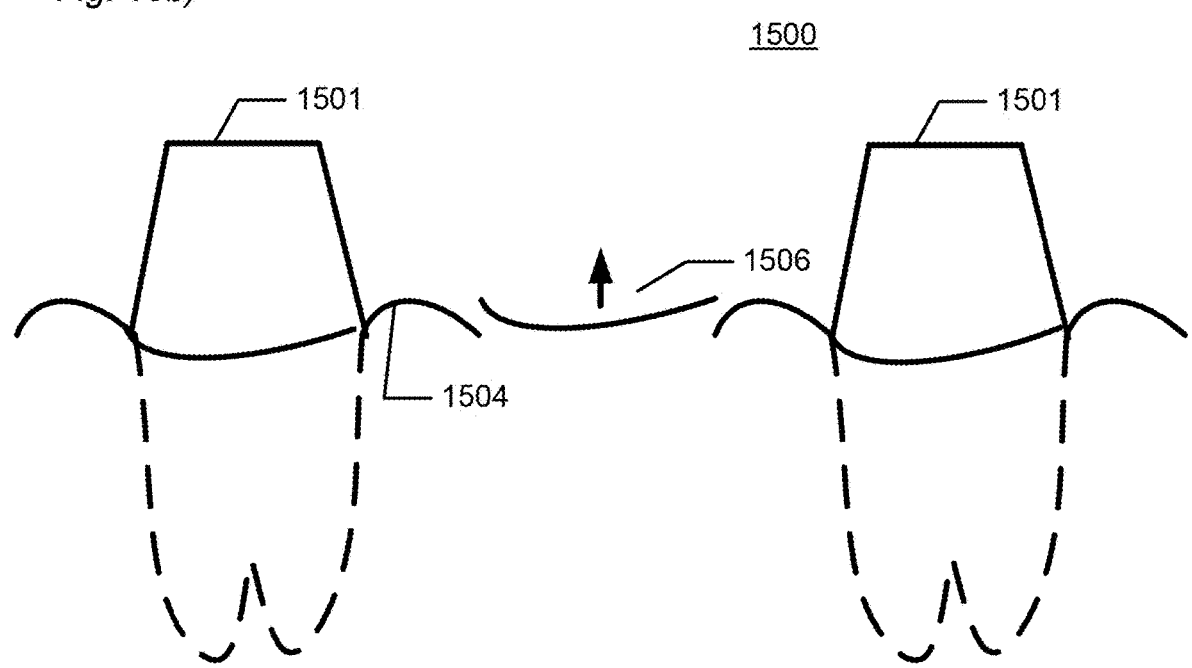

FIG. 15b) shows that the two neighbor teeth have been prepared and are now prepared teeth 1501. The region of the gingival 1506 of the missing tooth is displaced from its original position at the gingival.

Figure 15C:
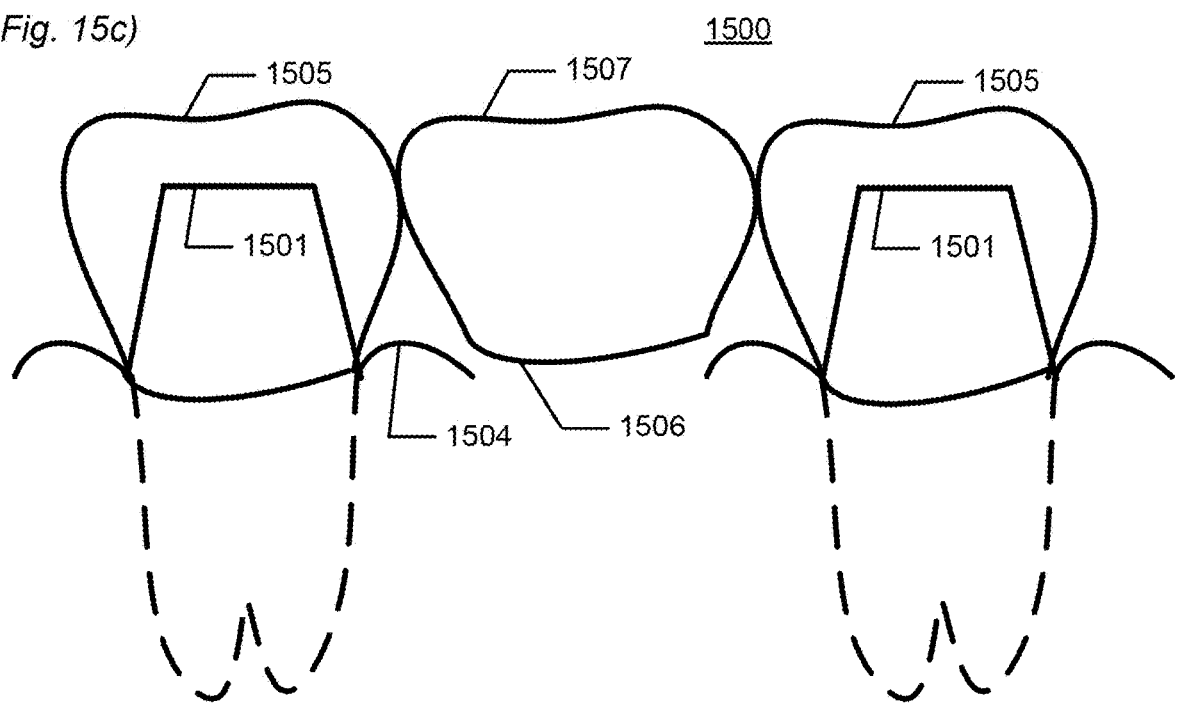

FIG. 15c) shows that a restoration, here in the form of a bridge, is designed. A pontic 1507 is arranged in the place of the missing tooth, and crowns 1505 have been designed on the two preparations 1501. The pontic is attached to the crowns. The pontic 1507 is designed, when the region of the gingival 1506 is displaced from its original position. The upper edge of the pontic 1507 is substantially flush or level with the designed crowns 1505 on the two prepared neighbor teeth 1501.

Figure 15D:
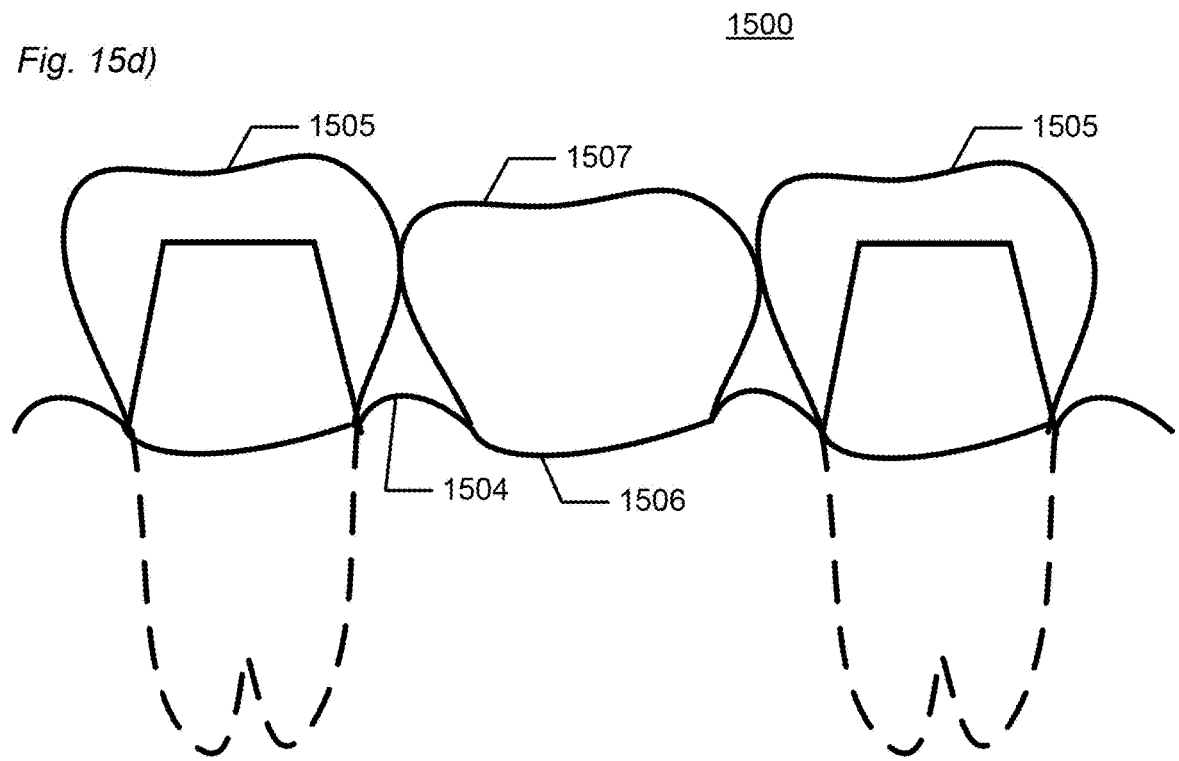

FIG. 15d) shows the situation when the pontic 1507 and the region of the gingival 1506 is positioned in its actual position again after designing the pontic 1507. Because the pontic 1507 was designed to be level with the crowns 1505 of the neighbor teeth, when it was displaced, the pontic 1507 is shorter than the crowns 1505 neighbor teeth, when the pontic 1507 is positioned in its original position again. Thus in the mouth of the patient, the pontic will be shorter than the crowns of the neighbor teeth, and the pontic, which may be more fragile than the crowns of the neighbor teeth, is therefore protected better.

Figure 16:
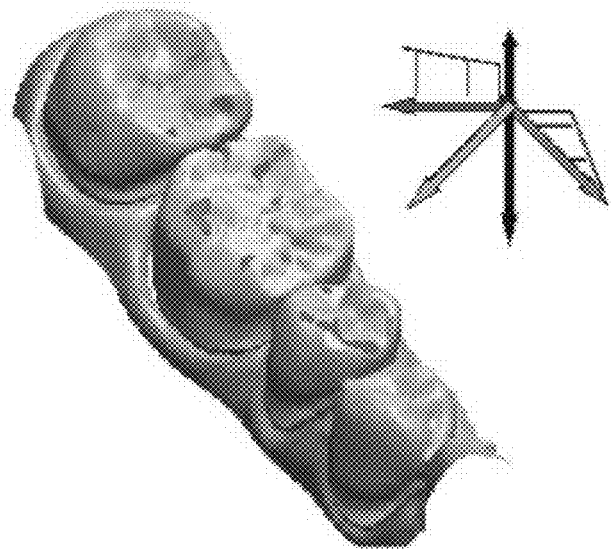
FIG. 16 shows an example of an occlusal compass.

FIG. 16 shows an example of an occlusal compass.

The occlusal compass indicates movements during dynamic occlusion in the following directions:
  protrusion;
  retrusion;
  laterotrusion to the right;
  laterotrusion to the left;
  mediotrusion to the right;
  mediotrusion to the left;
  latero-re surtrusion to the right;
  latero-re surtrusion to the left.

The occlusal compass indicates the contact or collision in different movement directions with different colors. The colors may be according to the international coloring scheme. The occlusal compass used in the virtual simulation is a unique digital tool.

Figure 17:
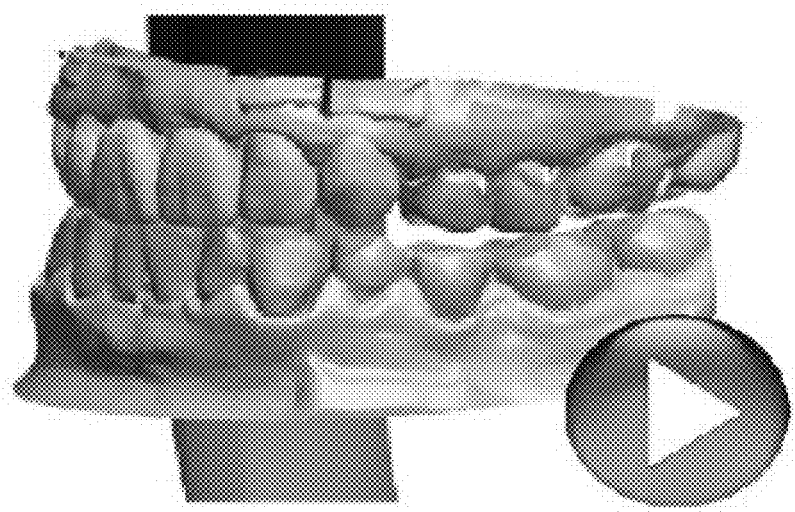
FIG. 17 shows an example of playing a recording of the jaw movements.

FIG. 17 shows an example of playing a recording of the jaw movements.

The movement of the virtual upper jaw and the virtual lower jaw relative to each other has been recorded, and before and/or after modeling a restoration, the recording can be played to test the modeling. A predefined motion sequence may also be played.

Figure 18:
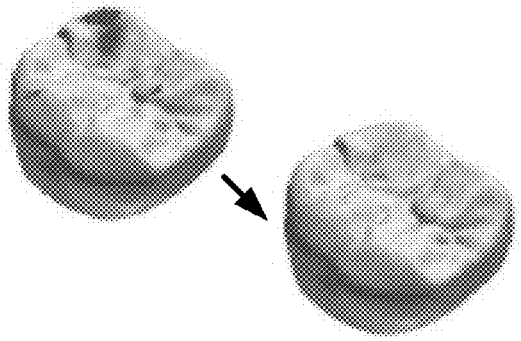
FIG. 18 shows an example of modeling a restoration to compensate for collisions with the opposite teeth.

FIG. 18 shows an example of modeling a restoration to compensate for collisions with the opposite teeth.

During the movement of the virtual upper jaw and the virtual lower jaw relative to each other the collisions, marked with on the restoration, occlusion between teeth are registered, and after the movement is finished, modeling of the collision points of the restoration is performed.

FIG. 19 shows examples of virtual articulators resembling physical articulators form different manufacturers.

Figure 19A:
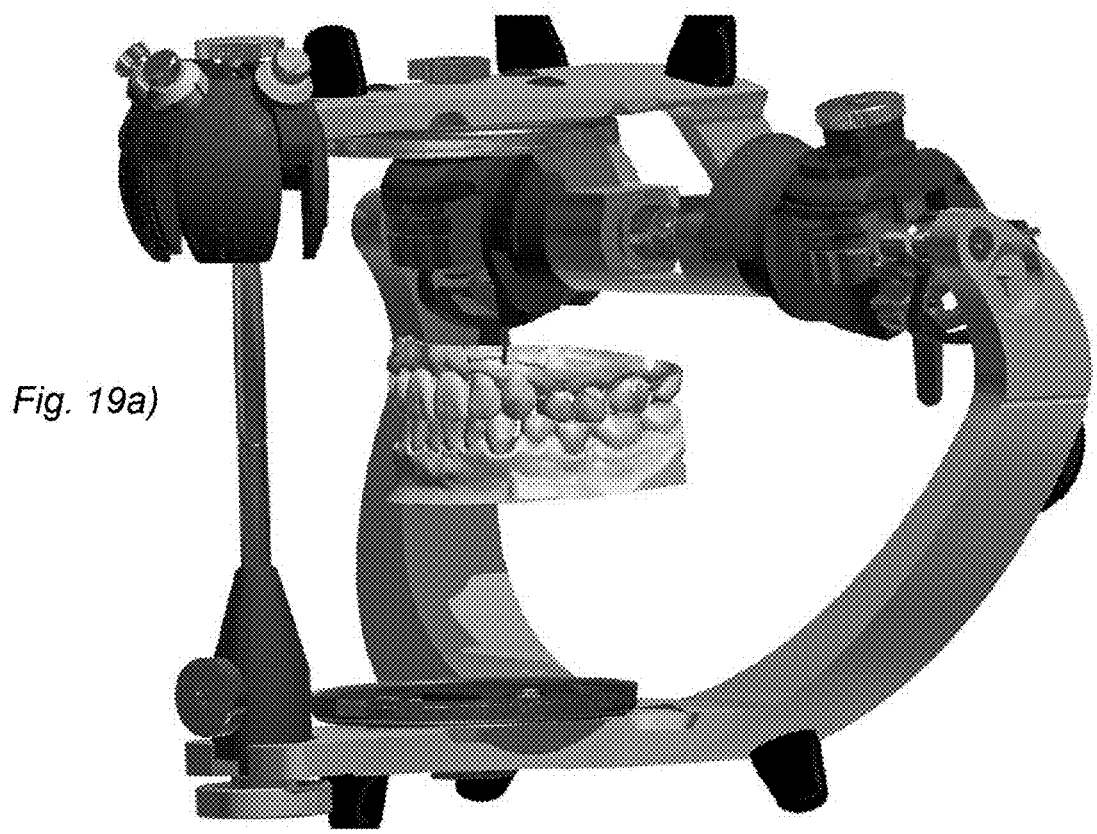
FIG. 19a-19d show examples of virtual articulators resembling physical articulators form different manufacturers.
Figure 19B:
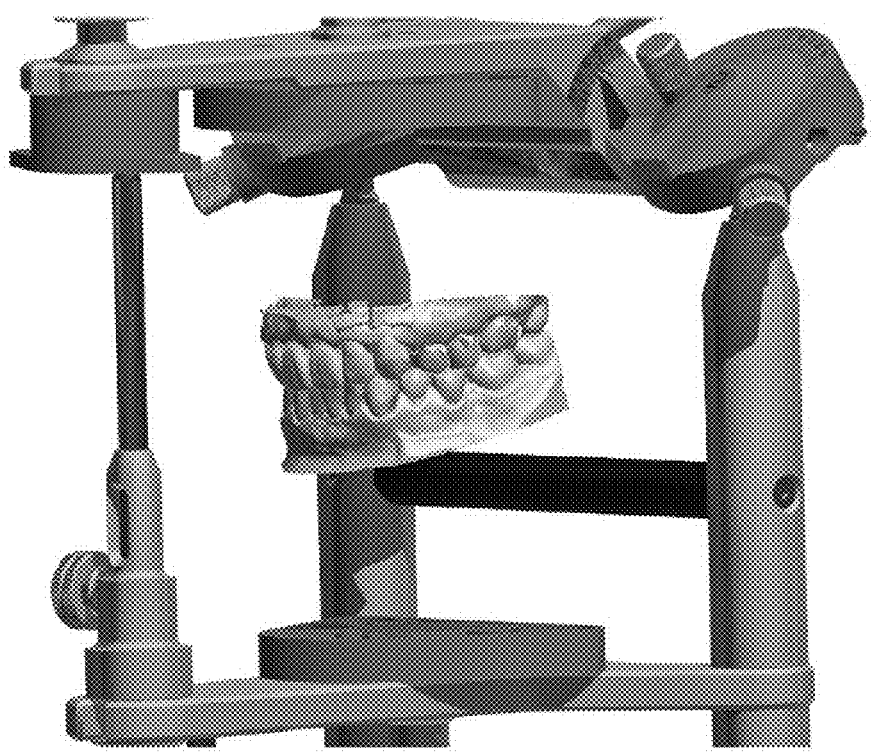
Figure 19C:
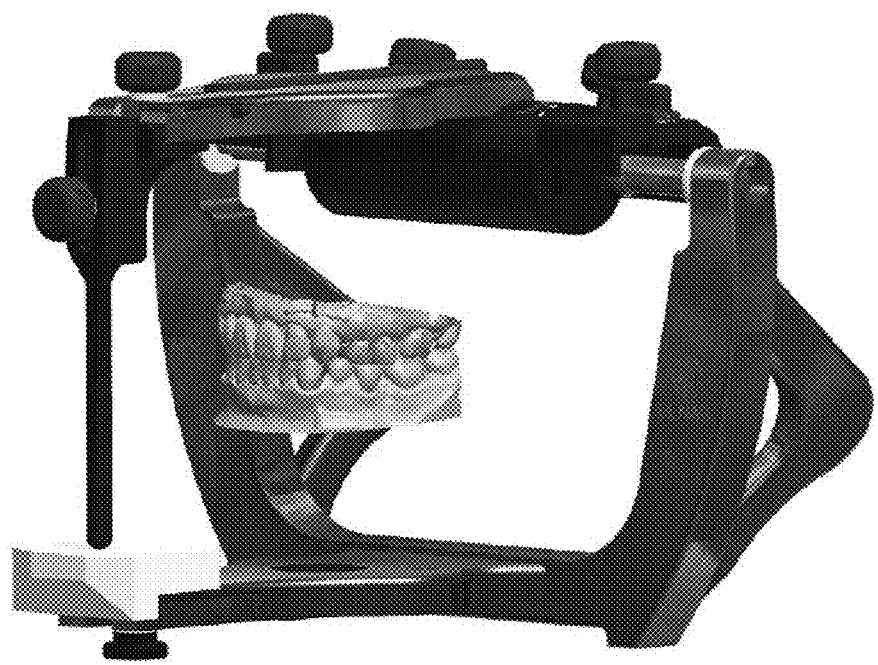
Figure 19D:
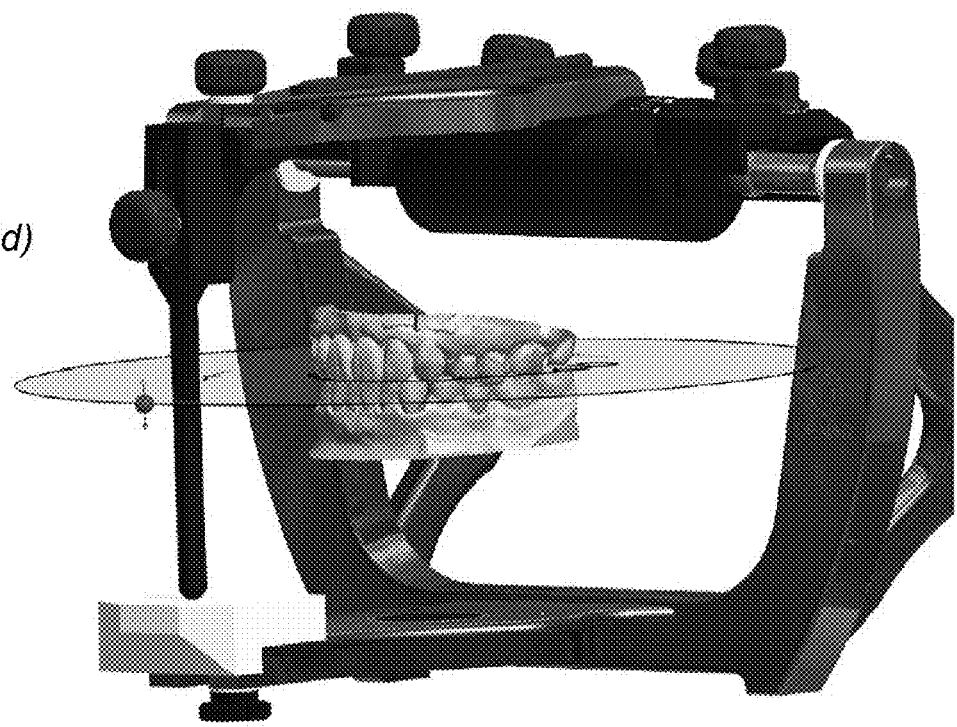

FIG. 19a) shows an articulator from KaVo.
FIG. 19b) shows an articulator from SAM.
FIG. 19c) shows an articulator from Denar.
FIG. 19d) shows the articulator from Denar with the occlusal plane arranged relative to the virtual teeth model.

FIG. 20 shows an example of a virtual articulator, which only exists as a virtual articulator.

Figure 20A:
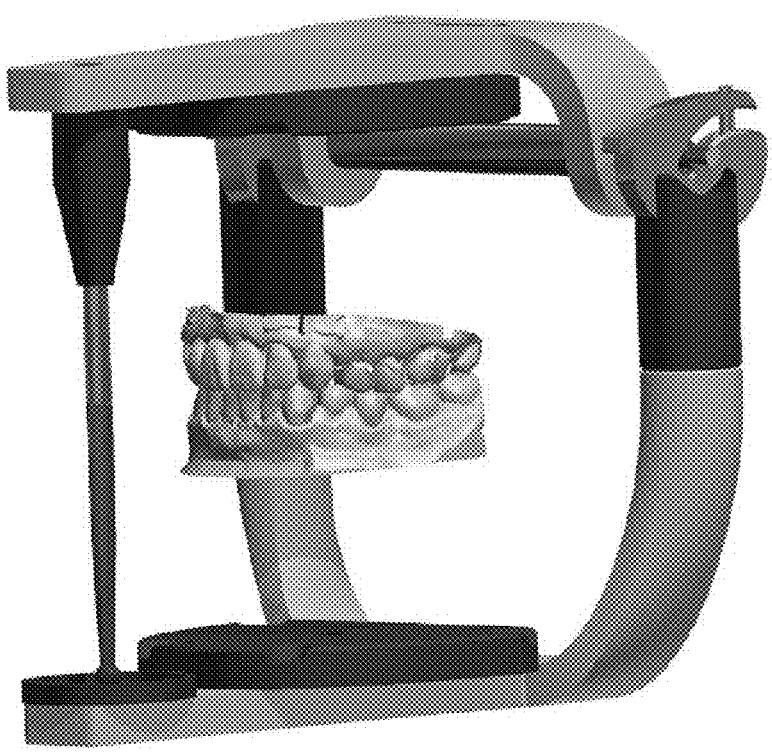
FIG. 20a-20b show an example of a virtual articulator, which only exists as a virtual articulator.

FIG. 20a) shows a 3 Shape virtual articulator. The articulator does not exist as a physical articulator.

Figure 20B:
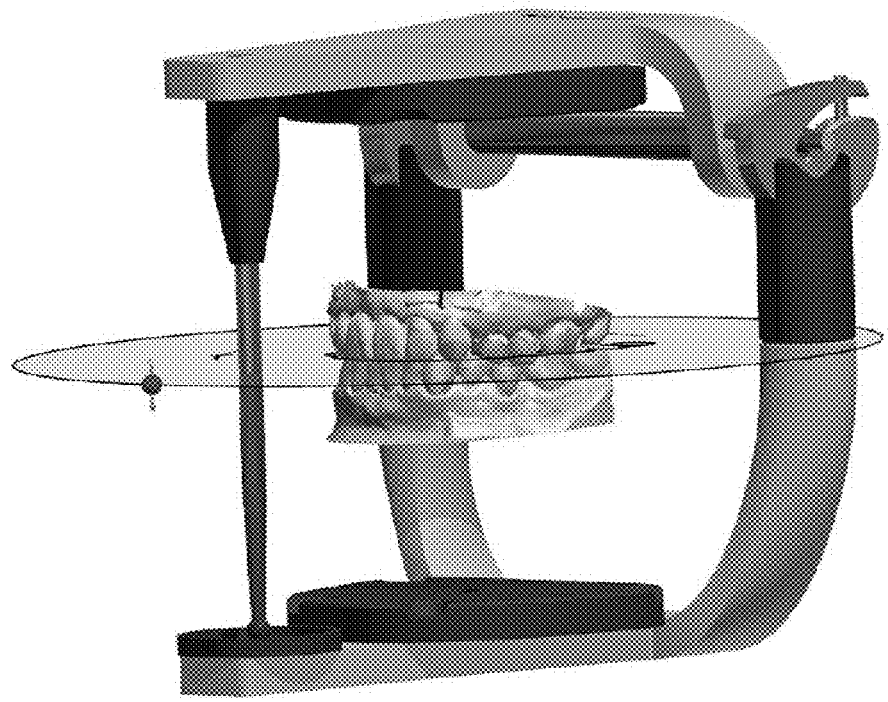

FIG. 20b) shows the 3 Shape virtual articulator with the occlusal plane arranged relative to the virtual teeth model.

FIG. 21 shows examples of the traces of movement.

Figure 21A:
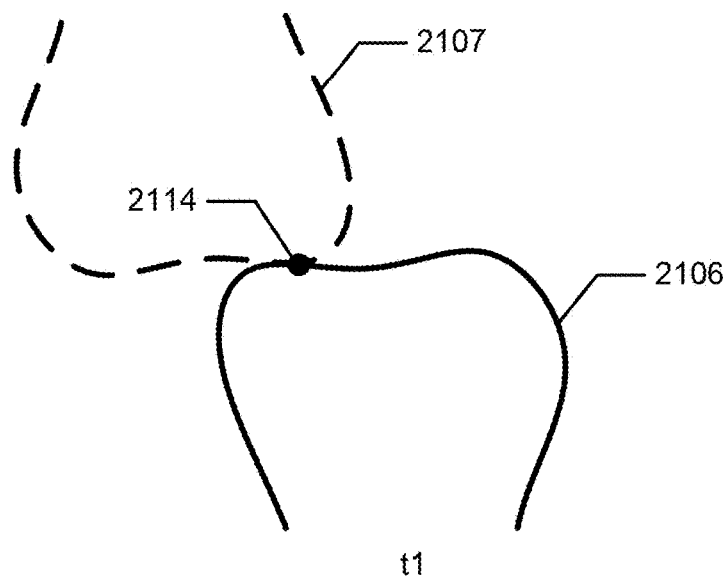
FIG. 21a-21e show examples of the traces of movement.

FIG. 21a) shows an example of a first collision point 2114 between an unmodified tooth 2106 and another unmodified tooth or restoration 2107 at time t1.

Figure 21B:
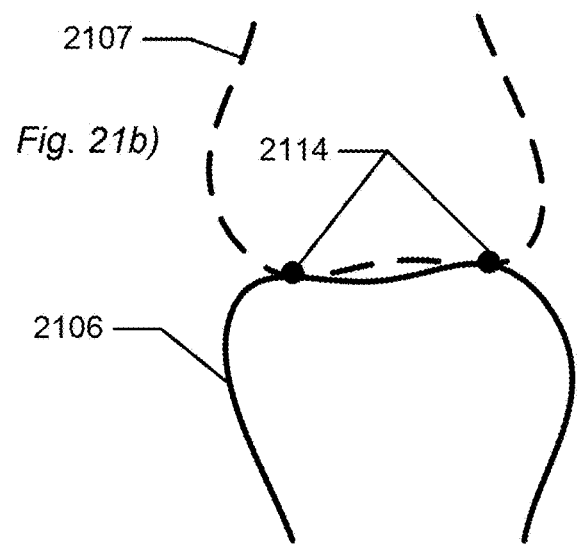

FIG. 21b) shows an example of a subsequent collision point 2114 between the unmodified tooth 2106 and the other unmodified tooth or restoration 2107 at time t2.

Figure 21C:
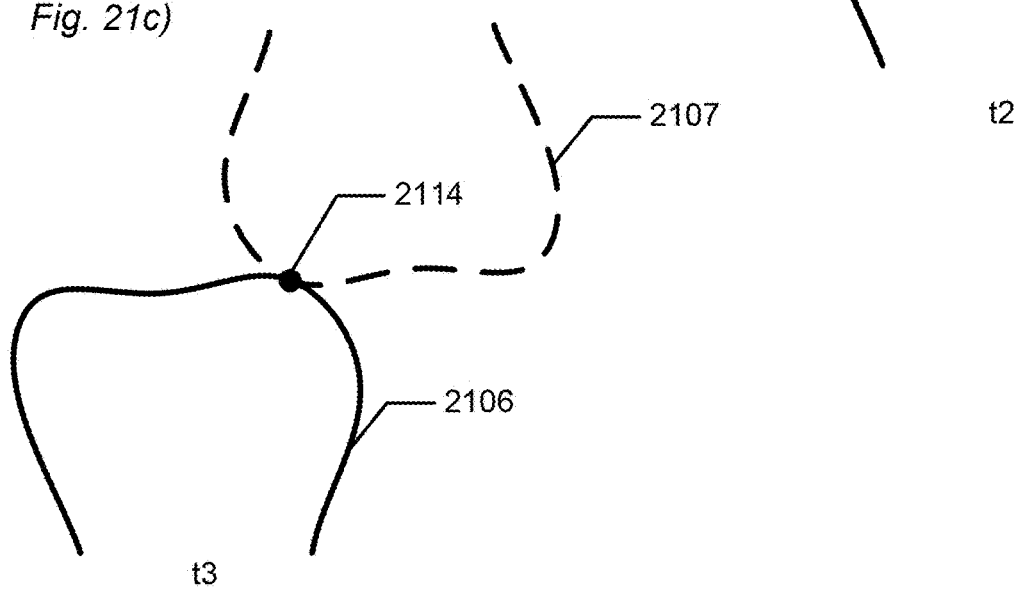

FIG. 21c) shows an example of another subsequent collision point 2114 between the unmodified tooth 2106 and the other unmodified tooth or restoration 2107 at time t3.

Figure 21D:
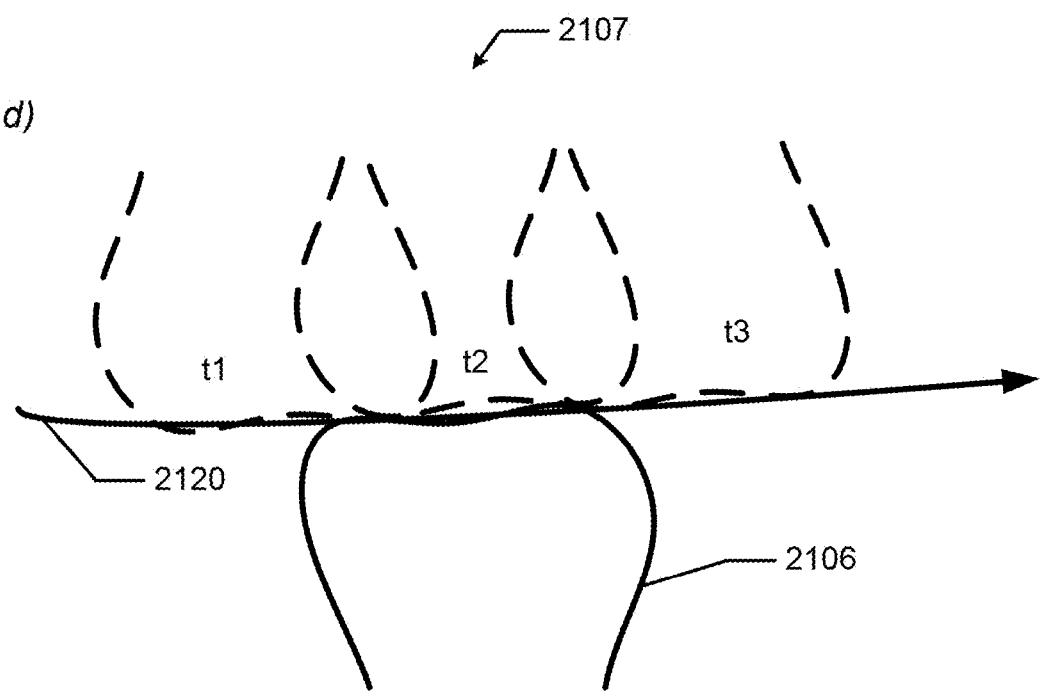

FIG. 21d) shows the trace of the motion for the other unmodified tooth or restoration 2107 and the tooth 2106 at the three time instances, t1, t2, t3.

The trace of the motion between the tooth 2106 and the other unmodified tooth or restoration 2107 is indicated by the arrows 2120. The surface of collision points 2114 may be denoted the trace motion, the motion trace surface etc.

Thus when unmodified teeth are simulated relative to each other, their motion traces or their surfaces cannot penetrate each other. The same may be the case for a restoration relative to an unmodified tooth.

However, it may alternatively be the case that when a restoration and an unmodified tooth are simulated relative to each other, the motion surface of the restoration may penetrate the unmodified tooth.

Thus the term collision surface or trace of collisions points or collision points surface is used for both describing when unmodified teeth are simulated to move relative to each where the teeth collide and do not penetrate each other and for describing when a restoration is simulated relative to unmodified teeth where the restoration may penetrate the unmodified teeth, i.e. the restoration and the unmodified may penetrate each other.

The simulated collisions or collision surfaces between unmodified teeth may determine the motion which can be performed between the upper and lower teeth models.

This determined motion may then be used and studied when designing the restoration.

Figure 21E:
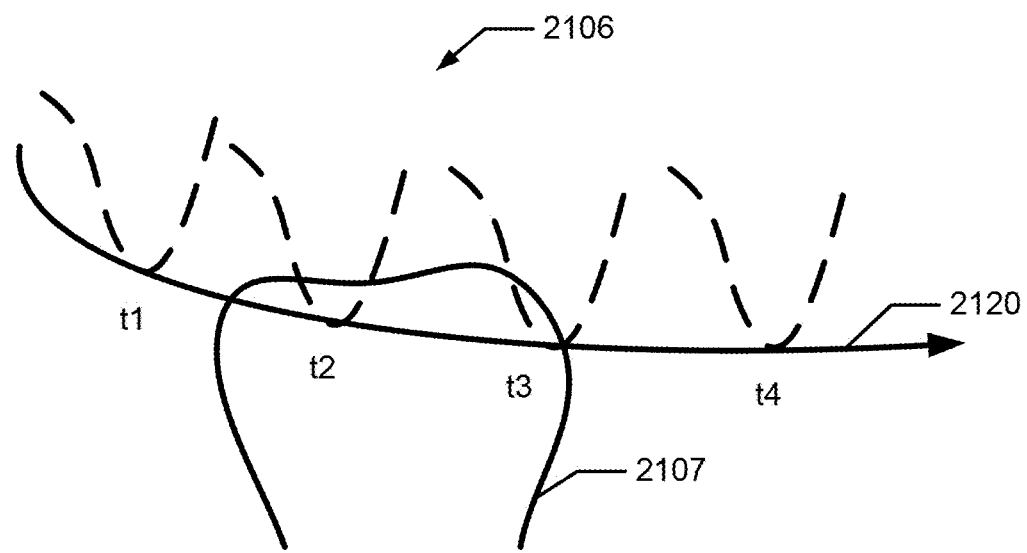

FIG. 21e) shows the trace 2120 of a motion for a restoration 2107 and a tooth 2106 at the four time instances, t1, t2, t3, t4. The motion is shown at the three time instances t1, t2, t3, t4 and time instance lying in between and before and after.

In FIG. 21e) the restoration 2107 and the tooth 2106 are shown to penetrate each other in the motion.

The surface of collision or penetration points may be denoted the trace motion 2120.

The tooth 2106 is shown to move relative to the restoration 2107, however it may be vice versa, i.e. that the restoration 2107 moves relative to the tooth 2107.

FIG. 22 shows an example of virtual simulation of orthodontic treatment planning.

Figure 22A:
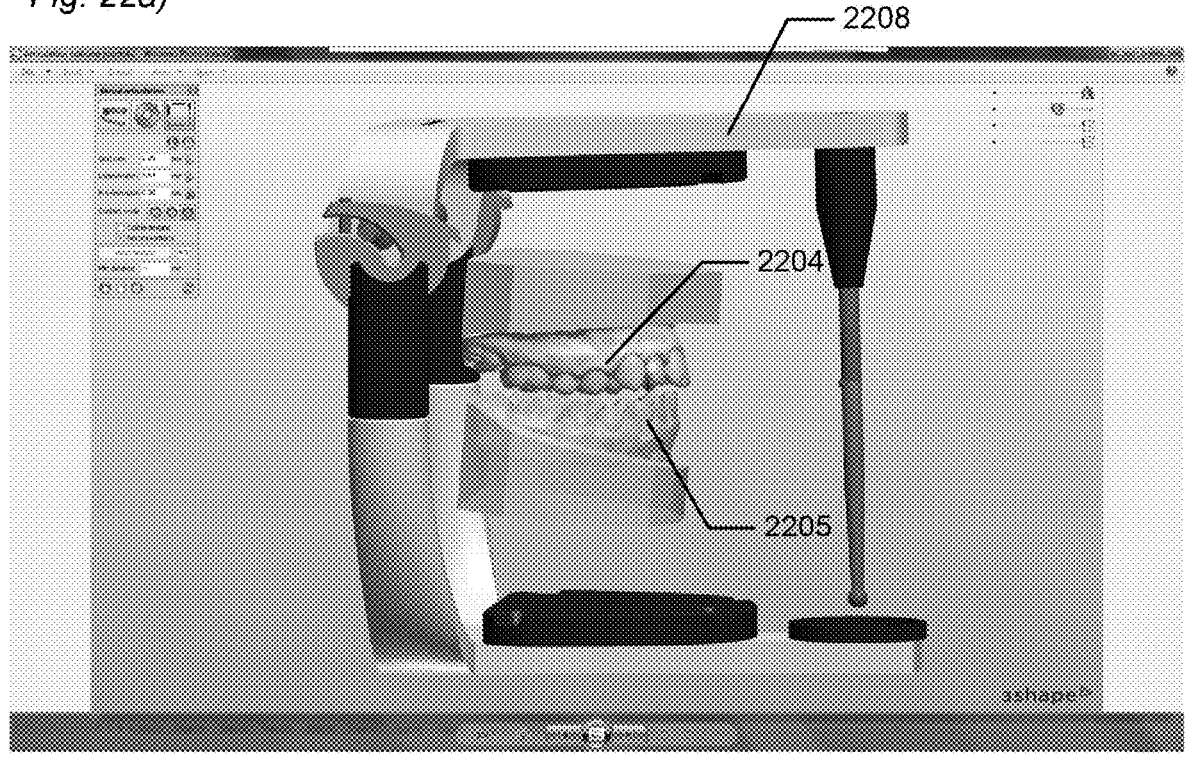
FIG. 22a-22b show an example of virtual simulation of orthodontic treatment planning.

FIG. 22a) shows a virtual orthodontic model of teeth with an upper model 2204 and a lower model 2205 in a virtual articulator 2208 for simulating the occlusion. The simulation of occlusion in the virtual articulator can detect and study malocclusion, and assist and/or determine an orthodontic treatment planning. An orthodontic treatment can also be performed for pure cosmetic reasons, if the patient's teeth are arranged aesthetically.

Figure 22B:
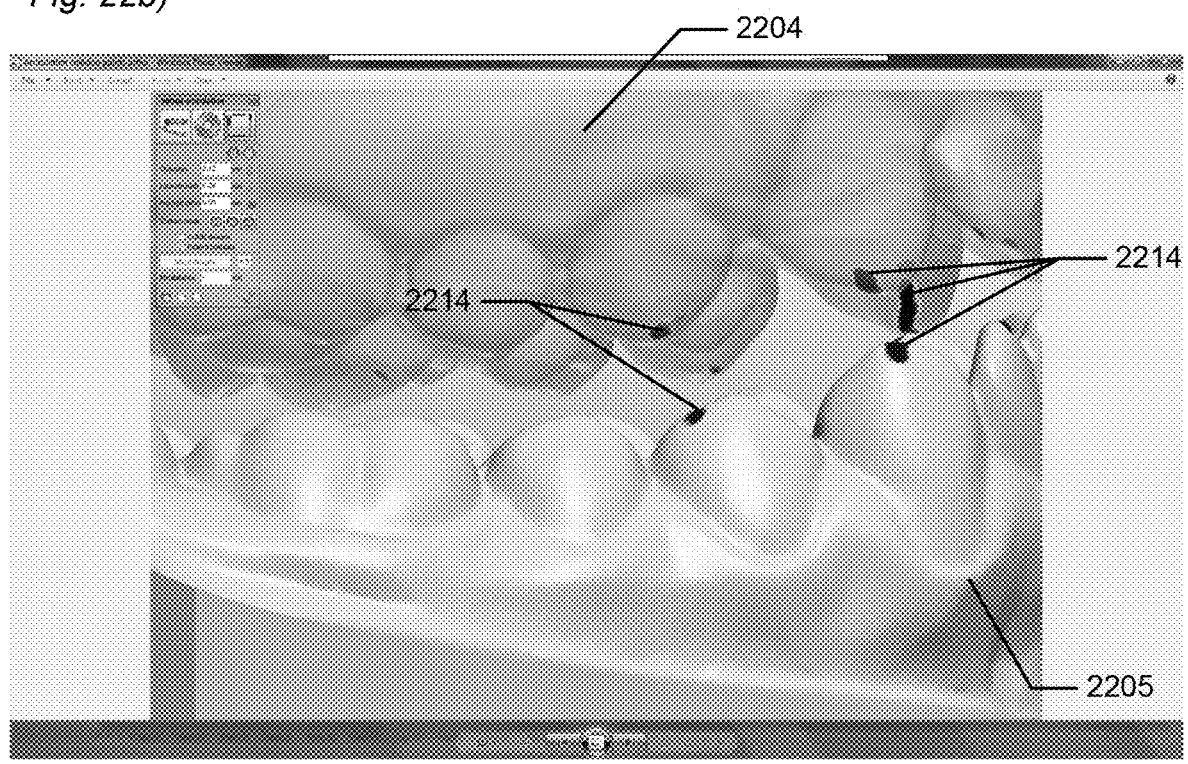

FIG. 22b) shows a zoom-in on the teeth in the virtual models 2204, 2205, where contact areas or collision points 2214 are registered during simulation of the occlusion. The detected contact areas or collision points 2214 can be used in determining the treatment planning to be performed.

FIG. 23 shows an example of virtual simulation of dental displacement.

Figure 23A:
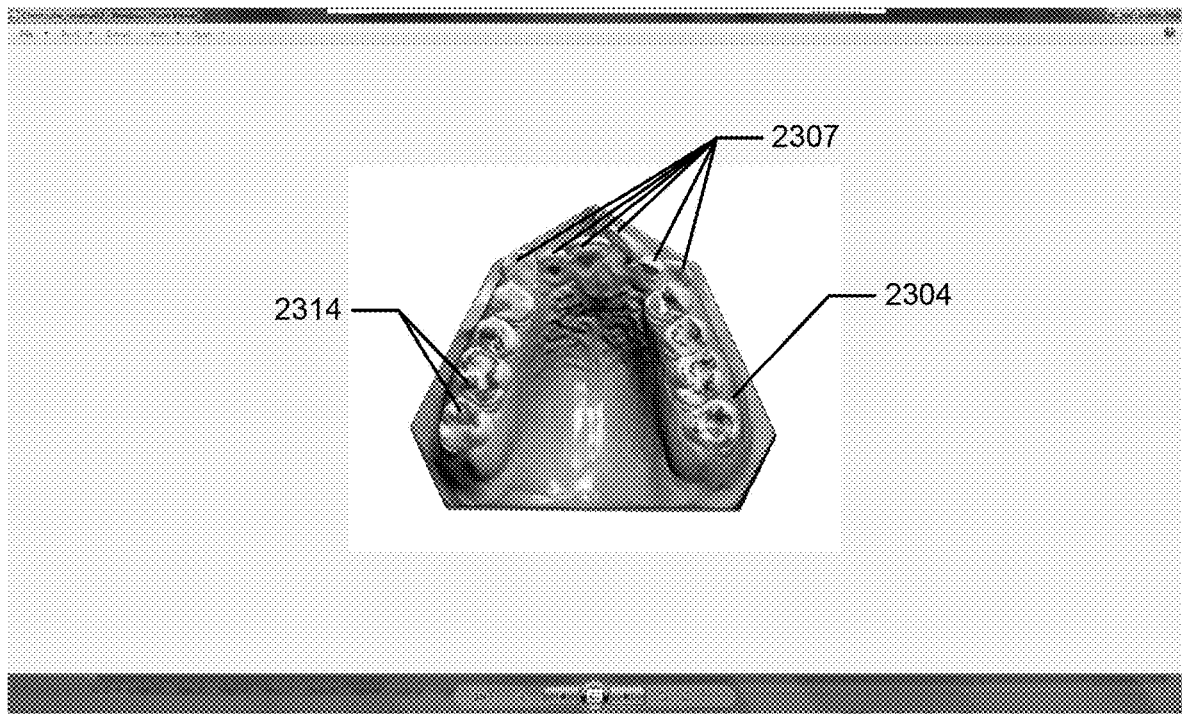
FIG. 23a-23b show an example of virtual simulation of dental displacement.

FIG. 23a) shows a virtual upper teeth model 2304 of a patient's teeth before orthodontic treatment, where the teeth 2307 are not arranged aesthetically. The contact areas or collision point 2314 detected or registered in a virtual articulator simulation are shown on the teeth.

Figure 23B:
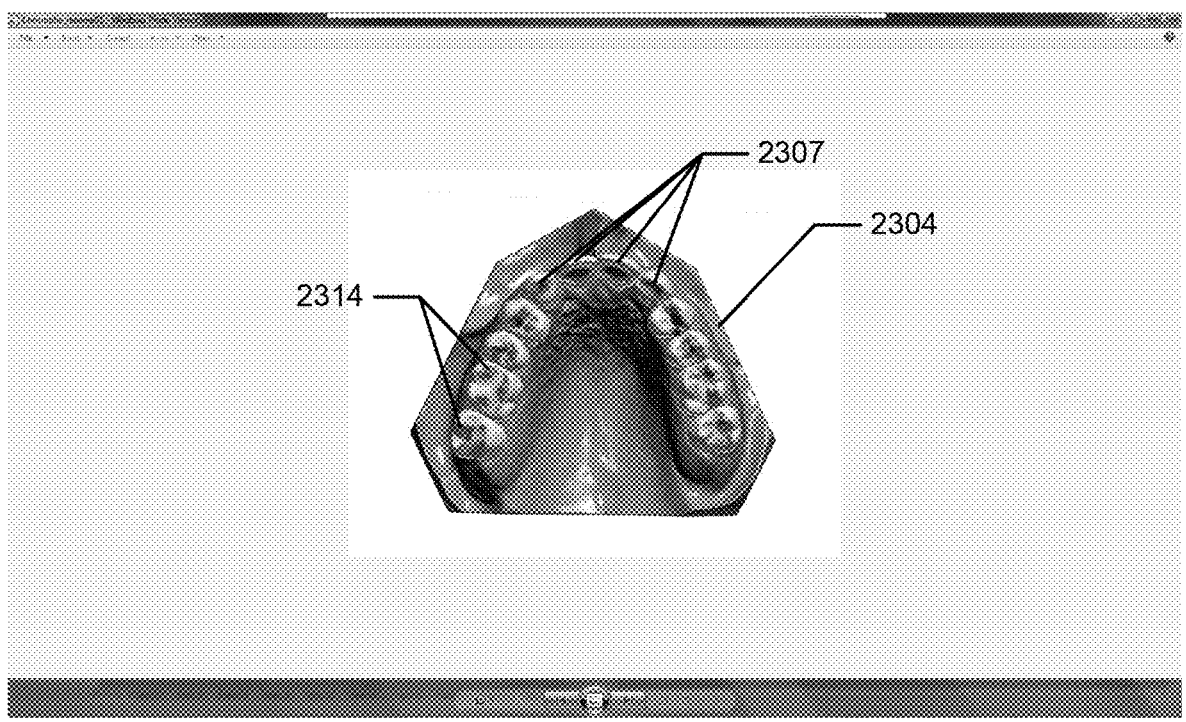

FIG. 23b) shows an example of the virtual upper teeth model 2304 with a suggested final result which can be obtained after displacement of the teeth 2307.

Based on the image in FIG. 23b) a patient can decide whether he wish to have the dental displacement performed for obtaining the aesthetic set of front teeth.

FIG. 24 shows an example of an orthodontic appliance for displacing teeth.

Figure 24A:
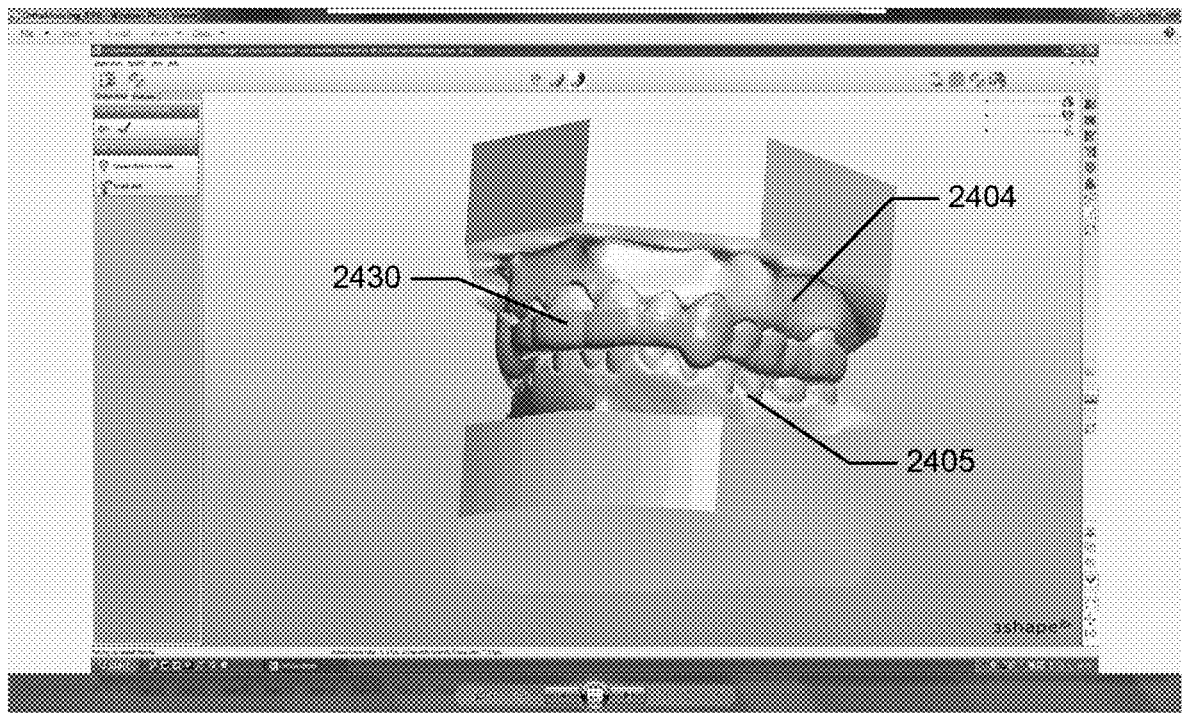
FIG. 24a-24d show an example of an orthodontic appliance for displacing teeth.

FIG. 24a) shows a virtual upper model 2404 and a virtual lower model 2405, where a virtual orthodontic appliance 2430 in the form of a splint is shown to be arranged in the teeth in the upper model 2404. The physical appliance may be worn by a patient on his teeth for treating temporal mandibular dysfunction. The appliance 2430 may be virtually designed using a virtual articulator, e.g. as shown in FIG. 22a).

Figure 24B:
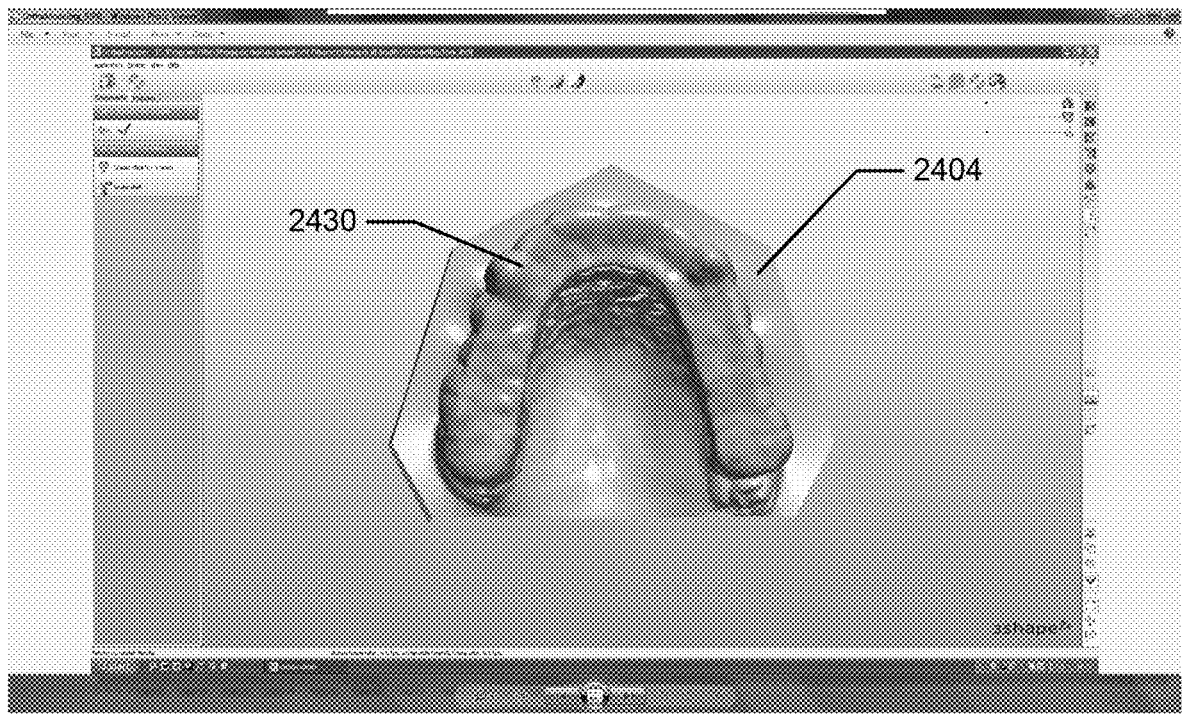

FIG. 24b) shows a top view of the appliance 2430 on the virtual teeth model 2404.

Figure 24C:
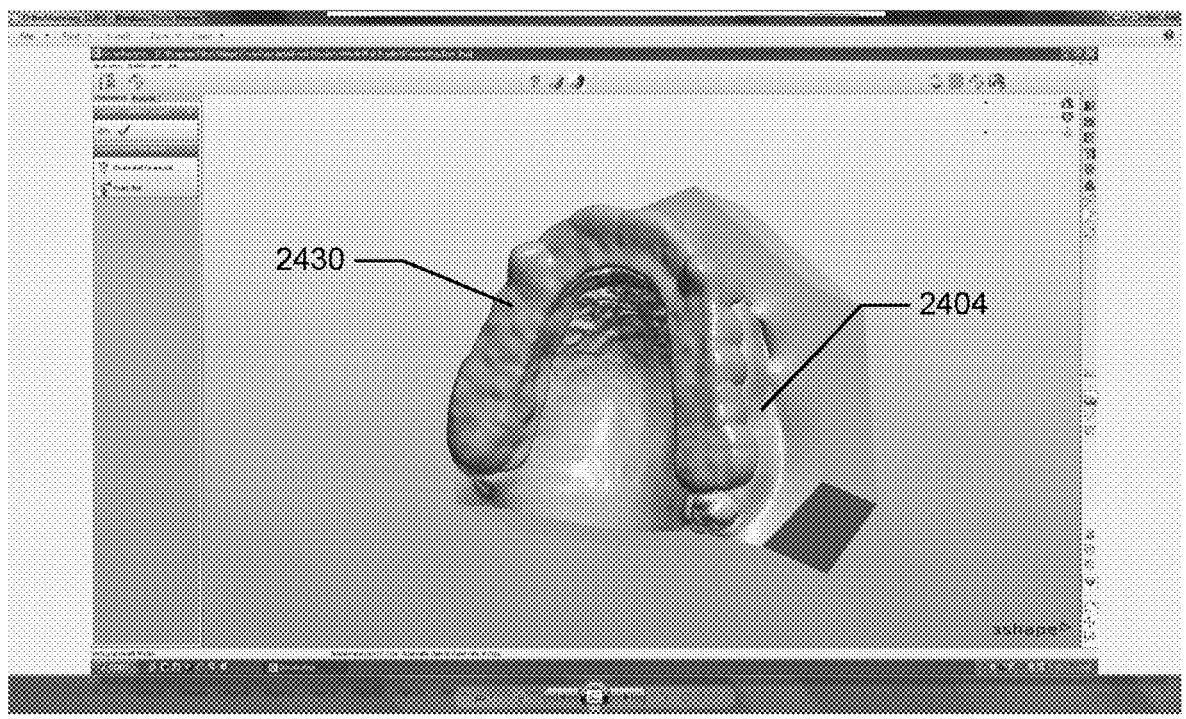

FIG. 24c) shows a perspective side view of the appliance 2430 on the virtual teeth model 2404.

Figure 24D:
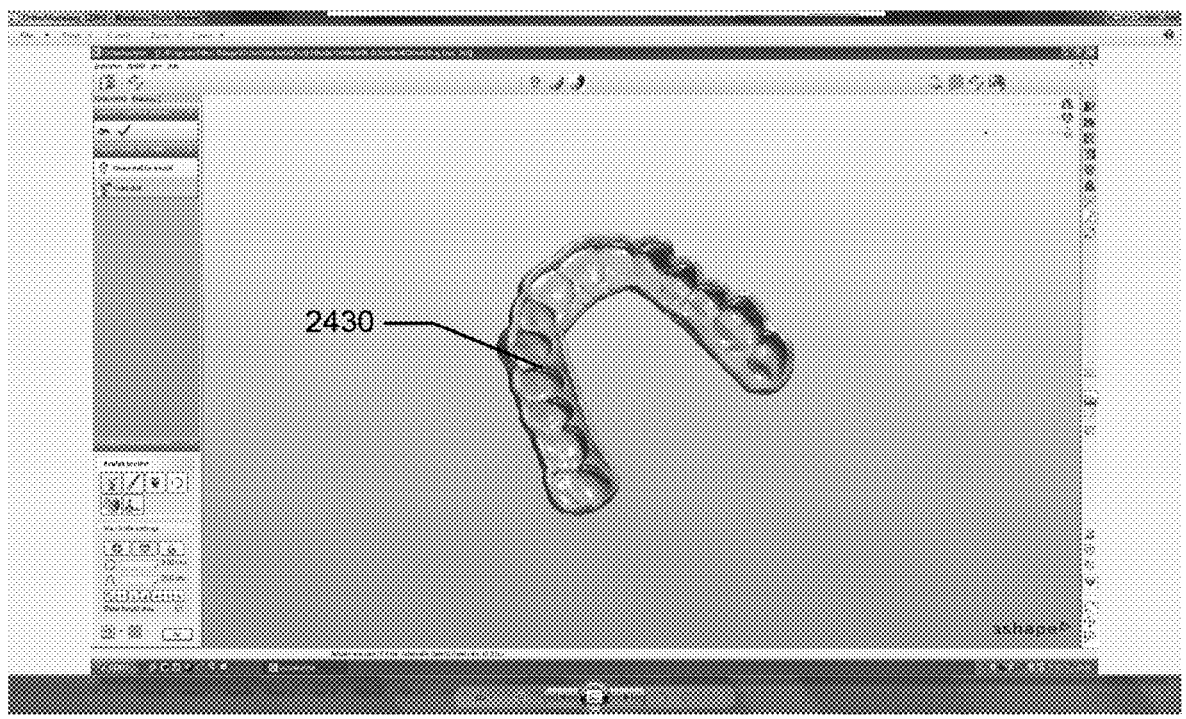

FIG. 24d) shows a bottom view of the appliance 2430.

The appliance design in FIG. 24 are the courtesy of and kindly provided by Tridentestense Ortodonzia S.r.l, Italy.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

When a claim refers to any of the preceding claims, this is understood to mean any one or more of the preceding claims.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A computer-implemented method of simulating occlusion of teeth, the method comprises using a dynamic virtual articulator when performing computer-aided designing of one or more dental restorations for a patient, the method further comprises:

providing the dynamic virtual articulator, the dynamic virtual articulator including a virtual three-dimensional model of the upper jaw and a virtual three-dimensional model of the lower jaw resembling the upper jaw and lower jaw, respectively, of the patient's mouth, wherein the virtual three-dimensional model of the upper jaw and the virtual three-dimensional model of the lower jaw include three dimensional models of teeth without restorations, and at least one of the virtual three-dimensional model of the upper jaw and the virtual three-dimensional model of the lower jaw with three dimensional models of teeth including one or more dental restorations;

displacing the at least one or more virtual dental restorations vertically relative to the jaw from an original position on at least one of the virtual three-dimensional model of the upper jaw and the virtual three-dimensional model of the lower jaw in order to provide a relative offset of the at least one or more virtual dental restorations;

providing movement of the virtual three-dimensional model of the upper jaw and the virtual three-dimensional model of the lower jaw relative to each other for simulating dynamic occlusion, whereby collisions between the teeth in the virtual upper and virtual lower jaw occur; and providing that the teeth in the virtual three-dimensional model of the upper jaw and the virtual three-dimensional model of the lower jaw are blocked from penetrating each other's virtual surfaces in the collisions while permitting penetration of the at least one or more displaced virtual dental restorations, wherein the permission of the penetration is based on a preference of an operator or a user.

2. The computer-implemented method according to claim 1, wherein the method further comprises simultaneous modeling of the one or more displaced virtual dental restorations and collision testing of the virtual upper jaw and virtual lower jaw.

3. The computer-implemented method according to claim 1, wherein the method further comprises fixing the virtual upper jaw to the occlusal axis such that the virtual lower jaw is configured to move relative to the virtual upper jaw.

4. The computer-implemented method according to claim 1, wherein the method further comprises defining a search structure on the virtual upper jaw configured for searching on predefined circular paths around the occlusal axis for detecting collisions with the surface of the lower jaw model.

5. The computer-implemented method according to claim 1, wherein a part of the one or more virtual dental restorations which causes a collision is configured to be automatically removed from the respective virtual jaw.

6. The computer-implemented method according to claim 1, wherein the method further comprises that the movement of the virtual upper jaw and the virtual lower jaw relative to each other is configured to be digitally recorded.

7. The computer-implemented method according to claim 1, wherein the method further comprises aligning the virtual upper jaw and virtual lower jaw to correspond to the anatomical alignment of the jaws in the mouth of the patient.

8. The computer-implemented method according to claim 1, wherein the method further comprises positioning a virtual alignment plane relative to the virtual upper jaw and the virtual lower jaw, where the virtual upper jaw and virtual lower jaw defines a virtual model of the set of teeth, wherein the method comprises the steps of:
  visualising the virtual alignment plane and the virtual upper jaw and virtual lower jaw; and
  automatically positioning the virtual alignment plane and the virtual lower jaw and virtual upper jaw relative to each other based on one or more parameters.

9. The computer-implemented method according to claim 8, wherein the positioning of the virtual alignment plane relative to the virtual model of the set of teeth is configured to be performed by the operator by selecting one or more virtual points relative to the virtual model of the set of teeth within which point(s) the virtual alignment plane should be moved to.

10. The computer-implemented method according to claim 8, wherein the virtual alignment plane and/or the virtual model of the set of teeth is/are semi-transparent or translucent such that both the virtual alignment plane and the virtual set of teeth are visible simultaneously.

11. The computer-implemented method according to claim 8, wherein the method further comprises positioning a virtual alignment plane relative to the virtual upper jaw and the virtual lower jaw, where the virtual upper jaw and virtual lower jaw defines a virtual model of the set of teeth, wherein the method comprises the steps of:
  visualising the virtual alignment plane and the virtual upper jaw and virtual lower jaw; and
  automatically positioning the virtual alignment plane and the virtual lower jaw and virtual upper jaw relative to each other.

12. The computer-implemented method according to claim 1, wherein the method further comprises that during the movement of the virtual upper jaw and the virtual lower jaw relative to each other all the collisions occurring between teeth are registered, and after the movement is finished, modeling of the collision points of the displaced virtual model of the one or more dental restorations is performed.

13. The computer-implemented method according to claim 1, wherein a predefined motion of the virtual upper jaw and the virtual lower jaw relative to each other is configured to be played.

14. The computer-implemented method according to claim 1, wherein the method further comprises designing the one or more dental restorations.

15. The computer-implemented method according to claim 1, wherein the positions of teeth within the upper jaw are unchanged relative to the virtual three dimensional model of the upper jaw in the dynamic virtual articulator and the positions of the teeth within the lower jaw are unchanged relative to the virtual three dimensional model of the lower jaw included in the dynamic virtual articulator.

16. A virtual articulator system for simulating occlusion of teeth, where the system comprises:
  a virtual articulator comprising a virtual three-dimensional model of the upper jaw and a virtual three-dimensional model of the lower jaw resembling the upper jaw and lower jaw, respectively, of the patient's mouth, wherein the virtual three-dimensional model of the upper jaw and the virtual three-dimensional model of the lower jaw include three dimensional models of teeth without restorations, and at least one of the virtual three-dimensional model of the upper jaw and the virtual three-dimensional model of the lower jaw with three dimensional models of teeth including one or more dental restorations;
  wherein the controller is further configured for displacing the at least one or more virtual dental restorations vertically relative to the jaw from an original position on at least one of the virtual three-dimensional model of the upper jaw and the virtual three-dimensional model of the lower jaw in order to provide a relative offset of the at least one or more virtual dental restorations;
  a controller configured for moving the virtual three-dimensional model of the upper jaw and the virtual three-dimensional model of the lower jaw relative to each other for simulating dynamic occlusion when performing computer-aided designing of the one or more dental restorations for a patient, whereby collisions between the teeth in the virtual upper and virtual lower jaw occur; and
  wherein the controller is further configured to provide that the teeth in the virtual three-dimensional model of the upper jaw and the virtual three-dimensional model of the lower jaw are blocked from penetrating each other's virtual surfaces in the collisions while permitting penetration of the at least one or more displaced virtual dental restorations, wherein the permission of the penetration is based on a preference of an operator or a user.

17. A computer-implemented method of simulating occlusion of teeth, the method comprises using a dynamic virtual articulator when performing computer-aided designing of one or more dental restorations for a patient, the method further comprises:
  providing the dynamic virtual articulator, the dynamic virtual articulator including a virtual three-dimensional model of the upper jaw and a virtual three-dimensional model of the lower jaw resembling the upper jaw and lower jaw, respectively, of the patient's mouth, wherein the virtual three-dimensional model of the upper jaw and the virtual three-dimensional model of the lower jaw include three dimensional models of physical teeth without restorations, and at least one of the virtual three-dimensional model of the upper jaw and the virtual three-dimensional model of the lower jaw with three dimensional models of teeth including one or more dental restorations;

displacing the virtual model of the one or more dental restorations vertically relative to the jaw from an original position on at least one of the virtual three-dimensional model of the upper jaw and the virtual three-dimensional model of the lower jaw in order to provide a relative offset of the virtual model of the one or more dental restorations;

providing movement of the virtual three-dimensional model of the upper jaw and the virtual three-dimensional model of the lower jaw relative to each other for simulating dynamic occlusion, whereby collisions between the teeth in the virtual upper and virtual lower jaw occur;

detecting collisions of only the physical teeth during simulation of the dynamic occlusion by letting the displaced virtual model of the one or more dental restorations be penetrable; and using the physical teeth as a guide for determining the relative movement between the upper jaw and lower jaw.

* * * * *